US005756289A

United States Patent [19]
Hoekstra

[11] Patent Number: 5,756,289
[45] Date of Patent: May 26, 1998

[54] PROTEIN KINASES

[75] Inventor: Merl F. Hoekstra, Shohomish, Wash.

[73] Assignee: Salk Institute for Biological Studies, La Jolla, Calif.

[21] Appl. No.: 453,866

[22] Filed: May 30, 1995

Related U.S. Application Data

[60] Division of Ser. No. 185,359, Jan. 21, 1994, which is a continuation-in-part of Ser. No. 8,001, Jan. 21, 1993, abandoned, which is a continuation-in-part of Ser. No. 728,783, Jul. 3, 1991, abandoned.

[51] Int. Cl.$^6$ .............................. C12Q 1/68; C12Q 1/48; G01N 33/573

[52] U.S. Cl. .............................. 435/6; 435/72; 435/7.4; 435/7.6; 435/15; 435/963

[58] Field of Search .............................. 435/15, 7.2, 7.4, 435/963, 6

[56] References Cited

PUBLICATIONS

S. Murao et al. "A protein contianing the cystic fibrosis antigen is an inhibitor of protein kinases." J. Biol. Chem. 264: 8356–8360, 1989.

T. Chijiwa et al. "A newly synthesized selective casein kinase I inhibitor, N-(2-aminoethyl-5-chloroisoquinoline-S-sulfamide, and affinity purification of casein kinase I from bovine testis" J. Biol. Chem. 264: 4924–4927, 1989.

Bazenet et al. Erythroid–membrane–bound protein kinase binds to a membrane component and is regulated by phosphatidylinositol 4,5-biphosphate. J. Biol. Chem. 265: 7369–7376, May 5, 1990.

Alani, et al., "A method for gene disruption that allows repeated use of URA3 selection in the construction of multiply disrupted yeast strains", Genetics 116:541–545, 1987.

Arriza et al., "Cloning of human mineralocorticoid receptor complementary DNA: structural and functional kinship with the glucocorticoid receptor", Science 237:268–275, 1987.

Bohmann, et al., "Human proto–oncogene c–jun encodes a DNA binding protein with structural and functional properties of transcription factor AP–1", Science 238:1386–1392, 1987.

Boyle et al., "Phosphopeptide mapping and phosphoamino acid analysis by two dimensional separation on thin layer cellulose plates", Meth. Enzymol. 200:110–149, 1991.

Brockman, et al., "Cell cycle–dependent localization of casein kinase I to mitotic spindles", Proc.Natl.Acad.Sci. (USA) 89:9454–9458, 1992.

Cech, et al., "Ribozymes and their medical application", J.Am.Med.Assoc. 260:3030–3034, 1988.

Coffman, et al., "Xotch, the Xenopus homolog of Drosphila Notch", Science 249:1438–1441, 1990.

Cole, et al., "Two DNA repair and recombination genes in Saccharomyces cerevisiae, RAD52, and RAD54, are induced during meiosis", Mol.Cell.Biol. 9:3101–3103, 1989.

Colicelli et al., "Isolation and characterization of a mammalian gene encoding a high–affinity cAMP phosphodiesterase", PNAS 86:3599–3603 (1989).

Courey, et al., "Analysis of Sp1 In Vivo Multiple transcriptional domains, including a novel glutamine–rich acitivation motif", Cell 55:887–898, 1988.

DeMaggio, et al., "The budding yeast HRR25 gene product is a casei kinase I isoform", Proc. Natl.Acad.Sci. (USA) 89: 7008–7012 (1992).

Devereux, et al., "A comprehensive set of sequence analysis programs for the VAX", Nucl.Acids Res. 12:387–395, 1984.

Fikes, et al., "Striking conservation of TFIID in Schizosaccharomyces pombe and Saccharomyces cerevisiae", Nature 346:291–294, 1990.

Fraley et al., "New generation liposomes: the engineering of an efficient vehicle for intracellular delivery of nucleic acids", TIBS 6:77–80, 1981.

Game, "Radiation–sensitive mutants and repair in yeast", in Yeast Genetics: Fundamental & Applied Aspects, pp. 109–137, 1983.

Hanks, et al., "The protein kinase family: conserved features and deduced phylogeny of the catalytic domains", Science 241:42–52, 1988.

Haynes, et al., "DNA repair mutagenesis in yeast" in Molecular Biology of the Yeast Saccharomyces, pp. 371–414, 1981.

Heinemann, et al., "Bacterial conjugation plasmids mobilize DNA transfer between bacteria and yeast", Nature 340:205–209, 1989.

Hidaka, et al., "Properties and use of H–series compounds as protein kinase inhibitors", Meth.Enzymol. 201:328–339, 1991.

Hoekstra, et al., "Shuttle mutagenesis: bacterial transposons for genetic manipulations in yeast", Meth.Enzymol. 194:329–342, 1991.

Hoekstra, et al., "HRR25, a putative protein kinase from budding yeast: association with repair of damaged DNA", Science 253:1031–1034, 1991.

Huisman, et al., "A Tn10 –lac Z–kanR–URA3 gene fusion transposon for insertion mutagenesis and fusion analysis of yeast and bacterial genes," Genetics 116:191–199, 1987.

Hunter, et al., "Transforming gene prouct of Rous sarcoma virus phosphorylates tyrosine," Proc.Natl.Acad.Sci. (USA) 77:1311–1315, 1980.

Hutter, et al., "Microbial determination by flow cytometry," J.Gen.Microbiol. 113:369–372, 1979.

(List continued on next page.)

Primary Examiner—Robert A. Wax
Assistant Examiner—Gabriele E. Bugaisky
Attorney, Agent, or Firm—Marshall, O'Toole, Gerstein, Murray & Borun

[57] ABSTRACT

Protein kinase mutant and wild-type genes encoding polypeptides of the class heretofore designated "casein kinase I" and useful in screening compositions which may affect DNA double-strand break repair activity are disclosed. Also disclosed are methods using the polynucleotides in cell-proliferative disorders.

2 Claims, 3 Drawing Sheets

OTHER PUBLICATIONS

Ito, et al., "Transformation of intact yeast cells treated with alkali cations," *J. Bacteriol.* 153:163–168, 1983.

Koerner, et al., "High-expression vectors with multiple cloning sites for construction of $_{trp}$E fusion genes: pATH vectors," *Meth.Enzymol.* 194:477–490, 1991.

Kohler, et al., "Continuous cultures of fused cells secreting antibody of predefined specificity," *Nature* 256:495–497, 1975.

Kostriken, et al., "The product of the HO gene is a nuclease: purification and characterization of the enzyme," *Cold Spring Harbor Symp.Quant. Biol.* 49:89–96, 1984.

Lee, et al., "Complementation used to clone a human homologue of the fission yeast cell cycle control gene cdc 2," *Nature* 327:31–35, 1987.

Lindberg, et al., "cDNA cloning and characterization of eck, an epithelial cell receptor protein–tyrosine kinase in the eck/elk family of protein kinases," *Mol.Cell.Biol.* 10:6316–6324, 1990.

Maniatis, et al., *Molecular Cloning: A Laboratory Manual*, pp. 51–53, 109–112, 1982.

Mannino, et al., "Liposome mediated gene transfer," *Biotechniques* 6:682, 1988.

Marcus–Sekura, "Techniques for using anti–sense oligodeoxyribonucleotides to study gene epression," *Anal.Bioch.* 172:289–295, 1988.

Matsushime, et al., "Novel mammalian protein kinase gene (mak) is highly expressed in testicular cells at and after metaphase," *Mol.Cell.Biol.* 10:2261–2268, 1990.

Maundrell, "nmt 1 of fission yeast," *J.Biol.Chem.* 265:10857–10864, 1990.

Moreland, et al., "Amino acid sequences that determine the nuclear localization of yeast histone 2B," *Mol.Cell.Biol.* 7:4048–4057, 1987.

Moreno, et al., "Molecular genetic analysis of fission yeast *Schizosaccharomyces pombe*," *Meth.Enzymol.* 194:795–823, 1991.

Nickoloff, et al., "Double–strand breaks stimulate alternative mechanisms of recombination repair," *J.Mol. Biol.* 207:527–541, 1989.

Robinson, et al., "Yeast casein kinase I homologues: an essential gene pair," *Proc.Natl.Acad. Sci. (USA)* 89:28–32, 1992.

Rose, et al., "A *Saccharomyces cerevisiae* genomic plasmid bank based on a centromere–containing shuttle vecor," *gene* 60:237–243, 1987.

Roussou, et al., "Transcriptional–translational regulatory circuit in *Saccharomyces cerevisiae* which involves the GCN4 transcriptional activator and GCN2 protein kinase," *Mol.Cell.Biol.* 8:2132–2139, 1988.

Rowles, et al., "Purification of casein kinase I and isolation of cDNAs encoding multiple casein kinase I–like enzymes," *Proc.Natl.Acad.Sci. (USA)* 88:9548–9552, 1991.

Silver, et al., "Yeast proteins that recognize nuclear localization sequences," *J.Cell.Biol.* 109:983–989, 1989.

Tuazon, et al., "Casein kinase I and II – multipotential serine protein kinases: structure function, and regulation," *Adv.Sec-.Mess. & Phosphoprotein Res.* 23:123–164, 1991.

Wang, et al., "Two genes in *Saccharomyces cerevisiae* encode a membrane–bound form of casein kinase–1," *Mol. Biol.Cell.* 3:275, 1995.

Wharton, et al., "opa: a novel family of transcribed repeats shared by the *Nothc* locus and other developmentally regulated loci in D. melanogaster," *Cell* 40:55–62, 1985.

Weintraub, "Antisense RNA and DNA," *Sci.Am.* 262:40–46, 1990.

Williamson, et al., "The use of fluorescent DNA–binding agent for detecting and separating yeast mitochondrial DNA," *Meth.Cell.Biol.* 12:335–351, 1975.

```
Hrr25       -------MDLRVGRKFRIGRKIGSGSFGDIYHGTNLISG----------------EEVA
Yck1/Cki2   ----SSRDDSTIIGLHYKIGKKIGEGSFGVLFEGTNMING----------------VPVA
Yck2/Cki1   -SGSQSRDDSTIIGLHYKIGKKIGEGSFGVLFEGTNMING----------------LPVA
Nuf1        ---MSQRSSQHIVGIHYAVGPKIGEGSFGVIFEGENILHSCQAQTGSKRDSSIIMANEPVA
Hhp1        -----MALDLRIGNKYRIGRKIGSGSFGDIYLGTNVVSG-----------------EEVA
Hhp2        -------MTVVDIKIGNKYRIGRKIGSGSFGQIYLGLNTVNG---------------EQVA
CKIα1Hu     MASSSGSKAEFIVGGKYKLVRKIGSGSFGDIYLAINITNG----------------EEVA
CKIα2Hu     MASSSGSKAEFIVGGKYKLVRKIGSGSFGDIYLAINITNG----------------EEVA
CKIα3Hu     MASSSGSKAEFIBGGKYKLVRKIGSGSFGDIYLAINITNG----------------EEVA
Common      ------G-KYKIGRKIGSGSFGDIY-GTN--NG-----------------------E-VA Hrr25       IKLESIRSHPQLDYESRVYRYLSGGVGIPFIRWFGREGEYNAMVIDLLGPSLEDLFNYCH
Yck1/Cki2   IKFEPRKTEAPQLRDEYKTYKILNGTPNIPYAYYFGQEGLHNILVIDLLGPSLEDLFDWCG
Yck2/Cki1   IKFEPRKTEAPQLKDEYRTYKILAGTPGIPQEYYFGQEGLHNILVIDLLGPSLEDLFDWCG
Nuf1        IKFEPRHSDAPQLRDEFRAYRILNGCVGIPHAYYFGQEGMHNILIIDLLGPSLEDLFEWCN
Hhp1        IKLESTRAKHPQLEYEYRVYRILSGGVGIPFVRWFGVECDYNAMVMDLLGPSLEDLFNFCG
Hhp2        VKLEPLKARHHQLEYEFRVYNILKGNIGIPTIRWFGVTNSYNAMVMDLLGPSLEDLFCYCG
CKIα1Hu     VKLESQKARHPQLLYESKLYKILQGGVGIPHIRWYGQEKDYNVLVMDLLGPSLEDLFNFCS
CKIα2Hu     VKLESQKARHPQLLYESKLYKILQGGVGIPHIRWYGQEKDYNVLVMDLLGPSLEDLFNFCS
CKIα3Hu     VKLESQKARHPQLLYESKLYKILQGGVGIPHIRWYGQEKDYNVLVMDLLGPSLEDLFNFCS
Common      IKLEP-KA-HPQL-YE-RVYKIL-G-VGIP--RWFG--G-YNALVIDLLGPSLEDLF--CG Hrr25       RRFSFKTVIMLALQMFCRIQYIHGRSFIHRDIKPDNFLMG--VGRRGST-----------
Yck1/Cki2   RKFSVKTVVQVAVQMITLIEDLHAHDLIYRDIKPDNFLIGRPGQPDANN-----------
Yck2/Cki1   RRFSVKTVLLLADQLITLIEDLHAHDLIYRDIKPDNFLIGRPGQPDANK-----------
Nuf1        RKFSVKTTCMVAKQMIDRVRAIHDHDLIYRDIKPDNFLISQYQRISPEGKVIKSCASSSNN
Hhp1        RKFSLKTVLLLADQLISRIEFIHSKSFLHRDIKPDNFLMG--IGKRGNQ-----------
Hhp2        RKFTLKTVLLLADQLISRIEYVHSKSFLHRDIKPDNFLM---KKHSNV------------
CKIα1Hu     RRFTMKTVLMLADQMISRIEYVHTKNFIHRDIKPDNFLMG--IGRHCNK-----------
CKIα2Hu     RRFTMKTVLMLADQMISRIEYVHTKNFIHRDIKPDNFLMG--IGRHCNK-----------
CKIα3Hu     RRFTMKTVLMLADQMISRIEYVHTKNFIHRDIKPDNFLMG--IGRHCNKCLESPVGKRKRS
Common      RRFS-KTVLMLADQMISRIEYIH--DFIHRDIKPDNFLMG---G---N------------

Hrr25       -------VHVIDFGLSKKYRDFNTHRHIPYRENKSLTGTARYASVNTHLGIE
Yck1/Cki2   -------IHLIDFGMAKQYRDPKTKQHIPYREKKSLSGTARYMSINTHIGRE
Yck2/Cki1   -------VHLIDFGMAKQYRDPKTKQHIPYREKKSLSGTARYMSINTHIGRE
Nuf1        NDPNL--IYMVDFGMAKQYRDPRTKQHIPYRERKSLSGTARYMSINTHFGRE
Hhp1        -------VNIIDFGLAKKYRDHKTHLHIPYRENKNLTGTARYASINTHIGIE
Hhp2        -------VTMIDFGLAKKYRDFKTHVHIPYRDNKNLTGTARYASINTHIGIE
CKIα1Hu     -------LFLIDFGLAKKYRDNRTRQHIPYREDKNLTGTARYASINAHLGIE
CKIα2Hu     -------LFLIDFGLAKKYRDNRTRQHIPYREDKNLTGTARYASINAHLGIE
CKIα3Hu     -------IGRHCNKCLESPVGKRKRS
            MTVSTSQDPSFSGLNQLFLIDFGLAKKYRDNRTRQHIPYREDKNLTGTARYASINAHLGIE
Common      -------VHLIDFGLAKKYRDPKTHQHIPYRENKSLTGTARYASINTHLGIE
```

FIGURE 2A

```
Hrr25       QSRRDDLESLGYVLIYFCKGSLPWQGLKATTKKQKYDRIMEKKLNVSVETLCSGLPL--EF
Yck1/Cki2   QSRRDDMEALGHVFFYFLRGHLPWQGLQAPNNKQKYEKIGEKKRLTNLYDLAQGLPV--QF
Yck2/Cki1   QSRRDDMEAMGHVFFYFLRGQLPWQGLQAPNNKQKYEKIGEKKRLTNLYDLAQGLPI--QF
Nuf1        QSRRDDLESLGHVFFYFYFLRGSLPWQGLKAPNNKLKYEKIGMTKQKLNPDDLLNNAIPYQF
Hhp1        QSRRDDLESLGYVLVYFCRGSLPWQGLAATTKKQKYEKIMEKKISTPTEVLCRGFPQ--EF
Hhp2        QSRRDDLESLGYVLLYFCRGSLPWQGLQADTKEQKYQRIRDTKIGTPLEVLCKGLPE--EF
CKIα1Hu     QSRRDDMESLGYVLMYFNRTSLPWQGLKAATKKQKYEKISEKKMSTPVEVLCKGFPA--EF
CKIα2Hu     QSRRDDMESLGYVLMYFNRTSLPWQGLKAATKKQKYEKISEKKMSTPVEVLCKGFPA--EF
CKIα3Hu     QSRRDDMESLGYVLMYFNRTSLPWQGLKAATKKQKYEKISEKKMSTPVEVLCKGFPA--EF
Common      QSRRDDMESLGYVL-YF-RGSLPWQGLKAPTKKQKYEKIGEKK--T-LEVLC-GLP---EF Hrr25       -QEYMAYCKNLKFDEKPDYLFLARLFKDLSIKLEYHNDHLFDWTMLRYTKAMVE
Yck1/Cki2   GRYLEIVERSLSFEECPDYEGYRKLLLSVLDDLGETADGQYDWMKLNDGRG
Yck2/Cki1   GRYLEIVERNLSFEETPDYEGYRMLLSVLDDLGETADGQYDWMKLNGGRG
Nuf1        -ATYLKYARSLKFDEDPDYDYLISLMDDALRLNDLKDDGHYDWMDLNGGKG
Hhp1        -SIYLNYTRSLRFDDKPDAYFRKRLRKDFCRQSEEFNYMLFDWTLKRKT
Hhp2        -T-YMCYTRQLSFTEKPNYAYLMKAFRDLLIRKGYQYDYVFDWMILK
CKIα1Hu     -AMYLNYCRGLRFEEAPDYMYLRQLFRTLNHQYDYTFDWTMLKQKAAQQAASSSGQG
CKIα2Hu     -AMYLNYCRGLRFEEAPDYMYLRQLFRILFRTLNHQYDYTFDWTMLKQKAAQQAASSSGQG
CKIα3Hu     -AMYLNYCRGLRFEEAPDYMYLRQLFRILFRTLNHQYDYTFDWTMLKQKAAQQAASSSGQG
Common      ---YL-Y-R-LSFDEKPDY-YLR-LF--LL------D--FDWT-L-

CKIα1Hu     QQAQTPTGF
CKIα2Hu     QQAQTPTGFKQTDKTKSNMKGF
CKIα3Hu     QQAQTPTGFKQTDKTKSNMKG
```

FIGURE 2B

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
  ( A ) LENGTH: 3098 base pairs
  ( B ) TYPE: nucleic acid
  ( C ) STRANDEDNESS: single
  ( D ) TOPOLOGY: linear ( i i ) MOLECULE TYPE: DNA (genomic)

( v i i ) IMMEDIATE SOURCE:
  ( B ) CLONE: Protein Kinase ( i x ) FEATURE:
  ( A ) NAME/KEY: CDS
  ( B ) LOCATION: 879..2360

( x i ) SEQUENCE DESCRIPTION: SEQ ID NO:1:

```
GTCGACTCGC CAATCACCAA GTTCTTATCC CACATCCGAC CAGTGTCTGA GTCATGGTTT        60

ACCACCACCA TACCATGCT GGTCATTTGT AAATCCGTTT CTATTACATC AGCACCTGCT        120

GCATAAGCCT TCTCAAATGC TAGTAGCGTA TTTTCAGGAT ATCTTGCTTT AAAAGCTCTG       180

TGGCCCACAA TTTCAACCAT CCTCGTGTCC TTGTTGTTAT CTTACACTTC TTATTTATCA      240

ATAACACTAG TAACATCAAC AACACCAATT TTATATCTCC CTTAATTGTA TACTAAAAGA      300

TCTAAACCAA TTCGGTATTG TCCTCGATAC GGCATGCGTA TAAAGAGATA TAATTAAAAG      360

AGGTTATAGT CACGTGATGC AGATTACCCG CAACAGTACC ACAAAATGGA TACCATCTAA      420

TTGCTATAAA AGGCTCCTAT ATACGAATAA CTACCACTGG ATCGACGATT ATTTCGTGGC      480

AATCATATAC CACTGTGAAG AGTTACTGCA ACTCTCGCTT TGTTTCAACG CTTCTTCCCG      540

TCTGTGTATT TACTACTAAT AGGCAGCCCA CGTTTGAATT TCTTTTTTTC TGGAGAATTT      600

TTGGTGCAAC GAGGAAAAGG AGACGAAGAA AAAAGTTGA AACACGACCA CATATATGGA       660

ACGTGGTTGA AATACAAAGA GAAGAAAGGT TCGACACTCG AGGAAAGCAT TTGGTGGTGA      720

AAACACATCT TAGTAGCATC TTTAAACCTC TGTTGGGTAC TTAGAAAAAT ATTTCCAGAC      780

TTCAAGGATA AAAAAAGTCG AAAAGTTACG ACATATTCGA CCAAAAAAAA AAACCAAAAA      840

GAAAAGATAT ATTTATAGAA AGGATACATT AAAAAGAG ATG GAC TTA AGA GTA           893
                                         Met Asp Leu Arg Val
                                          1               5

GGA AGG AAA TTT CGT ATT GGC AGG AAG ATT GGG AGT GGT TCC TTT GGT         941
Gly Arg Lys Phe Arg Ile Gly Arg Lys Ile Gly Ser Gly Ser Phe Gly
              10                  15                  20

GAC ATT TAC CAC GGC ACG AAC TTA ATT AGT GGT GAA GAA GTA GCC ATC         989
Asp Ile Tyr His Gly Thr Asn Leu Ile Ser Gly Glu Glu Val Ala Ile
              25                  30                  35

AAG CTG GAA TCG ATC AGG TCC AGA CAT CCT CAA TTG GAC TAT GAG TCC        1037
Lys Leu Glu Ser Ile Arg Ser Arg His Pro Gln Leu Asp Tyr Glu Ser
              40                  45                  50

CGC GTC TAC AGA TAC TTA AGC GGT GGT GTG GGA ATC CCG TTC ATC AGA        1085
Arg Val Tyr Arg Tyr Leu Ser Gly Gly Val Gly Ile Pro Phe Ile Arg
              55                  60                  65
```

| | | | | | | | | | | | | | | | | |
|---|---|---|---|---|---|---|---|---|---|---|---|---|---|---|---|---|
| TGG | TTT | GGC | AGA | GAG | GGT | GAA | TAT | AAT | GCT | ATG | GTC | ATC | GAT | CTT | CTA | 1133 |
| Trp 70 | Phe | Gly | Arg | Glu 75 | Gly | Glu | Tyr | Asn | Ala | Met 80 | Val | Ile | Asp | Leu | Leu 85 | |
| GGC | CCA | TCT | TTG | GAA | GAT | TTA | TTC | AAC | TAC | TGT | CAC | AGA | AGG | TTC | TCC | 1181 |
| Gly | Pro | Ser | Leu | Glu 90 | Asp | Leu | Phe | Asn | Tyr 95 | Cys | His | Arg | Arg | Phe | Ser 100 | |
| TTT | AAG | ACG | GTT | ATC | ATG | CTG | GCT | TTG | CAA | ATG | TTT | TGC | CGT | ATT | CAG | 1229 |
| Phe | Lys | Thr | Val 105 | Ile | Met | Leu | Ala | Leu 110 | Gln | Met | Phe | Cys | Arg 115 | Ile | Gln | |
| TAT | ATA | CAT | GGA | AGG | TCG | TTC | ATT | CAT | AGA | GAT | ATC | AAA | CCA | GAC | AAC | 1277 |
| Tyr | Ile | His 120 | Gly | Arg | Ser | Phe | Ile 125 | His | Arg | Asp | Ile | Lys 130 | Pro | Asp | Asn | |
| TTT | TTA | ATG | GGG | GTA | GGA | CGC | GGT | AGC | ACC | GTT | CAT | GTT | ATT | GAT | | 1325 |
| Phe | Leu 135 | Met | Gly | Val | Gly | Arg 140 | Gly | Ser | Thr | Val | His 145 | Val | Ile | Asp | | |
| TTC | GGT | CTA | TCA | AAG | AAA | TAC | CGA | GAT | TTC | AAC | ACA | CAT | CGT | CAT | ATT | 1373 |
| Phe 150 | Gly | Leu | Ser | Lys | Lys 155 | Tyr | Arg | Asp | Phe | Asn 160 | Thr | His | Arg | His | Ile 165 | |
| CCT | TAC | AGG | GAG | AAC | AAG | TCC | TTG | ACA | GGT | ACA | GCT | CGT | TAT | GCA | AGT | 1421 |
| Pro | Tyr | Arg | Glu | Asn 170 | Lys | Ser | Leu | Thr | Gly 175 | Thr | Ala | Arg | Tyr | Ala | Ser 180 | |
| GTC | AAT | ACG | CAT | CTT | GGA | ATA | GAG | CAA | AGT | AGA | AGA | GAT | GAC | TTA | GAA | 1469 |
| Val | Asn | Thr | His 185 | Leu | Gly | Ile | Glu | Gln 190 | Ser | Arg | Arg | Asp | Asp 195 | Leu | Glu | |
| TCA | CTA | GGT | TAT | GTC | TTG | ATC | TAT | TTT | TGT | AAG | GGT | TCT | TTG | CCA | TGG | 1517 |
| Ser | Leu | Gly 200 | Tyr | Val | Leu | Ile | Tyr 205 | Phe | Cys | Lys | Gly | Ser 210 | Leu | Pro | Trp | |
| CAG | GGT | TTG | AAA | GCA | ACC | ACC | AAG | AAA | CAA | AAG | TAT | GAT | CGT | ATC | ATG | 1565 |
| Gln | Gly | Leu | Lys 215 | Ala | Thr | Thr | Lys | Lys 220 | Gln | Lys | Tyr | Asp | Arg 225 | Ile | Met | |
| GAA | AAG | AAA | TTA | AAC | GTT | AGC | GTG | GAA | ACT | CTA | TGT | TCA | GGT | TTA | CCA | 1613 |
| Glu | Lys 230 | Lys | Leu | Asn | Val | Ser 235 | Val | Glu | Thr | Leu | Cys 240 | Ser | Gly | Leu | Pro 245 | |
| TTA | GAG | TTT | CAA | GAA | TAT | ATG | GCT | TAC | TGT | AAG | AAT | TTG | AAA | TTC | GAT | 1661 |
| Leu | Glu | Phe | Gln | Glu 250 | Tyr | Met | Ala | Tyr | Cys 255 | Lys | Asn | Leu | Lys | Phe 260 | Asp | |
| GAG | AAG | CCA | GAT | TAT | TTG | TTC | TTG | GCA | AGG | CTG | TTT | AAA | GAT | CTG | AGT | 1709 |
| Glu | Lys | Pro | Asp 265 | Tyr | Leu | Phe | Leu | Ala 270 | Arg | Leu | Phe | Lys | Asp 275 | Leu | Ser | |
| ATT | AAA | CTA | GAG | TAT | CAC | AAC | GAC | CAC | TTG | TTC | GAT | TGG | ACA | ATG | TTG | 1757 |
| Ile | Lys | Leu | Glu 280 | Tyr | His | Asn | Asp | His 285 | Leu | Phe | Asp | Trp | Thr 290 | Met | Leu | |
| CGT | TAC | ACA | AAG | GCG | ATG | GTG | GAG | AAG | CAA | AGG | GAC | CTC | CTC | ATC | GAA | 1805 |
| Arg | Tyr | Thr | Lys 295 | Ala | Met | Val | Glu | Lys 300 | Gln | Arg | Asp | Leu | Leu 305 | Ile | Glu | |
| AAA | GGT | GAT | TTG | AAC | GCA | AAT | AGC | AAT | GCA | GCA | AGT | GCA | AGT | AAC | AGC | 1853 |
| Lys 310 | Gly | Asp | Leu | Asn | Ala 315 | Asn | Ser | Asn | Ala | Ala 320 | Ser | Ala | Ser | Asn | Ser 325 | |
| ACA | GAC | AAC | AAG | TCT | GAA | ACT | TTC | AAC | AAG | ATT | AAA | CTG | TTA | GCC | ATG | 1901 |
| Thr | Asp | Asn | Lys | Ser 330 | Glu | Thr | Phe | Asn | Lys 335 | Ile | Lys | Leu | Leu | Ala 340 | Met | |
| AAG | AAA | TTC | CCC | ACC | CAT | TTC | CAC | TAT | TAC | AAG | AAT | GAA | GAC | AAA | CAT | 1949 |
| Lys | Lys | Phe | Pro 345 | Thr | His | Phe | His | Tyr 350 | Tyr | Lys | Asn | Glu | Asp 355 | Lys | His | |
| AAT | CCT | TCA | CCA | GAA | GAG | ATC | AAA | CAA | CAA | ACT | ATC | TTG | AAT | AAT | AAT | 1997 |
| Asn | Pro | Ser | Pro 360 | Glu | Glu | Ile | Lys | Gln 365 | Gln | Thr | Ile | Leu | Asn 370 | Asn | Asn | |
| GCA | GCC | TCT | TCT | TTA | CCA | GAG | GAA | TTA | TTG | AAC | GCA | CTA | GAT | AAA | GGT | 2045 |
| Ala | Ala | Ser | Ser 375 | Leu | Pro | Glu | Glu | Leu 380 | Leu | Asn | Ala | Leu | Asp 385 | Lys | Gly | |

| | | | | | | | | | | | | | | | | |
|---|---|---|---|---|---|---|---|---|---|---|---|---|---|---|---|---|
| ATG | GAA | AAC | TTG | AGA | CAA | CAG | CAG | CCG | CAG | CAG | CAG | GTC | CAA | AGT | TCG | 2093 |
| Met | Glu | Asn | Leu | Arg | Gln | Gln | Gln | Pro | Gln | Gln | Gln | Val | Gln | Ser | Ser | |
| 390 | | | | 395 | | | | | 400 | | | | | | 405 | |
| CAG | CCA | CAA | CCA | CAG | CCC | CAA | CAG | CTA | CAG | CAG | CAA | CCA | AAT | GGC | CAA | 2141 |
| Gln | Pro | Gln | Pro | Gln | Pro | Gln | Gln | Leu | Gln | Gln | Gln | Pro | Asn | Gly | Gln | |
| | | | | 410 | | | | | 415 | | | | | 420 | | |
| AGA | CCA | AAT | TAT | TAT | CCT | GAA | CCG | TTA | CTA | CAG | CAG | CAA | CAA | AGA | GAT | 2189 |
| Arg | Pro | Asn | Tyr | Tyr | Pro | Glu | Pro | Leu | Leu | Gln | Gln | Gln | Gln | Arg | Asp | |
| | | | | 425 | | | | | 430 | | | | 435 | | | |
| TCT | CAG | GAG | CAA | CAG | CAG | CAA | GTT | CCG | ATG | GCT | ACA | ACC | AGG | GCT | ACT | 2237 |
| Ser | Gln | Glu | Gln | Gln | Gln | Gln | Val | Pro | Met | Ala | Thr | Thr | Arg | Ala | Thr | |
| | | 440 | | | | | 445 | | | | | 450 | | | | |
| CAG | TAT | CCC | CCA | CAA | ATA | AAC | AGC | AAT | AAT | TTT | AAT | ACT | AAT | CAA | GCA | 2285 |
| Gln | Tyr | Pro | Pro | Gln | Ile | Asn | Ser | Asn | Asn | Phe | Asn | Thr | Asn | Gln | Ala | |
| | 455 | | | | | 460 | | | | | 465 | | | | | |
| TCT | GTA | CCT | CCA | CAA | ATG | AGA | TCT | AAT | CCA | CAA | CAG | CCG | CCT | CAA | GAT | 2333 |
| Ser | Val | Pro | Pro | Gln | Met | Arg | Ser | Asn | Pro | Gln | Gln | Pro | Pro | Gln | Asp | |
| 470 | | | | | 475 | | | | | 480 | | | | | 485 | |
| AAA | CCA | GCT | GGC | CAG | TCA | ATT | TGG | TTG | TAAGCAACAT | ATATTGCTCA | | | | | | 2380 |
| Lys | Pro | Ala | Gly | Gln | Ser | Ile | Trp | Leu | | | | | | | | |
| | | | | 490 | | | | | | | | | | | | |

| | | | | |
|---|---|---|---|---|
| AAACGCACAA | AAATAAACAT | ATGTATATAT | AGACATACAC | ACACACATAT ATATATATAT | 2440 |
| ATTATTATTA | TTATTTACAT | ATACGTACAC | ACAATTCCAT | ATCGAGTTAA TATATACAAT | 2500 |
| TCTGGCCTTC | TTACCTAAAA | AGATGATAGC | TAAAAGAACC | ACTTTTTTTA TGCATTTTTT | 2560 |
| TCTTCGGGAA | GGAAATTAAG | GGGGAGCGGA | GCACCTCTTG | GCCAATTTGT TTTTTTTTA | 2620 |
| TGTAATAAAG | GGCTAACGAT | CGAAGATCAA | TCACGAATAT | TGGACGGTTT TAAAGGAGGG | 2680 |
| CCTCTGAGAA | GACAGCATCA | ATTCGTATTT | TCGATAATTA | ACTTGCCTTA TAGTGTCTGA | 2740 |
| TTAGGAAACA | ATCACGAGAC | GATAACGACG | GAATACCAAG | GAAGTTTGTG CAAATATACA | 2800 |
| GCCGGCACAA | ACAGCAGCTT | CACTCAGGTT | AACTCACATA | CTGTTGAAAA TTGTCGGTAT | 2860 |
| GGAATTCGTT | GCAGAAAGGG | CTCAGCCAGT | TGGTCAAACA | ATCCAGCAGC AAAATGTTAA | 2920 |
| TACTTACGGG | CAAGGCGTCC | TACAACCGCA | TCATGATTTA | CAGCAGCGAC AACAACAACA | 2980 |
| ACAGCAGCGT | CAGCATCAAC | AACTGCTGAC | GTCTCAGTTG | CCCCAGAAAT CTCTCGTATC | 3040 |
| CAAAGGCAAA | TATACACTAC | ATGACTTCCA | GATTATGAGA | ACGCTTGGTA CTGGATCC | 3098 |

( 2 ) INFORMATION FOR SEQ ID NO:2:

( i ) SEQUENCE CHARACTERISTICS:
        ( A ) LENGTH: 494 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Asp | Leu | Arg | Val | Gly | Arg | Lys | Phe | Arg | Ile | Gly | Arg | Lys | Ile | Gly |
| 1 | | | | 5 | | | | | 10 | | | | | 15 | |
| Ser | Gly | Ser | Phe | Gly | Asp | Ile | Tyr | His | Gly | Thr | Asn | Leu | Ile | Ser | Gly |
| | | | 20 | | | | | 25 | | | | | 30 | | |
| Glu | Glu | Val | Ala | Ile | Lys | Leu | Glu | Ser | Ile | Arg | Ser | Arg | His | Pro | Gln |
| | | | 35 | | | | 40 | | | | | 45 | | | |
| Leu | Asp | Tyr | Glu | Ser | Arg | Val | Tyr | Arg | Tyr | Leu | Ser | Gly | Gly | Val | Gly |
| | | 50 | | | | | 55 | | | | | 60 | | | |
| Ile | Pro | Phe | Ile | Arg | Trp | Phe | Gly | Arg | Glu | Gly | Glu | Tyr | Asn | Ala | Met |
| 65 | | | | | 70 | | | | | 75 | | | | | 80 |

| | | | | | | | | | | | | | | |
|---|---|---|---|---|---|---|---|---|---|---|---|---|---|---|
|Val|Ile|Asp|Leu|Leu|Gly|Pro|Ser|Leu|Glu|Asp|Leu|Phe|Asn|Tyr|Cys|
| | | | |85| | | |90| | | | |95| |
|His|Arg|Arg|Phe|Ser|Phe|Lys|Thr|Val|Ile|Met|Leu|Ala|Leu|Gln|Met|
| | | |100| | | |105| | | |110| | | |
|Phe|Cys|Arg|Ile|Gln|Tyr|Ile|His|Gly|Arg|Ser|Phe|Ile|His|Arg|Asp|
| | |115| | | |120| | | |125| | | | |
|Ile|Lys|Pro|Asp|Asn|Phe|Leu|Met|Gly|Val|Gly|Arg|Arg|Gly|Ser|Thr|
| |130| | | | |135| | | |140| | | | |
|Val|His|Val|Ile|Asp|Phe|Gly|Leu|Ser|Lys|Lys|Tyr|Arg|Asp|Phe|Asn|
|145| | | |150| | | |155| | | | |160| |
|Thr|His|Arg|His|Ile|Pro|Tyr|Arg|Glu|Asn|Lys|Ser|Leu|Thr|Gly|Thr|
| | | |165| | | |170| | | |175| | | |
|Ala|Arg|Tyr|Ala|Ser|Val|Asn|Thr|His|Leu|Gly|Ile|Glu|Gln|Ser|Arg|
| | |180| | | |185| | | |190| | | | |
|Arg|Asp|Asp|Leu|Glu|Ser|Leu|Gly|Tyr|Val|Leu|Ile|Tyr|Phe|Cys|Lys|
| |195| | | | |200| | | |205| | | | |
|Gly|Ser|Leu|Pro|Trp|Gln|Gly|Leu|Lys|Ala|Thr|Thr|Lys|Lys|Gln|Lys|
|210| | | | |215| | | |220| | | | | |
|Tyr|Asp|Arg|Ile|Met|Glu|Lys|Lys|Leu|Asn|Val|Ser|Val|Glu|Thr|Leu|
|225| | | |230| | | |235| | | | |240| |
|Cys|Ser|Gly|Leu|Pro|Leu|Glu|Phe|Gln|Glu|Tyr|Met|Ala|Tyr|Cys|Lys|
| | | |245| | | |250| | | |255| | | |
|Asn|Leu|Lys|Phe|Asp|Glu|Lys|Pro|Asp|Tyr|Leu|Phe|Leu|Ala|Arg|Leu|
| | |260| | | |265| | | |270| | | | |
|Phe|Lys|Asp|Leu|Ser|Ile|Lys|Leu|Glu|Tyr|His|Asn|Asp|His|Leu|Phe|
| |275| | | |280| | | |285| | | | | |
|Asp|Trp|Thr|Met|Leu|Arg|Tyr|Thr|Lys|Ala|Met|Val|Glu|Lys|Gln|Arg|
|290| | | |295| | | |300| | | | | | |
|Asp|Leu|Leu|Ile|Glu|Lys|Gly|Asp|Leu|Asn|Ala|Asn|Ser|Asn|Ala|Ala|
|305| | | |310| | | |315| | | | |320| |
|Ser|Ala|Ser|Asn|Ser|Thr|Asp|Asn|Lys|Ser|Glu|Thr|Phe|Asn|Lys|Ile|
| | | |325| | | |330| | | |335| | | |
|Lys|Leu|Leu|Ala|Met|Lys|Lys|Phe|Pro|Thr|His|Phe|His|Tyr|Tyr|Lys|
| | |340| | | |345| | | |350| | | | |
|Asn|Glu|Asp|Lys|His|Asn|Pro|Ser|Pro|Glu|Glu|Ile|Lys|Gln|Gln|Thr|
| |355| | | |360| | | |365| | | | | |
|Ile|Leu|Asn|Asn|Asn|Ala|Ala|Ser|Ser|Leu|Pro|Glu|Glu|Leu|Leu|Asn|
|370| | | |375| | | |380| | | | | | |
|Ala|Leu|Asp|Lys|Gly|Met|Glu|Asn|Leu|Arg|Gln|Gln|Gln|Pro|Gln|Gln|
|385| | | |390| | | |395| | | |400| | |
|Gln|Val|Gln|Ser|Ser|Gln|Pro|Gln|Pro|Gln|Gln|Leu|Gln|Gln|Gln|Gln|
| | | |405| | | |410| | | |415| | | |
|Gln|Pro|Asn|Gly|Gln|Arg|Pro|Asn|Tyr|Tyr|Pro|Glu|Pro|Leu|Leu|Gln|
| | |420| | | |425| | | |430| | | | |
|Gln|Gln|Gln|Arg|Asp|Ser|Gln|Glu|Gln|Gln|Gln|Val|Pro|Met|Ala|
| | |435| | | |440| | | |445| | | | |
|Thr|Thr|Arg|Ala|Thr|Gln|Tyr|Pro|Pro|Gln|Ile|Asn|Ser|Asn|Asn|Phe|
|450| | | |455| | | |460| | | | | | |
|Asn|Thr|Asn|Gln|Ala|Ser|Val|Pro|Pro|Gln|Met|Arg|Ser|Asn|Pro|Gln|
|465| | | |470| | | |475| | | | |480| |
|Gln|Pro|Pro|Gln|Asp|Lys|Pro|Ala|Gly|Gln|Ser|Ile|Trp|Leu|
| | | |485| | | |490| | | | | | |

( 2 ) INFORMATION FOR SEQ ID NO:3:

( i ) SEQUENCE CHARACTERISTICS:
   ( A ) LENGTH: 2469 base pairs
   ( B ) TYPE: nucleic acid
   ( C ) STRANDEDNESS: single
   ( D ) TOPOLOGY: linear ( i i ) MOLECULE TYPE: DNA (genomic)

( v i i ) IMMEDIATE SOURCE:
   ( B ) CLONE: Protein Kinase ( i x ) FEATURE:
   ( A ) NAME/KEY: CDS
   ( B ) LOCATION: 113..1207

( x i ) SEQUENCE DESCRIPTION: SEQ ID NO:3:

```
AATATTTCAA GCTATACCAA GCATACAATC AACTCCAAGC TTCGAGCGGC CGCCAGTGTG        60

CTCTAAAGGA AAAAGCGAGT GCCTTTAGCC TTAAAAGCGT TATAATATTA TT ATG          115
                                                          Met
                                                          1

GCT TTG GAC CTC CGG ATT GGG AAC AAG TAT CGC ATT GGT CGT AAA ATT        163
Ala Leu Asp Leu Arg Ile Gly Asn Lys Tyr Arg Ile Gly Arg Lys Ile
            5                  10                  15

GGC AGT GGA TCT TTC GGA GAC ATT TAT CTT GGG ACT AAT GTC GTT TCT        211
Gly Ser Gly Ser Phe Gly Asp Ile Tyr Leu Gly Thr Asn Val Val Ser
        20                  25                  30

GGT GAA GAG GTC GCT ATC AAG CTA GAA TCA ACT CGT GCT AAA CAC CCT        259
Gly Glu Glu Val Ala Ile Lys Leu Glu Ser Thr Arg Ala Lys His Pro
    35                  40                  45

CAA TTG GAG TAT GAA TAC AGA GTT TAT CGC ATT TTG TCA GGA GGG GTC        307
Gln Leu Glu Tyr Glu Tyr Arg Val Tyr Arg Ile Leu Ser Gly Gly Val
50                  55                  60                  65

GGA ATC CCG TTT GTT CGT TGG TTC GGT GTA GAA TGT GAT TAC AAC GCT        355
Gly Ile Pro Phe Val Arg Trp Phe Gly Val Glu Cys Asp Tyr Asn Ala
                70                  75                  80

ATG GTG ATG GAT TTA TTG GGT CCT TCG TTG GAA GAC TTG TTT AAT TTT        403
Met Val Met Asp Leu Leu Gly Pro Ser Leu Glu Asp Leu Phe Asn Phe
            85                  90                  95

TGC AAT CGA AAG TTT TCT TTG AAA ACA GTT CTT CTC CTT GCG GAC CAG        451
Cys Asn Arg Lys Phe Ser Leu Lys Thr Val Leu Leu Leu Ala Asp Gln
        100                 105                 110

CTC ATT TCT CGA ATT GAA TTC ATT CAT TCA AAA TCT TTT CTT CAT CGT        499
Leu Ile Ser Arg Ile Glu Phe Ile His Ser Lys Ser Phe Leu His Arg
    115                 120                 125

GAT ATT AAG CCT GAT AAC TTT TTA ATG GGA ATA GGT AAA AGA GGA AAT        547
Asp Ile Lys Pro Asp Asn Phe Leu Met Gly Ile Gly Lys Arg Gly Asn
130                 135                 140                 145

CAA GTT AAC ATA ATT GAT TTC GGA TTG GCT AAG AAG TAT CGT GAT CAC        595
Gln Val Asn Ile Ile Asp Phe Gly Leu Ala Lys Lys Tyr Arg Asp His
                150                 155                 160

AAA ACT CAC CTG CAC ATT CCT TAT CGC GAG AAC AAG AAT CTT ACA GGT        643
Lys Thr His Leu His Ile Pro Tyr Arg Glu Asn Lys Asn Leu Thr Gly
            165                 170                 175

ACT GCA CGC TAT GCT AGC ATC AAT ACT CAT TTA GGT ATT GAA CAA TCC        691
Thr Ala Arg Tyr Ala Ser Ile Asn Thr His Leu Gly Ile Glu Gln Ser
        180                 185                 190

CGC CGT GAT GAC CTC GAA TCT TTA GGT TAT GTG CTC GTC TAC TTT TGT        739
Arg Arg Asp Asp Leu Glu Ser Leu Gly Tyr Val Leu Val Tyr Phe Cys
    195                 200                 205

CGT GGT AGC CTG CCT TGG CAG GGA TTG AAG GCT ACC ACG AAA AAG CAA        787
Arg Gly Ser Leu Pro Trp Gln Gly Leu Lys Ala Thr Thr Lys Lys Gln
210                 215                 220                 225
```

| | | | | | | | | | | | | | | | | |
|---|---|---|---|---|---|---|---|---|---|---|---|---|---|---|---|---|
| AAG | TAT | GAA | AAG | ATT | ATG | GAG | AAG | AAG | ATC | TCT | ACG | CCT | ACA | GAG | GTC | 835 |
| Lys | Tyr | Glu | Lys | Ile | Met | Glu | Lys | Lys | Ile | Ser | Thr | Pro | Thr | Glu | Val | |
| | | | | 230 | | | | 235 | | | | | 240 | | | |
| TTA | TGT | CGG | GGA | TTC | CCT | CAG | GAG | TTC | TCA | ATT | TAT | CTC | AAT | TAC | ACG | 883 |
| Leu | Cys | Arg | Gly | Phe | Pro | Gln | Glu | Phe | Ser | Ile | Tyr | Leu | Asn | Tyr | Thr | |
| | | | 245 | | | | | 250 | | | | | 255 | | | |
| AGA | TCT | TTA | CGT | TTC | GAT | GAC | AAA | CCT | GAT | TAC | GCC | TAC | CTT | CGC | AAG | 931 |
| Arg | Ser | Leu | Arg | Phe | Asp | Asp | Lys | Pro | Asp | Tyr | Ala | Tyr | Leu | Arg | Lys | |
| | | | 260 | | | | | 265 | | | | | 270 | | | |
| CTT | TTC | CGA | GAT | CTT | TTT | TGT | CGG | CAA | TCT | TAT | GAG | TTT | GAC | TAT | ATG | 979 |
| Leu | Phe | Arg | Asp | Leu | Phe | Cys | Arg | Gln | Ser | Tyr | Glu | Phe | Asp | Tyr | Met | |
| | | 275 | | | | | 280 | | | | | 285 | | | | |
| TTT | GAT | TGG | ACC | TTG | AAG | AGA | AAG | ACT | CAA | CAA | GAC | CAA | CAA | CAT | CAG | 1027 |
| Phe | Asp | Trp | Thr | Leu | Lys | Arg | Lys | Thr | Gln | Gln | Asp | Gln | Gln | His | Gln | |
| 290 | | | | | 295 | | | | | 300 | | | | | 305 | |
| CAG | CAA | TTA | CAG | CAA | CAA | CTG | TCT | GCA | ACT | CCT | CAA | GCT | ATT | AAT | CCG | 1075 |
| Gln | Gln | Leu | Gln | Gln | Gln | Leu | Ser | Ala | Thr | Pro | Gln | Ala | Ile | Asn | Pro | |
| | | | | 310 | | | | | 315 | | | | | 320 | | |
| CCG | CCA | GAG | AGG | TCT | TCA | TTT | AGA | AAT | TAT | CAA | AAA | CAA | AAC | TTT | GAT | 1123 |
| Pro | Pro | Glu | Arg | Ser | Ser | Phe | Arg | Asn | Tyr | Gln | Lys | Gln | Asn | Phe | Asp | |
| | | | 325 | | | | | 330 | | | | | 335 | | | |
| GAA | AAA | GGC | GGA | GAC | ATT | AAT | ACA | ACC | GTT | CCT | GTT | ATA | AAT | GAT | CCA | 1171 |
| Glu | Lys | Gly | Gly | Asp | Ile | Asn | Thr | Thr | Val | Pro | Val | Ile | Asn | Asp | Pro | |
| | | | 340 | | | | | 345 | | | | | 350 | | | |
| TCT | GCA | ACC | GGA | GCT | CAA | TAT | ATC | AAC | AGA | CCT | AAT | TGATTAGCCT | | | | 1217 |
| Ser | Ala | Thr | Gly | Ala | Gln | Tyr | Ile | Asn | Arg | Pro | Asn | | | | | |
| | | 355 | | | | | 360 | | | | 365 | | | | | |

| | | | | |
|---|---|---|---|---|
| TTCATATTAT | TATTATATAG | CATGGGCACA | TTATTTTTAT | ATTTCTTCT CATCTGGAGT | 1277 |
| CTTCCAATAC | TTGCCTTTTA | TCCTCCAGAC | GTCCTTTAAT | TTGTTGATA GCGCAGGGCT | 1337 |
| TTTTCCTTGG | GATGGCGAAA | GTTACTTTGC | TTATAGTTTA | TTGAGGGTTC ATAGCTTATT | 1397 |
| TGGCTGAAGA | TCTTGTGTTG | ACTTAAATTC | TATGCTAACC | TCATGATCAT ATCCTCATTA | 1457 |
| TGGCAAGTTT | TGGTGAAAAA | TTTTTAATA | TTAGTACATT | TGCTAATAAT ACATTTGGTA | 1517 |
| TTTGTTTTTA | CTACCTGTGA | ATCTATTCAT | ACATTATCAT | ATATGTTTCG AGCCAGGAAC | 1577 |
| AGAAAAAAGT | GAGAGAATTT | TCTGCAGAAA | TGATCATAAT | TTTATCTTCG CTTAACACGA | 1637 |
| ATCCTGGTGA | CAGATTATCG | TGGTTTAAAG | CCTTTTTTT | ACGACGCCAT AAGCAAATTG | 1697 |
| GTTACTTTTT | TATGTGTGAT | GAGCCTTGGG | GTTAATCTA | ATTAGAAGGC ATTGCATTCA | 1757 |
| TATACTTTTA | ATAATATATT | ATCAGCTATT | TGCTGCTTTT | CTTTATAGAT ACCGTCTTTT | 1817 |
| CCAAGCTGAA | CTCATTTAAT | CAGCGTCGTT | TAACCTTAGG | ATGCTTAAGA TGCGTTTAAA | 1877 |
| TTCAATGACT | TAATGCTCGA | GGGATGAATG | GTTGTTTTA | GTTCGTGTTC TGGGTGCATG | 1937 |
| ATCTCGTGCT | TGACTGTTTT | ATTGAAGCGT | TCATTTCATG | AAGTGTCTTT CGATGTTGTT | 1997 |
| CACACTTCTG | TTTGCTAAAT | ATAATAAATA | TTTTGCTTTT | CACTTTAGAG CACACTGGCG | 2057 |
| GCCGCTCGAA | GCTTTGGACT | TCTTCGCCAT | TGGTCAAGTC | TCCAATCAAG GTTGTCGGCT | 2117 |
| TGTCTACCTT | GCCAGAAATT | TACGAAAGA | TGGAAAGGG | ATCCAAATCG TTGGTAGATA | 2177 |
| CTTGTTGACA | CTTCTAAATA | AGCGAATTTC | TTATGATTTA | TGATTTTAT TATTAAATAA | 2237 |
| GTTATAAAAA | AAATAAGGTA | TACAAATTTT | AAAGTGACTC | TTAGGTTTTA AAACGAAAAT | 2297 |
| TCTTATTCTT | GAGTAACTCT | TTCCTGTAGG | TCAGGTTGCT | TTCTCAGGTA TAGCATGAGG | 2357 |
| TCGCTCTTAT | TGACCACACC | TCTACCGGCA | TGCCGAGCAA ATGCCTGCAA ATCGCTCCCC | | 2417 |
| ATTTCACCCA | ATTGTAGATA | TGCTAACTCC | AGCAATGAGC | CGATGAATCT CC | 2469 |

( 2 ) INFORMATION FOR SEQ ID NO:4:

(i) SEQUENCE CHARACTERISTICS:
   (A) LENGTH: 365 amino acids
   (B) TYPE: amino acid
   (D) TOPOLOGY: linear (ii) MOLECULE TYPE: protein (xi) SEQUENCE DESCRIPTION: SEQ ID NO:4:

```
Met Ala Leu Asp Leu Arg Ile Gly Asn Lys Tyr Arg Ile Gly Arg Lys
 1               5                  10                  15

Ile Gly Ser Gly Ser Phe Gly Asp Ile Tyr Leu Gly Thr Asn Val Val
            20                  25                  30

Ser Gly Glu Glu Val Ala Ile Lys Leu Glu Ser Thr Arg Ala Lys His
        35                  40                  45

Pro Gln Leu Glu Tyr Glu Tyr Arg Val Tyr Arg Ile Leu Ser Gly Gly
     50                  55                  60

Val Gly Ile Pro Phe Val Arg Trp Phe Gly Val Glu Cys Asp Tyr Asn
 65                  70                  75                  80

Ala Met Val Met Asp Leu Leu Gly Pro Ser Leu Glu Asp Leu Phe Asn
                85                  90                  95

Phe Cys Asn Arg Lys Phe Ser Leu Lys Thr Val Leu Leu Leu Ala Asp
            100                 105                 110

Gln Leu Ile Ser Arg Ile Glu Phe Ile His Ser Lys Ser Phe Leu His
        115                 120                 125

Arg Asp Ile Lys Pro Asp Asn Phe Leu Met Gly Ile Gly Lys Arg Gly
    130                 135                 140

Asn Gln Val Asn Ile Ile Asp Phe Gly Leu Ala Lys Lys Tyr Arg Asp
145                 150                 155                 160

His Lys Thr His Leu His Ile Pro Tyr Arg Glu Asn Lys Asn Leu Thr
                165                 170                 175

Gly Thr Ala Arg Tyr Ala Ser Ile Asn Thr His Leu Gly Ile Glu Gln
            180                 185                 190

Ser Arg Arg Asp Asp Leu Glu Ser Leu Gly Tyr Val Leu Val Tyr Phe
        195                 200                 205

Cys Arg Gly Ser Leu Pro Trp Gln Gly Leu Lys Ala Thr Thr Lys Lys
    210                 215                 220

Gln Lys Tyr Glu Lys Ile Met Glu Lys Lys Ile Ser Thr Pro Thr Glu
225                 230                 235                 240

Val Leu Cys Arg Gly Phe Pro Gln Glu Phe Ser Ile Tyr Leu Asn Tyr
                245                 250                 255

Thr Arg Ser Leu Arg Phe Asp Asp Lys Pro Asp Tyr Ala Tyr Leu Arg
            260                 265                 270

Lys Leu Phe Arg Asp Leu Phe Cys Arg Gln Ser Tyr Glu Phe Asp Tyr
        275                 280                 285

Met Phe Asp Trp Thr Leu Lys Arg Lys Thr Gln Gln Asp Gln Gln His
    290                 295                 300

Gln Gln Gln Leu Gln Gln Gln Leu Ser Ala Thr Pro Gln Ala Ile Asn
305                 310                 315                 320

Pro Pro Pro Glu Arg Ser Ser Phe Arg Asn Tyr Gln Lys Gln Asn Phe
                325                 330                 335

Asp Glu Lys Gly Gly Asp Ile Asn Thr Thr Val Pro Val Ile Asn Asp
            340                 345                 350

Pro Ser Ala Thr Gly Ala Gln Tyr Ile Asn Arg Pro Asn
        355                 360                 365
```

( 2 ) INFORMATION FOR SEQ ID NO:5:

( i ) SEQUENCE CHARACTERISTICS:
        ( A ) LENGTH: 1989 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 50..1249

( x i ) SEQUENCE DESCRIPTION: SEQ ID NO:5:

```
CCGCCAGTGT GCTCTAAAGG TCATCTCTGT GAATTAGAAT CTTAGCAAA ATG ACG              55
                                                       Met Thr
                                                         1

GTT GTT GAC ATT AAG ATT GGT AAT AAA TAT CGT ATA GGT AGA AAA ATT           103
Val Val Asp Ile Lys Ile Gly Asn Lys Tyr Arg Ile Gly Arg Lys Ile
          5              10                 15

GGT TCT GGC TCC TTT GGT CAA ATT TAC CTG GGA TTA AAT ACG GTA AAT           151
Gly Ser Gly Ser Phe Gly Gln Ile Tyr Leu Gly Leu Asn Thr Val Asn
         20              25                 30

GGA GAA CAA GTT GCT GTG AAA TTG GAG CCT TTA AAG GCT CGT CAT CAT           199
Gly Glu Gln Val Ala Val Lys Leu Glu Pro Leu Lys Ala Arg His His
 35              40                 45                       50

CAG TTA GAA TAT GAG TTT CGT GTG TAT AAT ATT CTT AAA GGA AAT ATT           247
Gln Leu Glu Tyr Glu Phe Arg Val Tyr Asn Ile Leu Lys Gly Asn Ile
             55                 60                 65

GGC ATA CCC ACA ATT CGC TGG TTC GGT GTA ACC AAT AGT TAT AAT GCT           295
Gly Ile Pro Thr Ile Arg Trp Phe Gly Val Thr Asn Ser Tyr Asn Ala
                 70                 75                 80

ATG GTC ATG GAT TTA TTA GGC CCT TCT CTG GAA GAT TTA TTC TGC TAT           343
Met Val Met Asp Leu Leu Gly Pro Ser Leu Glu Asp Leu Phe Cys Tyr
             85                 90                 95

TGT GGA AGA AAG TTT ACT CTT AAA ACG GTT CTT TTA CTT GCT GAT CAA           391
Cys Gly Arg Lys Phe Thr Leu Lys Thr Val Leu Leu Leu Ala Asp Gln
        100                105                110

CTC ATC AGT CGC ATT GAA TAT GTT CAC TCC AAG TCA TTC TTA CAT CGA           439
Leu Ile Ser Arg Ile Glu Tyr Val His Ser Lys Ser Phe Leu His Arg
115                120                125                130

GAC ATT AAG CCT GAT AAT TTT TTA ATG AAG AAG CAC AGC AAT GTT GTT           487
Asp Ile Lys Pro Asp Asn Phe Leu Met Lys Lys His Ser Asn Val Val
                    135                140                145

ACG ATG ATT GAC TTC GGA TTG GCG AAA AAA TAC AGG GAT TTT AAA ACT           535
Thr Met Ile Asp Phe Gly Leu Ala Lys Lys Tyr Arg Asp Phe Lys Thr
                150                155                160

CAT GTT CAT ATT CCA TAT CGA GAT AAT AAG AAT CTT ACG GGA ACG GCT           583
His Val His Ile Pro Tyr Arg Asp Asn Lys Asn Leu Thr Gly Thr Ala
            165                170                175

CGA TAT GCT AGT ATT AAC ACC CAT ATT GGT ATT GAA CAA TCT CGC CGT           631
Arg Tyr Ala Ser Ile Asn Thr His Ile Gly Ile Glu Gln Ser Arg Arg
        180                185                190

GAT GAC CTC GAA TCG TTA GGT TAT GTT TTA CTT TAT TTT TGT CGC GGC           679
Asp Asp Leu Glu Ser Leu Gly Tyr Val Leu Leu Tyr Phe Cys Arg Gly
195                200                205                210

AGT TTG CCC TGG CAA GGC TTA CAA GCT GAT ACA AAG GAG CAA AAG TAT           727
Ser Leu Pro Trp Gln Gly Leu Gln Ala Asp Thr Lys Glu Gln Lys Tyr
                    215                220                225

CAA CGG ATA CGT GAT ACC AAG ATT GGC ACT CCT TTG GAA GTC CTT TGC           775
```

```
        Gln Arg Ile Arg Asp Thr Lys Ile Gly Thr Pro Leu Glu Val Leu Cys
                    230                 235                 240

AAA GGT CTT CCC GAA GAG TTT ATC ACT TAC ATG TGT TAC ACT CGT CAG          823
Lys Gly Leu Pro Glu Glu Phe Ile Thr Tyr Met Cys Tyr Thr Arg Gln
            245                 250                 255

CTT TCG TTT ACC GAG AAG CCA AAC TAT GCT TAT TTG AGA AAG CTG TTT          871
Leu Ser Phe Thr Glu Lys Pro Asn Tyr Ala Tyr Leu Arg Lys Leu Phe
        260                 265                 270

CGT GAT TTA CTT ATT CGT AAA GGA TAC CAG TAT GAC TAT GTT TTT GAC          919
Arg Asp Leu Leu Ile Arg Lys Gly Tyr Gln Tyr Asp Tyr Val Phe Asp
275                 280                 285                 290

TGG ATG ATA TTA AAA TAC CAA AAG CGA GCT GCT GCT GCT GCC GCC GCT          967
Trp Met Ile Leu Lys Tyr Gln Lys Arg Ala Ala Ala Ala Ala Ala Ala
                295                 300                 305

TCT GCT ACA GCA CCT CCA CAG GTT ACA TCT CCT ATG GTG TCA CAA ACT         1015
Ser Ala Thr Ala Pro Pro Gln Val Thr Ser Pro Met Val Ser Gln Thr
            310                 315                 320

CAA CCG GTT AAT CCC ATT ACT CCT AAT TAT TCA TCC ATT CCC TTA CCT         1063
Gln Pro Val Asn Pro Ile Thr Pro Asn Tyr Ser Ser Ile Pro Leu Pro
        325                 330                 335

GCT GAG CGG AAT CCA AAG ACT CCA CAA TCT TTC TCC ACT AAT ATT GTT         1111
Ala Glu Arg Asn Pro Lys Thr Pro Gln Ser Phe Ser Thr Asn Ile Val
340                 345                 350

CAA TGT GCT TCT CCC TCA CCT CTT CCT CTC TCC TTT CGT TCT CCT GTT         1159
Gln Cys Ala Ser Pro Ser Pro Leu Pro Leu Ser Phe Arg Ser Pro Val
355                 360                 365                 370

CCC AAC AAA GAT TAT GAA TAC ATT CCA TCT TCG TTG CAA CCT CAA TAC         1207
Pro Asn Lys Asp Tyr Glu Tyr Ile Pro Ser Ser Leu Gln Pro Gln Tyr
                375                 380                 385

AGT GCT CAA CTG AGG CGT GTT TTA GAT GAA GAA CCA GCT CCT                 1249
Ser Ala Gln Leu Arg Arg Val Leu Asp Glu Glu Pro Ala Pro
            390                 395                 400

TGATTTTTTG ACTTTACTTT TCATCAATTC CTCTCTTACA CTACGTCTTT TAGTCTTAAA       1309

TTCCAAACCA TCTGTTGACG TTTTAAAGTT CCACAAATAT CTTTAATAAT TCCTGGCTTT       1369

CTTTTTTGTC TATGGATGGC CGGATTGCTA CACTAATACA CTTTGAGGTT TAGCTATTGT       1429

TTTGAGCTAT TCCATTTTGC CTAGAAGTTG AGTTTTAATG CCTTCTTTTT AAATAGACAT       1489

ATTGTGTAAA CCTCATACAT GCTTTACTGA AAAGACATAA TTAGAGGACA AAATTTAAAT       1549

CGTGCTGTTT GTTTATATTC AGCTCGTTCC GGTCAAGTTC TTGCCAAAGA ATTGAGTCAG       1609

TCGTGCTATT CATTTCTAAA TTTCTTCTTC CCAGAATTTT ATTTTATTGT TTTCGTTCCC       1669

CATTGGTTCT TACATTCCGT TTTTATTCAA AACTGAAAAG TTTGTACCTC CATTGCTAGA       1729

AGTAATATAC ACAAGGAGCA TGTTTCTTTT TTTACACTAT CATTTGCGTG GCTCTAAACC       1789

AGTCTTTATT GCCTACCTTT GCAATAAAAG ATATAATATC AATTGCATAA GAAATAATTC       1849

ATTAATAAAT GATAAATTTC ATCGATTAAA TAAAAAAAAA AAACTTTAGA GCTTTAGAGC       1909

ACAACTGGCG GCCGCTCGAA GCTTTGGACT TCTTCGCCAT TGGTCAAGTC TCAATCAAGG       1969

TTGTCGGCTT GTCTACCTTC                                                   1989
```

( 2 ) INFORMATION FOR SEQ ID NO:6:

( i ) SEQUENCE CHARACTERISTICS:
        ( A ) LENGTH: 400 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met 1 | Thr | Val | Val | Asp 5 | Ile | Lys | Ile | Gly | Asn 10 | Lys | Tyr | Arg | Ile | Gly 15 | Arg |
| Lys | Ile | Gly | Ser 20 | Gly | Ser | Phe | Gly | Gln 25 | Ile | Tyr | Leu | Gly | Leu 30 | Asn | Thr |
| Val | Asn | Gly 35 | Glu | Gln | Val | Ala | Val 40 | Lys | Leu | Glu | Pro | Leu 45 | Lys | Ala | Arg |
| His | His 50 | Gln | Leu | Glu | Tyr | Glu 55 | Phe | Arg | Val | Tyr | Asn 60 | Ile | Leu | Lys | Gly |
| Asn 65 | Ile | Gly | Ile | Pro | Thr 70 | Ile | Arg | Trp | Phe | Gly 75 | Val | Thr | Asn | Ser | Tyr 80 |
| Asn | Ala | Met | Val | Met 85 | Asp | Leu | Leu | Gly | Pro 90 | Ser | Leu | Glu | Asp | Leu 95 | Phe |
| Cys | Tyr | Cys | Gly 100 | Arg | Lys | Phe | Thr | Leu 105 | Lys | Thr | Val | Leu | Leu 110 | Leu | Ala |
| Asp | Gln | Leu 115 | Ile | Ser | Arg | Ile | Glu 120 | Tyr | Val | His | Ser | Lys 125 | Ser | Phe | Leu |
| His | Arg 130 | Asp | Ile | Lys | Pro | Asp 135 | Asn | Phe | Leu | Met | Lys 140 | Lys | His | Ser | Asn |
| Val 145 | Val | Thr | Met | Ile | Asp 150 | Phe | Gly | Leu | Ala | Lys 155 | Lys | Tyr | Arg | Asp | Phe 160 |
| Lys | Thr | His | Val | His 165 | Ile | Pro | Tyr | Arg | Asp 170 | Asn | Lys | Asn | Leu | Thr 175 | Gly |
| Thr | Ala | Arg | Tyr 180 | Ala | Ser | Ile | Asn | Thr 185 | His | Ile | Gly | Ile | Glu 190 | Gln | Ser |
| Arg | Arg | Asp 195 | Asp | Leu | Glu | Ser | Leu 200 | Gly | Tyr | Val | Leu | Leu 205 | Tyr | Phe | Cys |
| Arg | Gly 210 | Ser | Leu | Pro | Trp | Gln 215 | Gly | Leu | Gln | Ala | Asp 220 | Thr | Lys | Glu | Gln |
| Lys 225 | Tyr | Gln | Arg | Ile | Arg 230 | Asp | Thr | Lys | Ile | Gly 235 | Thr | Pro | Leu | Glu | Val 240 |
| Leu | Cys | Lys | Gly | Leu 245 | Pro | Glu | Glu | Phe | Ile 250 | Thr | Tyr | Met | Cys | Tyr 255 | Thr |
| Arg | Gln | Leu | Ser 260 | Phe | Thr | Glu | Lys | Pro 265 | Asn | Tyr | Ala | Tyr | Leu 270 | Arg | Lys |
| Leu | Phe | Arg 275 | Asp | Leu | Leu | Ile | Arg 280 | Lys | Gly | Tyr | Gln | Tyr 285 | Asp | Tyr | Val |
| Phe | Asp 290 | Trp | Met | Ile | Leu | Lys 295 | Tyr | Gln | Lys | Arg | Ala 300 | Ala | Ala | Ala | Ala |
| Ala 305 | Ala | Ser | Ala | Thr | Ala 310 | Pro | Pro | Gln | Val | Thr 315 | Ser | Pro | Met | Val | Ser 320 |
| Gln | Thr | Gln | Pro | Val 325 | Asn | Pro | Ile | Thr | Pro 330 | Asn | Tyr | Ser | Ser | Ile 335 | Pro |
| Leu | Pro | Ala | Glu 340 | Arg | Asn | Pro | Lys | Thr 345 | Pro | Gln | Ser | Phe | Ser 350 | Thr | Asn |
| Ile | Val | Gln 355 | Cys | Ala | Ser | Pro | Ser 360 | Pro | Leu | Pro | Leu | Ser 365 | Phe | Arg | Ser |
| Pro | Val 370 | Pro | Asn | Lys | Asp | Tyr 375 | Glu | Tyr | Ile | Pro | Ser 380 | Ser | Leu | Gln | Pro |
| Gln 385 | Tyr | Ser | Ala | Gln | Leu 390 | Arg | Arg | Val | Leu | Asp 395 | Glu | Glu | Pro | Ala | Pro 400 |

( 2 ) INFORMATION FOR SEQ ID NO:7:

( i ) SEQUENCE CHARACTERISTICS:

(A) LENGTH: 1210 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
   (B) CLONE: Protein Kinase (ix) FEATURE:
   (A) NAME/KEY: CDS
   (B) LOCATION: 173..1147

(xi) SEQUENCE DESCRIPTION: SEQ ID NO:7:

```
GGCGGTGATC AGTTCCCCTC TGCTGATTCT GGGCCCGAAC CCGGTAAAGG CCTCCGTGTT      60

CCGTTTCCTG CCGCCCTCCT CCGTAGCCTT GCCTAGTGTA GGAGCCCCGA GGCCTCCGTC     120

CTCTTCCCAG AGGTGTCGGG GCTTGCCCCA GCCTCCATCT TCGTCTCTCA GG ATG         175
                                                            Met
                                                            1

GCG AGT AGC AGC GGC TCC AAG GCT GAA TTC ATT GTC GGA GGG AAA TAT       223
Ala Ser Ser Ser Gly Ser Lys Ala Glu Phe Ile Val Gly Gly Lys Tyr
            5                  10                  15

AAA CTG GTA CGG AAG ATC GGG TCT GGC TCC TTC GGG GAC ATC TAT TTG       271
Lys Leu Val Arg Lys Ile Gly Ser Gly Ser Phe Gly Asp Ile Tyr Leu
        20                  25                  30

GCG ATC AAC ATC ACC AAC GGC GAG GAA GTG GCA GTG AAG CTA GAA TCT       319
Ala Ile Asn Ile Thr Asn Gly Glu Glu Val Ala Val Lys Leu Glu Ser
    35                  40                  45

CAG AAG GCC AGG CAT CCC CAG TTG CTG TAC GAG AGC AAG CTC TAT AAG       367
Gln Lys Ala Arg His Pro Gln Leu Leu Tyr Glu Ser Lys Leu Tyr Lys
50                  55                  60                  65

ATT CTT CAA GGT GGG GTT GGC ATC CCC CAC ATA CGG TGG TAT GGT CAG       415
Ile Leu Gln Gly Gly Val Gly Ile Pro His Ile Arg Trp Tyr Gly Gln
                70                  75                  80

GAA AAA GAC TAC AAT GTA CTA GTC ATG GAT CTT CTG GGA CCT AGC CTC       463
Glu Lys Asp Tyr Asn Val Leu Val Met Asp Leu Leu Gly Pro Ser Leu
            85                  90                  95

GAA GAC CTC TTC AAT TTC TGT TCA AGA AGG TTC ACA ATG AAA ACT GTA       511
Glu Asp Leu Phe Asn Phe Cys Ser Arg Arg Phe Thr Met Lys Thr Val
        100                 105                 110

CTT ATG TTA GCT GAC CAG ATG ATC AGT AGA ATT GAA TAT GTG CAT ACA       559
Leu Met Leu Ala Asp Gln Met Ile Ser Arg Ile Glu Tyr Val His Thr
    115                 120                 125

AAG AAT TTT ATA CAC AGA GAC ATT AAA CCA GAT AAC TTC CTA ATG GGT       607
Lys Asn Phe Ile His Arg Asp Ile Lys Pro Asp Asn Phe Leu Met Gly
130                 135                 140                 145

ATT GGG CGT CAC TGT AAT AAG TTA TTC CTT ATT GAT TTT GGT TTG GCC       655
Ile Gly Arg His Cys Asn Lys Leu Phe Leu Ile Asp Phe Gly Leu Ala
                150                 155                 160

AAA AAG TAC AGA GAC AAC AGG ACA AGG CAA CAC ATA CCA TAC AGA GAA       703
Lys Lys Tyr Arg Asp Asn Arg Thr Arg Gln His Ile Pro Tyr Arg Glu
            165                 170                 175

GAT AAA AAC CTC ACT GGC ACT GCC CGA TAT GCT AGC ATC AAT GCA CAT       751
Asp Lys Asn Leu Thr Gly Thr Ala Arg Tyr Ala Ser Ile Asn Ala His
        180                 185                 190

CTT GGT ATT GAG CAG AGT CGC CGA GAT GAC ATG GAA TCA TTA GGA TAT       799
Leu Gly Ile Glu Gln Ser Arg Arg Asp Asp Met Glu Ser Leu Gly Tyr
    195                 200                 205

GTT TTG ATG TAT TTT AAT AGA ACC AGC CTG CCA TGG CAA GGG CTA AAG       847
Val Leu Met Tyr Phe Asn Arg Thr Ser Leu Pro Trp Gln Gly Leu Lys
210                 215                 220                 225
```

| | | | | | | | | | | | | | | | | |
|---|---|---|---|---|---|---|---|---|---|---|---|---|---|---|---|---|
| GCT | GCA | ACA | AAG | AAA | CAA | AAA | TAT | GAA | AAG | ATT | AGT | GAA | AAG | AAG | ATG | 895 |
| Ala | Ala | Thr | Lys<br>230 | Lys | Gln | Lys | Tyr | Glu<br>235 | Lys | Ile | Ser | Glu | Lys<br>240 | Lys | Met | |
| TCC | ACG | CCT | GTT | GAA | GTT | TTA | TGT | AAG | GGG | TTT | CCT | GCA | GAA | TTT | GCG | 943 |
| Ser | Thr | Pro | Val<br>245 | Glu | Val | Leu | Cys | Lys<br>250 | Gly | Phe | Pro | Ala | Glu<br>255 | Phe | Ala | |
| ATG | TAC | TTA | AAC | TAT | TGT | CGT | GGG | CTA | CGC | TTT | GAG | GAA | GCC | CCA | GAT | 991 |
| Met | Tyr | Leu | Asn<br>260 | Tyr | Cys | Arg | Gly | Leu<br>265 | Arg | Phe | Glu | Glu | Ala<br>270 | Pro | Asp | |
| TAC | ATG | TAT | CTG | AGG | CAG | CTA | TTC | CGC | ATT | CTT | TTC | AGG | ACC | CTG | AAC | 1039 |
| Tyr | Met<br>275 | Tyr | Leu | Arg | Gln | Leu<br>280 | Phe | Arg | Ile | Leu | Phe<br>285 | Arg | Thr | Leu | Asn | |
| CAT | CAA | TAT | GAC | TAC | ACA | TTT | GAT | TGG | ACA | ATG | TTA | AAG | CAG | AAA | GCA | 1087 |
| His<br>290 | Gln | Tyr | Asp | Tyr | Thr<br>295 | Phe | Asp | Trp | Thr | Met<br>300 | Leu | Lys | Gln | Lys | Ala<br>305 | |
| GCA | CAG | CAG | GCA | GCC | TCT | TCC | AGT | GGG | CAG | GGT | CAG | CAG | GCC | CAA | ACC | 1135 |
| Ala | Gln | Gln | Ala<br>310 | Ala | Ser | Ser | Ser | Gly<br>315 | Gln | Gly | Gln | Gln | Ala<br>320 | Gln | Thr | |
| CCC | ACA | GGT | TTC | TAAGCATGAA | TTGAGGAACA | GAAGAAGCAG | AGCAGATGAT | | | | | | | | | 1187 |
| Pro | Thr | Gly | Phe<br>325 | | | | | | | | | | | | | |
| CGAGCAGCAT | TTGTTTCTCC | CAA | | | | | | | | | | | | | | 1210 |

(2) INFORMATION FOR SEQ ID NO:8:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO:8:

| | | | | | | | | | | | | | | |
|---|---|---|---|---|---|---|---|---|---|---|---|---|---|---|
| Met<br>1 | Ala | Ser | Ser | Ser<br>5 | Gly | Ser | Lys | Ala | Glu<br>10 | Phe | Ile | Val | Gly | Gly<br>15 | Lys |
| Tyr | Lys | Leu | Val<br>20 | Arg | Lys | Ile | Gly | Ser<br>25 | Gly | Ser | Phe | Gly | Asp<br>30 | Ile | Tyr |
| Leu | Ala | Ile<br>35 | Asn | Ile | Thr | Asn | Gly<br>40 | Glu | Glu | Val | Ala | Val<br>45 | Lys | Leu | Glu |
| Ser | Gln<br>50 | Lys | Ala | Arg | His | Pro<br>55 | Gln | Leu | Leu | Tyr | Glu<br>60 | Ser | Lys | Leu | Tyr |
| Lys<br>65 | Ile | Leu | Gln | Gly | Gly<br>70 | Val | Gly | Ile | Pro | His<br>75 | Ile | Arg | Trp | Tyr | Gly<br>80 |
| Gln | Glu | Lys | Asp | Tyr<br>85 | Asn | Val | Leu | Val | Met<br>90 | Asp | Leu | Leu | Gly | Pro<br>95 | Ser |
| Leu | Glu | Asp | Leu<br>100 | Phe | Asn | Phe | Cys | Ser<br>105 | Arg | Arg | Phe | Thr | Met<br>110 | Lys | Thr |
| Val | Leu | Met<br>115 | Leu | Ala | Asp | Gln | Met<br>120 | Ile | Ser | Arg | Ile | Glu<br>125 | Tyr | Val | His |
| Thr | Lys<br>130 | Asn | Phe | Ile | His | Arg<br>135 | Asp | Ile | Lys | Pro | Asp<br>140 | Asn | Phe | Leu | Met |
| Gly<br>145 | Ile | Gly | Arg | His | Cys<br>150 | Asn | Lys | Leu | Phe | Leu<br>155 | Ile | Asp | Phe | Gly | Leu<br>160 |
| Ala | Lys | Lys | Tyr | Arg<br>165 | Asp | Asn | Arg | Thr | Arg<br>170 | Gln | His | Ile | Pro | Tyr<br>175 | Arg |
| Glu | Asp | Lys | Asn | Leu<br>180 | Thr | Gly | Thr | Ala | Arg<br>185 | Tyr | Ala | Ser | Ile | Asn<br>190 | Ala |
| His | Leu | Gly<br>195 | Ile | Glu | Gln | Ser | Arg<br>200 | Arg | Asp | Asp | Met | Glu<br>205 | Ser | Leu | Gly |

```
Tyr Val Leu Met Tyr Phe Asn Arg Thr Ser Leu Pro Trp Gln Gly Leu
210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
                245                 250                 255

Ala Met Tyr Leu Asn Tyr Cys Arg Gly Leu Arg Phe Glu Glu Ala Pro
            260                 265                 270

Asp Tyr Met Tyr Leu Arg Gln Leu Phe Arg Ile Leu Phe Arg Thr Leu
        275                 280                 285

Asn His Gln Tyr Asp Tyr Thr Phe Asp Trp Thr Met Leu Lys Gln Lys
    290                 295                 300

Ala Ala Gln Gln Ala Ala Ser Ser Ser Gly Gln Gly Gln Gln Ala Gln
305                 310                 315                 320

Thr Pro Thr Gly Phe
                325
```

( 2 ) INFORMATION FOR SEQ ID NO:9:

( i ) SEQUENCE CHARACTERISTICS:
( A ) LENGTH: 2385 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 297..1388

( x i ) SEQUENCE DESCRIPTION: SEQ ID NO:9:

```
GAATTCCGAT AGTATTATGT GGAGTTCCAT TTTTATGTAT TTTTTGTATG AAATATTCTA        60

GTATAAGTAA ATATTTTATC AGAAGTATTT ACATATCTTT TTTTTTTTTA GTTTGAGAGC       120

GGCGGTGATC AGGTTCCCCT CTGCTGATTC TGGGCCCCGA ACCCCGGTAA AGGCCTCCGT       180

GTTCCGTTTC CTGCCGCCCT CCTCCGTAGC CTTGCCTAGT GTAGGAGCCC CGAGGCCTCC       240

GTCCTCTTCC CAGAGGTGTC GGGGCTTGGC CCCAGCCTCC ATCTTCGTCT CTCAGG          296

ATG GCG AGT AGC AGC GGC TCC AAG GCT GAA TTC ATT GTC GGA GGG AAA        344
Met Ala Ser Ser Ser Gly Ser Lys Ala Glu Phe Ile Val Gly Gly Lys
1               5                   10                  15

TAT AAA CTG GTA CGG AAG ATC GGG TCT GGC TCC TTC GGG GAC ATC TAT        392
Tyr Lys Leu Val Arg Lys Ile Gly Ser Gly Ser Phe Gly Asp Ile Tyr
            20                  25                  30

TTG GCG ATC AAC ATC ACC AAC GGC GAG GAA GTG GCA GTG AAG CTA GAA        440
Leu Ala Ile Asn Ile Thr Asn Gly Glu Glu Val Ala Val Lys Leu Glu
        35                  40                  45

TCT CAG AAG GCC AGG CAT CCC CAG TTG CTG TAC GAG AGC AAG CTC TAT        488
Ser Gln Lys Ala Arg His Pro Gln Leu Leu Tyr Glu Ser Lys Leu Tyr
50                  55                  60

AAG ATT CTT CAA GGT GGG GTT GGC ATC CCC CAC ATA CGG TGG TAT GGT        536
Lys Ile Leu Gln Gly Gly Val Gly Ile Pro His Ile Arg Trp Tyr Gly
65                  70                  75                  80

CAG GAA AAA GAC TAC AAT GTA CTA GTC ATG GAT CTT CTG GGA CCT AGC        584
Gln Glu Lys Asp Tyr Asn Val Leu Val Met Asp Leu Leu Gly Pro Ser
            85                  90                  95

CTC GAA GAC CTC TTC AAT TTC TGT TCA AGA AGG TTC ACA ATG AAA ACT        632
Leu Glu Asp Leu Phe Asn Phe Cys Ser Arg Arg Phe Thr Met Lys Thr
        100                 105                 110
```

| | | | | | | | | | | | | | | | | |
|---|---|---|---|---|---|---|---|---|---|---|---|---|---|---|---|---|
| GTA | CTT | ATG | TTA | GCT | GAC | CAG | ATG | ATC | AGT | AGA | ATT | GAA | TAT | GTG | CAT | 680 |
| Val | Leu | Met<br>115 | Leu | Ala | Asp | Gln | Met<br>120 | Ile | Ser | Arg | Ile | Glu<br>125 | Tyr | Val | His | |
| ACA | AAG | AAT | TTT | ATA | CAC | AGA | GAC | ATT | AAA | CCA | GAT | AAC | TTC | CTA | ATG | 728 |
| Thr | Lys<br>130 | Asn | Phe | Ile | His<br>135 | Arg | Asp | Ile | Lys | Pro<br>140 | Asp | Asn | Phe | Leu | Met | |
| GGT | ATT | GGG | CGT | CAC | TGT | AAT | AAG | TGT | TTA | GAA | TCT | CCA | GTG | GGG | AAG | 776 |
| Gly<br>145 | Ile | Gly | Arg | His<br>150 | Cys | Asn | Lys | Cys | Leu<br>155 | Glu | Ser | Pro | Val | Gly<br>160 | Lys | |
| AGG | AAA | AGA | AGC | ATG | ACT | GTT | AGT | ACT | TCT | CAG | GAC | CCA | TCT | TTC | TCA | 824 |
| Arg | Lys | Arg | Ser | Met<br>165 | Thr | Val | Ser | Thr | Ser<br>170 | Gln | Asp | Pro | Ser | Phe<br>175 | Ser | |
| GGA | TTA | AAC | CAG | TTA | TTC | CTT | ATT | GAT | TTT | GGT | TTG | GCC | AAA | AAG | TAC | 872 |
| Gly | Leu | Asn | Gln<br>180 | Leu | Phe | Leu | Ile | Asp<br>185 | Phe | Gly | Leu | Ala | Lys<br>190 | Lys | Tyr | |
| AGA | GAC | AAC | AGG | ACA | AGG | CAA | CAC | ATA | CCA | TAC | AGA | GAA | GAT | AAA | AAC | 920 |
| Arg | Asp | Asn<br>195 | Arg | Thr | Arg | Gln | His<br>200 | Ile | Pro | Tyr | Arg | Glu<br>205 | Asp | Lys | Asn | |
| CTC | ACT | GGC | ACT | GCC | CGA | TAT | GCT | AGC | ATC | AAT | GCA | CAT | CTT | GGT | ATT | 968 |
| Leu | Thr | Gly<br>210 | Thr | Ala | Arg | Tyr | Ala<br>215 | Ser | Ile | Asn | Ala | His<br>220 | Leu | Gly | Ile | |
| GAG | CAG | AGT | CGC | CGA | GAT | GAC | ATG | GAA | TCA | TTA | GGA | TAT | GTT | TTG | ATG | 1016 |
| Glu<br>225 | Gln | Ser | Arg | Arg<br>230 | Asp | Asp | Met | Glu | Ser<br>235 | Leu | Gly | Tyr | Val | Leu | Met<br>240 | |
| TAT | TTT | AAT | AGA | ACC | AGC | CTG | CCA | TGG | CAA | GGG | CTA | AAG | GCT | GCA | ACA | 1064 |
| Tyr | Phe | Asn | Arg | Thr<br>245 | Ser | Leu | Pro | Trp | Gln<br>250 | Gly | Leu | Lys | Ala | Ala<br>255 | Thr | |
| AAG | AAA | CAA | AAA | TAT | GAA | AAG | ATT | AGT | GAA | AAG | AAG | ATG | TCC | ACG | CCT | 1112 |
| Lys | Lys | Gln | Lys<br>260 | Tyr | Glu | Lys | Ile | Ser<br>265 | Glu | Lys | Lys | Met | Ser<br>270 | Thr | Pro | |
| GTT | GAA | GTT | TTA | TGT | AAG | GGG | TTT | CCT | GCA | GAA | TTT | GCG | ATG | TAC | TTA | 1160 |
| Val | Glu | Val<br>275 | Leu | Cys | Lys | Gly | Phe<br>280 | Pro | Ala | Glu | Phe | Ala<br>285 | Met | Tyr | Leu | |
| AAC | TAT | TGT | CGT | GGG | CTA | CGC | TTT | GAG | GAA | GCC | CCA | GAT | TAC | ATG | TAT | 1208 |
| Asn | Tyr<br>290 | Cys | Arg | Gly | Leu | Arg<br>295 | Phe | Glu | Glu | Ala | Pro<br>300 | Asp | Tyr | Met | Tyr | |
| CTG | AGG | CAG | CTA | TTC | CGC | ATT | CTT | TTC | AGG | ACC | CTG | AAC | CAT | CAA | TAT | 1256 |
| Leu<br>305 | Arg | Gln | Leu | Phe | Arg<br>310 | Ile | Leu | Phe | Arg | Thr<br>315 | Leu | Asn | His | Gln | Tyr<br>320 | |
| GAC | TAC | ACA | TTT | GAT | TGG | ACA | ATG | TTA | AAG | CAG | AAA | GCA | GCA | CAG | CAG | 1304 |
| Asp | Tyr | Thr | Phe | Asp<br>325 | Trp | Thr | Met | Leu | Lys<br>330 | Gln | Lys | Ala | Ala | Gln<br>335 | Gln | |
| GCA | GCC | TCT | TCC | AGT | GGG | CAG | GGT | CAG | CAG | GCC | CAA | ACC | CCC | ACA | GGC | 1352 |
| Ala | Ala | Ser | Ser<br>340 | Ser | Gly | Gln | Gly | Gln<br>345 | Gln | Ala | Gln | Thr | Pro<br>350 | Thr | Gly | |
| AAG | CAA | ACT | GAC | AAA | ACC | AAG | AGT | AAC | ATG | AAA | GGT | TAGTAGCCAA | | | | 1398 |
| Lys | Gln | Thr | Asp<br>355 | Lys | Thr | Lys | Ser | Asn<br>360 | Met | Lys | Gly | | | | | |

```
GAACCAAGTG ACGTTACAGG GAAAAAATTG AATACAAAAT TGGGTAATTC ATTTCTAACA    1458

GTGTTAGATC AAGGAGGTGG TTTTAAAATA CATAAAAATT TGGCTCTGCG TTAAAAAAAA    1518

AAAAGACGTC CTTGGAAAAT TTGACTACTA ACTTTAAACC CAAATGTCCT TGTTCATATA    1578

TATGTATATG TATTTGTATA TACATATATG TGTGTATATT TATATCATTT CTCTTGGGAT    1638

TTTGGGTCAT TTTTTTAACA ACTGCATCTT TTTTACTCAT TCATTAACCC CCTTTCCAAA    1698

AATTTGGTGT TGGGAATATA ATATAATCAA TCAATCCAAA ATCCTAGACC TAACACTTGT    1758

TGATTTCTAA TAATGAATTT GGTTAGCCAT ATTTTGACTT TATTTCAGAC TAACAATGTT    1818

AAGATTTTTT ATTTTGCATG TTAATGCTTT AGCATTTAAA ATGGAAAATT GTGAACATGT    1878
```

```
TGTAATTTCA AGAGGTGAGT TTGGCATTAC CCCCAAAGTG TCTATCTTCT CAGTTGCAGA    1938

GCATCTCATT TTCTCTCTTA AATGCTCAAA TAAATGCAAA GCTCAGCACA TCTTTTCTAG    1998

TCACAAAAAT AATTCTTTTA TTTGCAGTTT ACGTATGATC TTAATTTCAA AACGATTTCT    2058

TTGTTTTTGG CTTGATTTTT CACAATGTTG CAAATATCAG GCTCCCAGGG TTTAATGTGG    2118

AATTGAAGTC TGCAGCCAGG CCTTGCAAAT TGAAGGTAAC TGGGGCAAAT GCCATTGAAA    2178

CCGCTAGTCT TATTTCCTTT CTACTTTTCT TTGGCACTCT TACTGCCTGT AAGGAGTAGA    2238

ACTGTTAAGG CACACTGTTG CTATACAGTT AACTCCCATT TTCATGTTTT GTCTTTCTTT    2298

TCCCATTTCT GGGGCTTACC TCCTGATACC TGCTTACTTT CTGGAAGTAG TGGGCAAGTA    2358

AGATTTGGCT CTTGGTTTCT GGAATTC                                        2385
```

( 2 ) INFORMATION FOR SEQ ID NO:10:

( i ) SEQUENCE CHARACTERISTICS:
        ( A ) LENGTH: 364 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Ala Ser Ser Ser Gly Ser Lys Ala Glu Phe Ile Val Gly Gly Lys
 1               5                  10                  15

Tyr Lys Leu Val Arg Lys Ile Gly Ser Gly Ser Phe Gly Asp Ile Tyr
                20                  25                  30

Leu Ala Ile Asn Ile Thr Asn Gly Glu Glu Val Ala Val Lys Leu Glu
            35                  40                  45

Ser Gln Lys Ala Arg His Pro Gln Leu Leu Tyr Glu Ser Lys Leu Tyr
        50                  55                  60

Lys Ile Leu Gln Gly Gly Val Gly Ile Pro His Ile Arg Trp Tyr Gly
 65                 70                  75                  80

Gln Glu Lys Asp Tyr Asn Val Leu Val Met Asp Leu Leu Gly Pro Ser
                85                  90                  95

Leu Glu Asp Leu Phe Asn Phe Cys Ser Arg Arg Phe Thr Met Lys Thr
           100                 105                 110

Val Leu Met Leu Ala Asp Gln Met Ile Ser Arg Ile Glu Tyr Val His
       115                 120                 125

Thr Lys Asn Phe Ile His Arg Asp Ile Lys Pro Asp Asn Phe Leu Met
   130                 135                 140

Gly Ile Gly Arg His Cys Asn Lys Cys Leu Glu Ser Pro Val Gly Lys
145                 150                 155                 160

Arg Lys Arg Ser Met Thr Val Ser Thr Ser Gln Asp Pro Ser Phe Ser
                165                 170                 175

Gly Leu Asn Gln Leu Phe Leu Ile Asp Phe Gly Leu Ala Lys Lys Tyr
            180                 185                 190

Arg Asp Asn Arg Thr Arg Gln His Ile Pro Tyr Arg Glu Asp Lys Asn
        195                 200                 205

Leu Thr Gly Thr Ala Arg Tyr Ala Ser Ile Asn Ala His Leu Gly Ile
    210                 215                 220

Glu Gln Ser Arg Arg Asp Asp Met Glu Ser Leu Gly Tyr Val Leu Met
225                 230                 235                 240

Tyr Phe Asn Arg Thr Ser Leu Pro Trp Gln Gly Leu Lys Ala Ala Thr
                245                 250                 255

Lys Lys Gln Lys Tyr Glu Lys Ile Ser Glu Lys Lys Met Ser Thr Pro
            260                 265                 270
```

| Val | Glu | Val | Leu | Cys | Lys | Gly | Phe | Pro | Ala | Glu | Phe | Ala | Met | Tyr | Leu |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Asn | Tyr | Cys | Arg | Gly | Leu | Arg | Phe | Glu | Glu | Ala | Pro | Asp | Tyr | Met | Tyr |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Leu | Arg | Gln | Leu | Phe | Arg | Ile | Leu | Phe | Arg | Thr | Leu | Asn | His | Gln | Tyr |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Asp | Tyr | Thr | Phe | Asp | Trp | Thr | Met | Leu | Lys | Gln | Lys | Ala | Ala | Gln | Gln |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Ala | Ala | Ser | Ser | Ser | Gly | Gln | Gly | Gln | Gln | Ala | Gln | Thr | Pro | Thr | Gly |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Lys | Gln | Thr | Asp | Lys | Thr | Lys | Ser | Asn | Met | Lys | Gly |
|-----|-----|-----|-----|-----|-----|-----|-----|-----|-----|-----|-----|
|     |     | 355 |     |     |     |     | 360 |     |     |     |     |

( 2 ) INFORMATION FOR SEQ ID NO:11:

( i ) SEQUENCE CHARACTERISTICS:
        ( A ) LENGTH: 2914 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 265..1275

( x i ) SEQUENCE DESCRIPTION: SEQ ID NO:11:

```
GAATTCCCGA GAAACAAGTG GCCCAGCCTG GTAACCGCCG AGAAGCCCTT CACAAACTGC      60

GGCCTGGCAA AAAGAAACCT GACTGAGCGG CGGTGATCAG GTTCCCCTCT GCTGATTCTG     120

GGCCCCGAAC CCCGGTAAAG GCCTCCGTGT TCCGTTTCCT GCCGCCCTCC TCCGTAGCCT     180

TGCCTAGTGT AGGAGCCCCG AGGCCTCCGT CCTCTTCCCA GAGGTGTCGG GGCTTGGCCC     240

CAGCCTCCAT CTTCGTCTCT CAGG ATG GCG AGT AGC AGC GGC TCC AAG GCT       291
              Met Ala Ser Ser Ser Gly Ser Lys Ala
                1               5
```

| GAA | TTC | ATT | GTC | GGA | GGG | AAA | TAT | AAA | CTG | GTA | CGG | AAG | ATC | GGG | TCT | 339 |
|-----|-----|-----|-----|-----|-----|-----|-----|-----|-----|-----|-----|-----|-----|-----|-----|-----|
| Glu | Phe | Ile | Val | Gly | Gly | Lys | Tyr | Lys | Leu | Val | Arg | Lys | Ile | Gly | Ser |     |
| 10  |     |     |     |     | 15  |     |     |     |     | 20  |     |     |     |     | 25  |     |

| GGC | TCC | TTC | GGG | GAC | ATC | TAT | TTG | GCG | ATC | AAC | ATC | ACC | AAC | GGC | GAG | 387 |
|-----|-----|-----|-----|-----|-----|-----|-----|-----|-----|-----|-----|-----|-----|-----|-----|-----|
| Gly | Ser | Phe | Gly | Asp | Ile | Tyr | Leu | Ala | Ile | Asn | Ile | Thr | Asn | Gly | Glu |     |
|     |     |     |     | 30  |     |     |     |     | 35  |     |     |     |     | 40  |     |     |

| GAA | GTG | GCA | GTG | AAG | CTA | GAA | TCT | CAG | AAG | GCC | AGG | CAT | CCC | CAG | TTG | 435 |
|-----|-----|-----|-----|-----|-----|-----|-----|-----|-----|-----|-----|-----|-----|-----|-----|-----|
| Glu | Val | Ala | Val | Lys | Leu | Glu | Ser | Gln | Lys | Ala | Arg | His | Pro | Gln | Leu |     |
|     |     |     | 45  |     |     |     |     | 50  |     |     |     |     | 55  |     |     |     |

| CTG | TAC | GAG | AGC | AAG | CTC | TAT | AAG | ATT | CTT | CAA | GGT | GGG | GTT | GGC | ATC | 483 |
|-----|-----|-----|-----|-----|-----|-----|-----|-----|-----|-----|-----|-----|-----|-----|-----|-----|
| Leu | Tyr | Glu | Ser | Lys | Leu | Tyr | Lys | Ile | Leu | Gln | Gly | Gly | Val | Gly | Ile |     |
|     |     |     | 60  |     |     |     |     | 65  |     |     |     |     | 70  |     |     |     |

| CCC | CAC | ATA | CGG | TGG | TAT | GGT | CAG | GAA | AAA | GAC | TAC | AAT | GTA | CTA | GTC | 531 |
|-----|-----|-----|-----|-----|-----|-----|-----|-----|-----|-----|-----|-----|-----|-----|-----|-----|
| Pro | His | Ile | Arg | Trp | Tyr | Gly | Gln | Glu | Lys | Asp | Tyr | Asn | Val | Leu | Val |     |
|     |     | 75  |     |     |     |     | 80  |     |     |     |     | 85  |     |     |     |     |

| ATG | GAT | CTT | CTG | GGA | CCT | AGC | CTC | GAA | GAC | CTC | TTC | AAT | TTC | TGT | TCA | 579 |
|-----|-----|-----|-----|-----|-----|-----|-----|-----|-----|-----|-----|-----|-----|-----|-----|-----|
| Met | Asp | Leu | Leu | Gly | Pro | Ser | Leu | Glu | Asp | Leu | Phe | Asn | Phe | Cys | Ser |     |
| 90  |     |     |     |     | 95  |     |     |     |     | 100 |     |     |     |     | 105 |     |

| AGA | AGG | TTC | ACA | ATG | AAA | ACT | GTA | CTT | ATG | TTA | GCT | GAC | CAG | ATG | ATC | 627 |
|-----|-----|-----|-----|-----|-----|-----|-----|-----|-----|-----|-----|-----|-----|-----|-----|-----|
| Arg | Arg | Phe | Thr | Met | Lys | Thr | Val | Leu | Met | Leu | Ala | Asp | Gln | Met | Ile |     |
|     |     |     |     | 110 |     |     |     |     | 115 |     |     |     |     | 120 |     |     |

| AGT | AGA | ATT | GAA | TAT | GTG | CAT | ACA | AAG | AAT | TTT | ATA | CAC | AGA | GAC | ATT | 675 |
|-----|-----|-----|-----|-----|-----|-----|-----|-----|-----|-----|-----|-----|-----|-----|-----|-----|
| Ser | Arg | Ile | Glu | Tyr | Val | His | Thr | Lys | Asn | Phe | Ile | His | Arg | Asp | Ile |     |
|     |     |     | 125 |     |     |     |     | 130 |     |     |     |     | 135 |     |     |     |

| | | | | | | | | | | | | | | | | |
|---|---|---|---|---|---|---|---|---|---|---|---|---|---|---|---|---|
| AAA | CCA | GAT | AAC | TTC | CTA | ATG | GGT | ATT | GGG | CGT | CAC | TGT | AAT | AAG | TTA | 723 |
| Lys | Pro | Asp | Asn | Phe | Leu | Met | Gly | Ile | Gly | Arg | His | Cys | Asn | Lys | Leu | |
| | 140 | | | | | 145 | | | | | 150 | | | | | |
| TTC | CTT | ATT | GAT | TTT | GGT | TTG | GCC | AAA | AAG | TAC | AGA | GAC | AAC | AGG | ACA | 771 |
| Phe | Leu | Ile | Asp | Phe | Gly | Leu | Ala | Lys | Lys | Tyr | Arg | Asp | Asn | Arg | Thr | |
| | 155 | | | | | 160 | | | | | 165 | | | | | |
| AGG | CAA | CAC | ATA | CCA | TAC | AGA | GAA | GAT | AAA | AAC | CTC | ACT | GGC | ACT | GCC | 819 |
| Arg | Gln | His | Ile | Pro | Tyr | Arg | Glu | Asp | Lys | Asn | Leu | Thr | Gly | Thr | Ala | |
| 170 | | | | | 175 | | | | | 180 | | | | | 185 | |
| CGA | TAT | GCT | AGC | ATC | AAT | GCA | CAT | CTT | GGT | ATT | GAG | CAG | AGT | CGC | CGA | 867 |
| Arg | Tyr | Ala | Ser | Ile | Asn | Ala | His | Leu | Gly | Ile | Glu | Gln | Ser | Arg | Arg | |
| | | | | 190 | | | | | 195 | | | | | 200 | | |
| GAT | GAC | ATG | GAA | TCA | TTA | GGA | TAT | GTT | TTG | ATG | TAT | TTT | AAT | AGA | ACC | 915 |
| Asp | Asp | Met | Glu | Ser | Leu | Gly | Tyr | Val | Leu | Met | Tyr | Phe | Asn | Arg | Thr | |
| | | | 205 | | | | | 210 | | | | | 215 | | | |
| AGC | CTG | CCA | TGG | CAA | GGG | CTA | AAG | GCT | GCA | ACA | AAG | AAA | CAA | AAA | TAT | 963 |
| Ser | Leu | Pro | Trp | Gln | Gly | Leu | Lys | Ala | Ala | Thr | Lys | Lys | Gln | Lys | Tyr | |
| | | 220 | | | | | 225 | | | | | 230 | | | | |
| GAA | AAG | ATT | AGT | GAA | AAG | AAG | ATG | TCC | ACG | CCT | GTT | GAA | GTT | TTA | TGT | 1011 |
| Glu | Lys | Ile | Ser | Glu | Lys | Lys | Met | Ser | Thr | Pro | Val | Glu | Val | Leu | Cys | |
| | 235 | | | | | 240 | | | | | 245 | | | | | |
| AAG | GGG | TTT | CCT | GCA | GAA | TTT | GCG | ATG | TAC | TTA | AAC | TAT | TGT | CGT | GGG | 1059 |
| Lys | Gly | Phe | Pro | Ala | Glu | Phe | Ala | Met | Tyr | Leu | Asn | Tyr | Cys | Arg | Gly | |
| 250 | | | | | 255 | | | | | 260 | | | | | 265 | |
| CTA | CGC | TTT | GAG | GAA | GCC | CCA | GAT | TAC | ATG | TAT | CTG | AGG | CAG | CTA | TTC | 1107 |
| Leu | Arg | Phe | Glu | Glu | Ala | Pro | Asp | Tyr | Met | Tyr | Leu | Arg | Gln | Leu | Phe | |
| | | | | 270 | | | | | 275 | | | | | 280 | | |
| CGC | ATT | CTT | TTC | AGG | ACC | CTG | AAC | CAT | CAA | TAT | GAC | TAC | ACA | TTT | GAT | 1155 |
| Arg | Ile | Leu | Phe | Arg | Thr | Leu | Asn | His | Gln | Tyr | Asp | Tyr | Thr | Phe | Asp | |
| | | | 285 | | | | | 290 | | | | | 295 | | | |
| TGG | ACA | ATG | TTA | AAG | CAG | AAA | GCA | GCA | CAG | CAG | GCA | GCC | TCT | TCC | AGT | 1203 |
| Trp | Thr | Met | Leu | Lys | Gln | Lys | Ala | Ala | Gln | Gln | Ala | Ala | Ser | Ser | Ser | |
| | | 300 | | | | | 305 | | | | | 310 | | | | |
| GGG | CAG | GGT | CAG | CAG | GCC | CAA | ACC | CCC | ACA | GGC | AAG | CAA | ACT | GAC | AAA | 1251 |
| Gly | Gln | Gly | Gln | Gln | Ala | Gln | Thr | Pro | Thr | Gly | Lys | Gln | Thr | Asp | Lys | |
| | 315 | | | | | 320 | | | | | 325 | | | | | |
| ACC | AAG | AGT | AAC | ATG | AAA | GGT | TTC | TAAGCATGAA | TTGAGGAACA | GAAGAAGCAG | | | | | | 1305 |
| Thr | Lys | Ser | Asn | Met | Lys | Gly | Phe | | | | | | | | | |
| 330 | | | | | 335 | | | | | | | | | | | |

| | | | | |
|---|---|---|---|---|
| AGCAGATGAT | CGGAGCAGCA | TTTGTTTCTC | CCCAAATCTA | GAAATTTTAG TTCATATGTA | 1365 |
| CACTAGCCAG | TGGTTGTGGA | CAACCATTTA | CTTGGTGTAA | AGAACTTAAT TTCAGTATAA | 1425 |
| ACTGACTCTG | GGCAGCATTG | GTGATGCTGT | ATCCTGAGTT | GTAGCCTCTG TAATTGTGAA | 1485 |
| TATTAACTGA | GATAGTGAAA | CATGGTGTCC | GGTTTTCTAT | TGCATTTTTT CAAGTGGAAA | 1545 |
| AGTTAACTAA | ATGGTTGACA | CACAAAAATT | GGTGGAGAAA | TTGTGCATAT GCCAATTTTT | 1605 |
| TGTTAAAACC | TTTTGTTTTG | AACTATACTG | CTTTGAGATC | TCATTTCAGA AGAACGGCAT | 1665 |
| GAACAGTCTT | CAGCCACAGT | TGTGATGGTT | GTTAAATGCT | CACAATTGTG CATTCTTAGG | 1725 |
| GTTTTTCCAT | CCCTGGGGTT | TGCAAGTTGT | TCACTTAAAA | CATTCTTAAA ATGGTTGGCT | 1785 |
| TCTTGTCTGC | AAGCCAGCTG | ATATGGTAGC | AACCAAGAT | TCCAGTGTTT GAGCATATGA | 1845 |
| AAGACTCTGC | CTGCTTAATT | GTGCTAGAAA | TAACAGCATC | TAAAGTGAAG ACTTAAGAAA | 1905 |
| AACTTAGTGA | CTACTAGATT | ATCCTTAGGA | CTCTGCATTA | ACTCTATAAT GTTCTTGGTA | 1965 |
| TTAAAAAAAA | AGCATATTTG | TCACAGAAAT | TTAGTTAACA | TCTTACAACT GAACATGTAT | 2025 |
| GTATGTTGCT | TAGATAAATG | TAATCACTGT | AAACATCTAT | ATGATCTGGG ATTTTGTTTT | 2085 |
| TATTTTGAAA | TGGGAGCTTT | TTTGTTTACA | AGTTCATTAA | AAACTAAAAA CTGTTTCTGT | 2145 |

-continued

| | | | | | |
|---|---|---|---|---|---|
| AAGGAAATGA | GATTTTTTTT | AAACAACAAA | AAATGCCTTG | CTGACTCACT | ATTAAATAAA | 2205 |
| AATCTCCCCA | ATTTTTTGAT | AGACTACTTC | AAGCCATTTG | TTACATGGTA | TTCCTTTGCA | 2265 |
| AGTCAATTTA | GGTTTCGTGT | TATAACTTTT | CCTCTTTTTT | TAAGAAAAAT | GAAAAAGTA | 2325 |
| ATTCTTTTGT | CTGAAGGGGA | AAGGCATTCT | TTCATTTTTT | TCTTTTTTTT | TTTTTTTTT | 2385 |
| TTATGACTTG | CAGGCACAAT | ATCTAGTACT | GCAACTGCCA | GAACTTGGTA | TTGTAGCTGC | 2445 |
| TGCCCGCTGA | CTAGCAGCTG | GACTGATTTT | GAATAAAAAT | GAAAGCAGTA | CTGGGATTAC | 2505 |
| AGGTGAGCCA | CAGTGCCTGG | CCCTTTTTTG | TTTTATTGT | CTGTCTCCCC | ACTAGAAGGT | 2565 |
| ACGCTCTACA | AGGGCAGGGA | TTTGTGCATC | TTATTCATAG | TGTTTCCCAC | GTGGCAGATG | 2625 |
| CTCACTAAAG | ATTTCAAAGG | AGAAACTGTG | ATGGACTCGT | TCTGTAGATG | AGAGAACAGA | 2685 |
| GGCACAGAGA | CCTGTCCATG | GTCCCTGGC | AGAAGGAGGT | GGGGTCTGGA | TTCCACCCCA | 2745 |
| GGGCTGCGTG | GCTGCAGGAC | CTCAGTGCTT | GACTCCACAC | TGCTGAGGGC | TGTGAGTCCC | 2805 |
| TGGCCAGCCC | AGACACAGTC | CTGCAGCCCA | GGCTGAGCAT | TCTCAGACCT | TCATGGAGAT | 2865 |
| GCCCACTCTC | CTGTGAGCCT | CCTGCTTCCT | TTGCCCAGGG | CCGGAATTC | | 2914 |

(2) INFORMATION FOR SEQ ID NO:12:

(i) SEQUENCE CHARACTERISTICS:
      (A) LENGTH: 337 amino acids
      (B) TYPE: amino acid
      (D) TOPOLOGY: linear (ii) MOLECULE TYPE: protein (xi) SEQUENCE DESCRIPTION: SEQ ID NO:12:

```
Met Ala Ser Ser Ser Gly Ser Lys Ala Glu Phe Ile Val Gly Gly Lys
 1               5                  10                  15

Tyr Lys Leu Val Arg Lys Ile Gly Ser Gly Ser Phe Gly Asp Ile Tyr
                20                  25                  30

Leu Ala Ile Asn Ile Thr Asn Gly Glu Glu Val Ala Val Lys Leu Glu
            35                  40                  45

Ser Gln Lys Ala Arg His Pro Gln Leu Leu Tyr Glu Ser Lys Leu Tyr
        50                  55                  60

Lys Ile Leu Gln Gly Gly Val Gly Ile Pro His Ile Arg Trp Tyr Gly
65                  70                  75                  80

Gln Glu Lys Asp Tyr Asn Val Leu Val Met Asp Leu Leu Gly Pro Ser
                85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
        115                 120                 125

Thr Lys Asn Phe Ile His Arg Asp Ile Lys Pro Asp Asn Phe Leu Met
    130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                165                 170                 175

Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
        195                 200                 205

Tyr Val Leu Met Tyr Phe Asn Arg Thr Ser Leu Pro Trp Gln Gly Leu
    210                 215                 220
```

| Lys 225 | Ala | Ala | Thr | Lys 230 | Lys | Gln | Lys | Tyr | Glu 235 | Lys | Ile | Ser | Glu | Lys 240 |
| Met | Ser | Thr | Pro | Val 245 | Glu | Val | Leu | Cys | Lys 250 | Gly | Phe | Pro | Ala | Phe 255 |
| Ala | Met | Tyr | Leu 260 | Asn | Tyr | Cys | Arg | Gly 265 | Leu | Arg | Phe | Glu | Glu 270 | Ala | Pro |
| Asp | Tyr | Met 275 | Tyr | Leu | Arg | Gln | Leu 280 | Phe | Arg | Ile | Leu | Phe 285 | Arg | Thr | Leu |
| Asn | His 290 | Gln | Tyr | Asp | Tyr | Thr 295 | Phe | Asp | Trp | Thr | Met 300 | Leu | Lys | Gln | Lys |
| Ala 305 | Ala | Gln | Gln | Ala | Ala 310 | Ser | Ser | Ser | Gly | Gln 315 | Gly | Gln | Gln | Ala | Gln 320 |
| Thr | Pro | Thr | Gly | Lys 325 | Gln | Thr | Asp | Lys | Thr 330 | Lys | Ser | Asn | Met | Lys 335 | Gly |

Phe ( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 1..23
        ( D ) OTHER INFORMATION: /note= "Bases designated N at
            positions 3, 6, 9, 12 and 18 are Inosine."

( x i ) SEQUENCE DESCRIPTION: SEQ ID NO:13:

GGNWSNGGNW SNTT Y GGNGA Y AT      23

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 1..23
        ( D ) OTHER INFORMATION: /note= "Bases designated N at
            positions 6, 12 and 18 are Inosine."

( x i ) SEQUENCE DESCRIPTION: SEQ ID NO:14:

CA Y GMNGA Y A TNAARCCN-
GA Y AA      23

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i i  ) MOLECULE TYPE: DNA (genomic)

(  v i i  ) IMMEDIATE SOURCE:
    ( B ) CLONE: Protein Kinase (  i x  ) FEATURE:
    ( A ) NAME/KEY: CDS
    ( B ) LOCATION: 1..24
    ( D ) OTHER INFORMATION: /note= "Bases designated N at positions 7, 13 and 19 are Inosine."

(  x i  ) SEQUENCE DESCRIPTION: SEQ ID NO:15:

RTTRTCNGG Y TTNATRTCNC KRTG      24

( 2 ) INFORMATION FOR SEQ ID NO:16:

(  i  ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear (  i i  ) MOLECULE TYPE: DNA (genomic)

(  v i i  ) IMMEDIATE SOURCE:
    ( B ) CLONE: Protein Kinase (  i x  ) FEATURE:
    ( A ) NAME/KEY: CDS
    ( B ) LOCATION: 1..18
    ( D ) OTHER INFORMATION: /note= "Bases designated N at positions 1, 4, 7 and 13 are Inosine."

(  x i  ) SEQUENCE DESCRIPTION: SEQ ID NO:16:

NCCNARNSW Y TCNARRTC      18

( 2 ) INFORMATION FOR SEQ ID NO:17:

(  i  ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear (  i i  ) MOLECULE TYPE: DNA (genomic)

(  v i i  ) IMMEDIATE SOURCE:
    ( B ) CLONE: Protein Kinase (  i x  ) FEATURE:
    ( A ) NAME/KEY: CDS
    ( B ) LOCATION: 1..20

(  x i  ) SEQUENCE DESCRIPTION: SEQ ID NO:17:

ATATAAACTG GTACGGAAGA      20

( 2 ) INFORMATION FOR SEQ ID NO:18:

(  i  ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear (  i i  ) MOLECULE TYPE: DNA (genomic)

(  v i i  ) IMMEDIATE SOURCE:
    ( B ) CLONE: Protein Kinase (  i x  ) FEATURE:
    ( A ) NAME/KEY: CDS
    ( B ) LOCATION: 1..17

( x i ) SEQUENCE DESCRIPTION: SEQ ID NO:18:

ACATACGGTG GTATGGT                                                                                    17

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 1..19

( x i ) SEQUENCE DESCRIPTION: SEQ ID NO:19:

ATGACATGGA ATCATTAGG                                                                                  19

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 1..19

( x i ) SEQUENCE DESCRIPTION: SEQ ID NO:20:

CCTAATGATT CCATGTCAT                                                                                  19

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 1..18

( x i ) SEQUENCE DESCRIPTION: SEQ ID NO:21:

TCAGGTACAT GTAATCCG                                                                                   18

( 2 ) INFORMATION FOR SEQ ID NO:22:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
    ( B ) CLONE: Protein Kinase ( i x ) FEATURE:
    ( A ) NAME/KEY: CDS
    ( B ) LOCATION: 1..39

( x i ) SEQUENCE DESCRIPTION: SEQ ID NO:22:

```
CCTGATCGAT TCCAGCCTGA TCGCTACTTC TTCACCACT                                  39
```

( 2 ) INFORMATION FOR SEQ ID NO:23:

( i ) SEQUENCE CHARACTERISTICS:
        ( A ) LENGTH: 3627 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 1633..3204

( x i ) SEQUENCE DESCRIPTION: SEQ ID NO:23:

```
GATCAGATGA TATAGCTTTT TGTGTGCCGT ACCTTTCCGC GATTCTGCCC GTATATCTTG           60
GTCCCTGAGC TATTTCTGA  GATTCTTTTT GTTGCTTTGC CAAATCATTG GCGTCATTCA          120
TGGTCATACC AAATCCCAAT TTGGCAAACT GGGTGTTAA  AGTATCTTGC TGTTCTTTTC          180
TAGTTGTGTC GAAGCTGTTT GAAGTGTCAT TTAAAAAATC ATTGAATTCA TCAGGCTGGG          240
TATTAATATC ATCTATACTG TTATTATTGT TGCCTTTACT GTTATTCATA AATTGGGAAT          300
CGTAATCATT TGTCTAATTT TGGTGCTAGA AGACGAATTA GTGAACTCGT CCTCCTTTTC          360
TTGTTGAGCC TCTTTTTTAA ATTGATCAAA CAAGTCTTCT GCCTGTGATT TGTCGACTTT          420
CTTTGCGGTT AGTCTAGTGG GCTTTCTTGA CGAAGACAAA ATTGAATGTT TCTTTTTATC          480
TTGCGAGTTT AATACCGGTT TCTTTCTGCA TGCCGTTAAG ATGGAACTCT CGTTTAGTG           540
ACAGTGGTCT TGGGTGTGCT GCCTGTGGTG TTGTTTTTG  GGGCGAGAGA GCCTGTATTT          600
ACATTGAGTT TAGAACTGGA ATTGGAGCTT GGTTTTGCC  AATTAGAGAA AAAATCGTCA          660
ACACTATTTT CTTTGGAAGT CGACCTGGAA GCGTCTGAAT CGGTGTCCAA CGGTGAGTCC          720
GAAGAATCTT GACCGTTCAA GACTAATTCT GATGGGTATA ACTCCATATC CTTTTGAACC          780
TTCTTGTCGA GATGTATCTT ATATTTCTTA GCAACAGGGC TCGTATATTT TGTTTTCGCG          840
TCAACATTTG CTGTATTTAG TAGCTGTTTC CCATTGTTCT TTAAGAAAAA ATCACGAGCC          900
TTATGGTTCC CACCCAACTT AAACCTTCTT AAATTGTTAA TTGTCCATTT ATCTAATGTA          960
GAAGACTTTA CAAAGGTGAT ATGAACACCC ATGTTCTAT  GCACAGCAGA GCATTGAATA         1020
CACAGCATCA CACCAAAAGG TACCGAAGTC CAGTAGGATT CTTGTTACCA CAATCAAAAC         1080
AAACTCGATT TTCCATGTTG CTACCTAGCT TCTGAAAAAC TTGTTGAGTA GTCTGTTCCG         1140
TGGCAAATGT TTCTCCTTCA TCGTTACTCA TTGTCGCTAT GTGTATACTA AATTGCTCAA         1200
GAAGACCGGA TCAACAAGTA CTTAACAAAT ACCCTTTCTT TGCTATCGCC TTGATCTCCT         1260
TTTATAAAAT GCCAGCTAAA TCGTGTTTAC GAAGAATAGT TGTTTTCTTT TTTTTTTTT          1320
TTTTTCGAAA CTTTACCGTG TCGTCGAAAA TGACCAAACG ATGTTACTTT TCCTTTTGTG         1380
TCATAGATAA TACCAATATT GAAAGTAAAA TTTTAAACAT TCTATAGGTG AATTGAAAAG         1440
```

```
GGCAGCTTAG AGAGTAACAG GGGAACAGCA TTCGTAACAT CTAGGTACTG GTATTATTTG      1500

CTGTTTTTTA AAAAGAAGG  AAATCCGTTT TGCAAGAATT GTCTGCTATT TAAGGGTATA      1560

CGTGCTACGG TCCACTAATC AAAAGTGGTA TCTCATTCTG AAGAAAAAGT GTAAAAGGA       1620

CGATAAGGAA AG ATG TCC CAA CGA TCT TCA CAA CAC ATT GTA GGT ATT          1668
              Met Ser Gln Arg Ser Ser Gln His Ile Val Gly Ile
              1               5                   10

CAT TAT GCT GTA GGA CCT AAG ATT GGC GAA GGG TCT TTC GGA GTA ATA        1716
His Tyr Ala Val Gly Pro Lys Ile Gly Glu Gly Ser Phe Gly Val Ile
            15              20                  25

TTT GAG GGA GAG AAC ATT CTT CAT TCT TGT CAA GCG CAG ACC GGT AGC        1764
Phe Glu Gly Glu Asn Ile Leu His Ser Cys Gln Ala Gln Thr Gly Ser
    30              35                  40

AAG AGG GAC TCT AGT ATA ATA ATG GCG AAC GAG CCA GTC GCA ATT AAA        1812
Lys Arg Asp Ser Ser Ile Ile Met Ala Asn Glu Pro Val Ala Ile Lys
45              50                  55                      60

TTC GAA CCG CGA CAT TCG GAC GCA CCC CAG TTG CGT GAC GAA TTT AGA        1860
Phe Glu Pro Arg His Ser Asp Ala Pro Gln Leu Arg Asp Glu Phe Arg
                65                  70                  75

GCC TAT AGG ATA TTG AAT GGC TGC GTT GGA ATT CCC CAT GCT TAT TAT        1908
Ala Tyr Arg Ile Leu Asn Gly Cys Val Gly Ile Pro His Ala Tyr Tyr
            80                  85                  90

TTT GGT CAA GAA GGT ATG CAC AAC ATC TTG ATT ATC GAT TTA CTA GGG        1956
Phe Gly Gln Glu Gly Met His Asn Ile Leu Ile Ile Asp Leu Leu Gly
    95              100                 105

CCA TCA TTG GAA GAT CTC TTT GAG TGG TGT GGT AGA AAA TTT TCA GTG        2004
Pro Ser Leu Glu Asp Leu Phe Glu Trp Cys Gly Arg Lys Phe Ser Val
110             115                 120

AAA ACA ACC TGT ATG GTT GCC AAG CAA ATG ATT GAT AGA GTT AGA GCA        2052
Lys Thr Thr Cys Met Val Ala Lys Gln Met Ile Asp Arg Val Arg Ala
125             130                 135                     140

ATT CAT GAT CAC GAC TTA ATC TAT CGC GAT ATT AAA CCC GAT AAC TTT        2100
Ile His Asp His Asp Leu Ile Tyr Arg Asp Ile Lys Pro Asp Asn Phe
                145                 150                 155

TTA ATT TCT CAA TAT CAA AGA ATT TCA CCT GAA GGA AAA GTC ATT AAA        2148
Leu Ile Ser Gln Tyr Gln Arg Ile Ser Pro Glu Gly Lys Val Ile Lys
            160                 165                 170

TCA TGT GCC TCC TCT TCT AAT AAT GAT CCC AAT TTA ATA TAC ATG GTT        2196
Ser Cys Ala Ser Ser Ser Asn Asn Asp Pro Asn Leu Ile Tyr Met Val
    175             180                 185

GAC TTT GGT ATG GCA AAA CAA TAT AGA GAT CCA AGA ACG AAA CAA CAT        2244
Asp Phe Gly Met Ala Lys Gln Tyr Arg Asp Pro Arg Thr Lys Gln His
190             195                 200

ATA CCA TAC CGT GAA CGA AAA TCA TTG AGC GGT ACC GCC AGA TAT ATG        2292
Ile Pro Tyr Arg Glu Arg Lys Ser Leu Ser Gly Thr Ala Arg Tyr Met
205             210                 215                     220

TCT ATT AAT ACT CAT TTT GGA AGA GAA CAG TCA CGT AGG GAT GAT TTA        2340
Ser Ile Asn Thr His Phe Gly Arg Glu Gln Ser Arg Arg Asp Asp Leu
                225                 230                 235

GAA TCG CTA GGT CAC GTT TTT TTT TAT TTC TTG AGG GGA TCC TTG CCA        2388
Glu Ser Leu Gly His Val Phe Phe Tyr Phe Leu Arg Gly Ser Leu Pro
            240                 245                 250

TGG CAA GGT TTG AAA GCA CCA AAC AAC AAA CTG AAG TAT GAA AAG ATT        2436
Trp Gln Gly Leu Lys Ala Pro Asn Asn Lys Leu Lys Tyr Glu Lys Ile
    255             260                 265

GGT ATG ACT AAA CAG AAA TTG AAT CCT GAT GAT CTT TTA TTG AAT AAT        2484
Gly Met Thr Lys Gln Lys Leu Asn Pro Asp Asp Leu Leu Leu Asn Asn
270             275                 280

GCT ATT CCT TAT CAG TTT GCC ACA TAT TTA AAA TAT GCA CGT TCC TTG        2532
Ala Ile Pro Tyr Gln Phe Ala Thr Tyr Leu Lys Tyr Ala Arg Ser Leu
```

-continued

| | | | | | | | | | | | | | | | | |
|---|---|---|---|---|---|---|---|---|---|---|---|---|---|---|---|---|
| 285 | | | | | 290 | | | | | 295 | | | | | 300 | |
| AAG | TTC | GAC | GAA | GAT | CCG | GAT | TAT | GAC | TAT | TTA | ATC | TCG | TTA | ATG | GAT | 2580 |
| Lys | Phe | Asp | Glu | Asp 305 | Pro | Asp | Tyr | Asp | Tyr 310 | Leu | Ile | Ser | Leu | Met 315 | Asp | |
| GAC | GCT | TTG | AGA | TTA | AAC | GAC | TTA | AAG | GAT | GAT | GGA | CAC | TAT | GAC | TGG | 2628 |
| Asp | Ala | Leu | Arg 320 | Leu | Asn | Asp | Leu | Lys 325 | Asp | Asp | Gly | His | Tyr 330 | Asp | Trp | |
| ATG | GAT | TTG | AAT | GGT | GGT | AAA | GGC | TGG | AAT | ATC | AAG | ATT | AAT | AGA | AGA | 2676 |
| Met | Asp | Leu 335 | Asn | Gly | Gly | Lys | Gly 340 | Trp | Asn | Ile | Lys | Ile 345 | Asn | Arg | Arg | |
| GCT | AAC | TTG | CAT | GGT | TAC | GGA | AAT | CCA | AAT | CCA | AGA | GTC | AAT | GGC | AAT | 2724 |
| Ala | Asn 350 | Leu | His | Gly | Tyr | Gly 355 | Asn | Pro | Asn | Pro | Arg 360 | Val | Asn | Gly | Asn | |
| ACT | GCA | AGA | AAC | AAT | GTG | AAT | ACG | AAT | TCA | AAG | ACA | CGA | AAT | ACA | ACG | 2772 |
| Thr 365 | Ala | Arg | Asn | Asn | Val 370 | Asn | Thr | Asn | Ser | Lys 375 | Thr | Arg | Asn | Thr | Thr 380 | |
| CCA | GTT | GCG | ACA | CCT | AAG | CAA | CAA | GCT | CAA | AAC | AGT | TAT | AAC | AAG | GAC | 2820 |
| Pro | Val | Ala | Thr | Pro 385 | Lys | Gln | Gln | Ala | Gln 390 | Asn | Ser | Tyr | Asn | Lys 395 | Asp | |
| AAT | TCG | AAA | TCC | AGA | ATT | TCT | TCG | AAC | CCG | CAG | AGC | TTT | ACT | AAA | CAA | 2868 |
| Asn | Ser | Lys | Ser 400 | Arg | Ile | Ser | Ser | Asn 405 | Pro | Gln | Ser | Phe | Thr 410 | Lys | Gln | |
| CAA | CAC | GTC | TTG | AAA | AAA | ATC | GAA | CCC | AAT | AGT | AAA | TAT | ATT | CCT | GAA | 2916 |
| Gln | His | Val 415 | Leu | Lys | Lys | Ile | Glu 420 | Pro | Asn | Ser | Lys | Tyr 425 | Ile | Pro | Glu | |
| ACA | CAT | TCA | AAT | CTT | CAA | CGG | CCA | ATT | AAA | AGT | CAA | AGT | CAA | ACG | TAC | 2964 |
| Thr | His 430 | Ser | Asn | Leu | Gln | Arg 435 | Pro | Ile | Lys | Ser | Gln 440 | Ser | Gln | Thr | Tyr | |
| GAC | TCC | ATC | AGT | CAT | ACA | CAA | AAT | TCA | CCA | TTT | GTA | CCA | TAT | TCA | AGT | 3012 |
| Asp | Ser | Ile | Ser 445 | His | Thr | Gln | Asn | Ser 450 | Pro | Phe | Val | Pro 455 | Tyr | Ser | Ser 460 | |
| TCT | AAA | GCT | AAC | CCT | AAA | AGA | AGT | AAT | AAT | GAG | CAC | AAC | TTA | CCA | AAC | 3060 |
| Ser | Lys | Ala | Asn | Pro 465 | Lys | Arg | Ser | Asn | Asn 470 | Glu | His | Asn | Leu | Pro 475 | Asn | |
| CAC | TAC | ACA | AAC | CTT | GCA | AAT | AAG | AAT | ATC | AAT | TAT | CAA | AGT | CAA | CGA | 3108 |
| His | Tyr | Thr | Asn 480 | Leu | Ala | Asn | Lys | Asn 485 | Ile | Asn | Tyr | Gln | Ser 490 | Gln | Arg | |
| AAT | TAC | GAA | CAA | GAA | AAT | GAT | GCT | TAT | TCT | GAT | GAC | GAG | AAT | GAT | ACA | 3156 |
| Asn | Tyr | Glu | Gln 495 | Glu | Asn | Asp | Ala | Tyr 500 | Ser | Asp | Asp | Glu | Asn 505 | Asp | Thr | |
| TTT | TGT | TCT | AAA | ATA | TAC | AAA | TAT | TGT | TGT | TGC | TGT | TTT | TGT | TGC | TGT | 3204 |
| Phe | Cys 510 | Ser | Lys | Ile | Tyr | Lys 515 | Tyr | Cys | Cys | Cys | Cys 520 | Phe | Cys | Cys | Cys | |

| | | | |
|---|---|---|---|
| TGATAAAGCG | ATTTTATAC | TTTTCTCTTT | TTCCTTTTTT TTTTTGATTG GCTGTTTCCT | 3264 |
| TATGCCGCTC | TTTCCCAATT | TATGACTTTC | CAATAATGTA TTATTTTGTT TCTCTTTCTC | 3324 |
| TCTGTTACCC | TTTATTTTAT | CATCTACAAT | AATTGAATTC CGGAGAGGGT AAAGAAACAG | 3384 |
| GAAAAGAAG | AAAATGAGAC | ATAGTCAGCA | TCGTAATCGT TTTCCTTCTG TATATTCCTT | 3444 |
| TATCAAAAGA | CTACACGCAC | ATATATATTA | ATCCGGTAT GTTTTGGTG TGCTAAATCT | 3504 |
| ATCTTCAAGC | ACTATTATAG | CATTTTTTA | AGAATATCCA AAATAATATG TAATTTATGA | 3564 |
| TTAATCAAGG | TTCAAGAATT | GGAGAAACCG | TGAGCGACTT CTTTGATACT TGGATGTAAG | 3624 |
| CTT | | | | 3627 |

(2) INFORMATION FOR SEQ ID NO:24:

(i) SEQUENCE CHARACTERISTICS:
(A) LENGTH: 524 amino acids
(B) TYPE: amino acid ( D ) TOPOLOGY: linear ( i i ) MOLECULE TYPE: protein ( x i ) SEQUENCE DESCRIPTION: SEQ ID NO:24:

```
Met Ser Gln Arg Ser Ser Gln His Ile Val Gly Ile His Tyr Ala Val
  1               5                  10                 15

Gly Pro Lys Ile Gly Glu Gly Ser Phe Gly Val Ile Phe Glu Gly Glu
             20              25                 30

Asn Ile Leu His Ser Cys Gln Ala Gln Thr Gly Ser Lys Arg Asp Ser
             35              40              45

Ser Ile Ile Met Ala Asn Glu Pro Val Ala Ile Lys Phe Glu Pro Arg
         50              55              60

His Ser Asp Ala Pro Gln Leu Arg Asp Glu Phe Arg Ala Tyr Arg Ile
 65              70              75              80

Leu Asn Gly Cys Val Gly Ile Pro His Ala Tyr Tyr Phe Gly Gln Glu
                 85              90                 95

Gly Met His Asn Ile Leu Ile Ile Asp Leu Leu Gly Pro Ser Leu Glu
             100             105             110

Asp Leu Phe Glu Trp Cys Gly Arg Lys Phe Ser Val Lys Thr Thr Cys
         115             120             125

Met Val Ala Lys Gln Met Ile Asp Arg Val Arg Ala Ile His Asp His
     130             135             140

Asp Leu Ile Tyr Arg Asp Ile Lys Pro Asp Asn Phe Leu Ile Ser Gln
145             150             155             160

Tyr Gln Arg Ile Ser Pro Glu Gly Lys Val Ile Lys Ser Cys Ala Ser
             165             170             175

Ser Ser Asn Asn Asp Pro Asn Leu Ile Tyr Met Val Asp Phe Gly Met
             180             185             190

Ala Lys Gln Tyr Arg Asp Pro Arg Thr Lys Gln His Ile Pro Tyr Arg
         195             200             205

Glu Arg Lys Ser Leu Ser Gly Thr Ala Arg Tyr Met Ser Ile Asn Thr
     210             215             220

His Phe Gly Arg Glu Gln Ser Arg Arg Asp Asp Leu Glu Ser Leu Gly
225             230             235             240

His Val Phe Phe Tyr Phe Leu Arg Gly Ser Leu Pro Trp Gln Gly Leu
                 245             250             255

Lys Ala Pro Asn Asn Lys Leu Lys Tyr Glu Lys Ile Gly Met Thr Lys
             260             265             270

Gln Lys Leu Asn Pro Asp Asp Leu Leu Asn Asn Ala Ile Pro Tyr
         275             280             285

Gln Phe Ala Thr Tyr Leu Lys Tyr Ala Arg Ser Leu Lys Phe Asp Glu
     290             295             300

Asp Pro Asp Tyr Asp Tyr Leu Ile Ser Leu Met Asp Asp Ala Leu Arg
305             310             315             320

Leu Asn Asp Leu Lys Asp Asp Gly His Tyr Asp Trp Met Asp Leu Asn
             325             330             335

Gly Gly Lys Gly Trp Asn Ile Lys Ile Asn Arg Arg Ala Asn Leu His
             340             345             350

Gly Tyr Gly Asn Pro Asn Pro Arg Val Asn Gly Asn Thr Ala Arg Asn
         355             360             365

Asn Val Asn Thr Asn Ser Lys Thr Arg Asn Thr Thr Pro Val Ala Thr
     370             375             380

Pro Lys Gln Gln Ala Gln Asn Ser Tyr Asn Lys Asp Asn Ser Lys Ser
385             390             395             400
```

-continued

```
Arg  Ile  Ser  Ser  Asn  Pro  Gln  Ser  Phe  Thr  Lys  Gln  Gln  His  Val  Leu
               405                      410                      415

Lys  Lys  Ile  Glu  Pro  Asn  Ser  Lys  Tyr  Ile  Pro  Glu  Thr  His  Ser  Asn
               420                      425                      430

Leu  Gln  Arg  Pro  Ile  Lys  Ser  Gln  Ser  Gln  Thr  Tyr  Asp  Ser  Ile  Ser
               435                      440                      445

His  Thr  Gln  Asn  Ser  Pro  Phe  Val  Pro  Tyr  Ser  Ser  Ser  Lys  Ala  Asn
          450                      455                      460

Pro  Lys  Arg  Ser  Asn  Asn  Glu  His  Asn  Leu  Pro  Asn  His  Tyr  Thr  Asn
465                           470                      475                      480

Leu  Ala  Asn  Lys  Asn  Ile  Asn  Tyr  Gln  Ser  Gln  Arg  Asn  Tyr  Glu  Gln
                    485                      490                      495

Glu  Asn  Asp  Ala  Tyr  Ser  Asp  Asp  Glu  Asn  Asp  Thr  Phe  Cys  Ser  Lys
                    500                      505                      510

Ile  Tyr  Lys  Tyr  Cys  Cys  Cys  Cys  Phe  Cys  Cys  Cys
               515                      520
```

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: Protein Kinase ( i x ) FEATURE:
        ( A ) NAME/KEY: Peptide
        ( B ) LOCATION: 1..6

( x i ) SEQUENCE DESCRIPTION: SEQ ID NO:25:

```
Gly  Pro  Ser  Leu  Glu  Asp
 1                    5
```

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: Protein Kinase ( i x ) FEATURE:
        ( A ) NAME/KEY: Peptide
        ( B ) LOCATION: 1..9

( x i ) SEQUENCE DESCRIPTION: SEQ ID NO:26:

```
Arg  Asp  Ile  Lys  Pro  Asp  Asn  Phe  Leu
 1                    5
```

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
            ( B ) CLONE: Protein Kinase ( i x ) FEATURE:
            ( A ) NAME/KEY: Peptide
            ( B ) LOCATION: 1..6

( x i ) SEQUENCE DESCRIPTION: SEQ ID NO:27:

His Ile Pro Tyr Arg Glu
1               5

( 2 ) INFORMATION FOR SEQ ID NO:28:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: Modified-site
            ( B ) LOCATION: 6
            ( C ) OTHER INFORMATION: /note= "The nucleotide at this position
                    is inosine."

( i x ) FEATURE:
            ( A ) NAME/KEY: Modified-site
            ( B ) LOCATION: 9
            ( C ) OTHER INFORMATION: /note= "The nucleotide at this position
                    is inosine."

( i x ) FEATURE:
            ( A ) NAME/KEY: Modified-site
            ( B ) LOCATION: 12
            ( C ) OTHER INFORMATION: /note= "The nucleotide at this position
                    is inosine."

( i x ) FEATURE:
            ( A ) NAME/KEY: Modified-site
            ( B ) LOCATION: 15
            ( C ) OTHER INFORMATION: /note= "The nucleotide at this position
                    is inosine."

( i x ) FEATURE:
            ( A ) NAME/KEY: Modified-site
            ( B ) LOCATION: 21
            ( C ) OTHER INFORMATION: /note= "The nucleotide at this position
                    is inosine."

( x i ) SEQUENCE DESCRIPTION: SEQ ID NO:28:

GAR Y TNMGN Y TNG-
GNAA Y YT N                                                                                21

( 2 ) INFORMATION FOR SEQ ID NO:29:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: Modified-site
            ( B ) LOCATION: 9
            ( C ) OTHER INFORMATION: /note= "The nucleotide at this position
                    is inosine."

( i x ) FEATURE:
            ( A ) NAME/KEY: Modified-site
            ( B ) LOCATION: 12

( C ) OTHER INFORMATION: /note= "The nucleotide at this position is inosine."

( i x ) FEATURE:
  ( A ) NAME/KEY: Modified-site
  ( B ) LOCATION: 15
  ( C ) OTHER INFORMATION: /note= "The nucleotide at this position is inosine."

( i x ) FEATURE:
  ( A ) NAME/KEY: Modified-site
  ( B ) LOCATION: 18
  ( C ) OTHER INFORMATION: /note= "The nucleotide at this position is inosine."

( i x ) FEATURE:
  ( A ) NAME/KEY: Modified-site
  ( B ) LOCATION: 21
  ( C ) OTHER INFORMATION: /note= "The nucleotide at this position is inosine."

( x i ) SEQUENCE DESCRIPTION: SEQ ID NO:29:

GT Y TTRTTNC CNGGNCKNCC NAT     23

( 2 ) INFORMATION FOR SEQ ID NO:30:

( i ) SEQUENCE CHARACTERISTICS:
    ( A ) LENGTH: 2405 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 67..1197

( x i ) SEQUENCE DESCRIPTION: SEQ ID NO:30:

```
AAAGTGGAGT ACCGCAAACT TGATATGGAA AATAAAAAGA AAGACAAGGA CAAATCAGAT          60

GATAGA ATG GCA CGA CCT AGT GGT CGA TCG GGA CAC AAC ACT CGA GGA           108
       Met Ala Arg Pro Ser Gly Arg Ser Gly His Asn Thr Arg Gly
        1           5                          10

ACT GGG TCT TCA TCG TCT GGA GTT TTA ATG GTT GGA CCT AAC TTT AGA          156
Thr Gly Ser Ser Ser Ser Gly Val Leu Met Val Gly Pro Asn Phe Arg
 15              20                  25                      30

GTT GGA AAA AAA ATT GGA TGT GGC AAT TTT GGA GAA TTA CGA TTA GGG          204
Val Gly Lys Lys Ile Gly Cys Gly Asn Phe Gly Glu Leu Arg Leu Gly
                 35                  40                  45

AAA AAT TTA TAC ACA AAT GAA TAT GTG GCA ATT AAG TTG GAG CCC ATG          252
Lys Asn Leu Tyr Thr Asn Glu Tyr Val Ala Ile Lys Leu Glu Pro Met
             50                  55                  60

AAA TCA AGA GCA CCA CAG CTA CAT TTG GAA TAC AGA TTC TAT AAG CAG          300
Lys Ser Arg Ala Pro Gln Leu His Leu Glu Tyr Arg Phe Tyr Lys Gln
         65                  70                  75

TTA GGA TCT GGA GAT GGT ATA CCT CAA GTT TAC TAT TTC GGC CCC TGT          348
Leu Gly Ser Gly Asp Gly Ile Pro Gln Val Tyr Tyr Phe Gly Pro Cys
     80                  85                  90

GGT AAA TAC AAT GCT ATG GTG CTG GAA CTG CTG GGA CCT AGT TTG GAA          396
Gly Lys Tyr Asn Ala Met Val Leu Glu Leu Leu Gly Pro Ser Leu Glu
 95                 100                 105                 110

GAC TTG TTT GAC TTG TGT GAC AGA ACA TTT TCT CTT AAA ACA GTT CTC          444
Asp Leu Phe Asp Leu Cys Asp Arg Thr Phe Ser Leu Lys Thr Val Leu
                115                 120                 125

ATG ATA GCT ATA CAA CTG ATT TCT CGC ATG GAA TAT GTC CAT TCA AAG          492
Met Ile Ala Ile Gln Leu Ile Ser Arg Met Glu Tyr Val His Ser Lys
            130                 135                 140
```

```
AAC TTG ATA TAC AGA GAT GTA AAA CCT GAG AAC TTC TTA ATA GGA CGA        540
Asn Leu Ile Tyr Arg Asp Val Lys Pro Glu Asn Phe Leu Ile Gly Arg
        145                 150                 155

CCA GGA AAC AAA ACC CAG CAA GTT ATT CAC ATT ATA GAT TTT GGT TTG        588
Pro Gly Asn Lys Thr Gln Gln Val Ile His Ile Ile Asp Phe Gly Leu
160                 165                 170

GCA AAG GAA TAT ATT GAT CCG GAG ACA AAG AAA CAC ATA CCA TAC AGA        636
Ala Lys Glu Tyr Ile Asp Pro Glu Thr Lys Lys His Ile Pro Tyr Arg
175                 180                 185                 190

GAA CAC AAG AGC CTT ACA GGA ACA GCT AGA TAT ATG AGC ATA AAC ACA        684
Glu His Lys Ser Leu Thr Gly Thr Ala Arg Tyr Met Ser Ile Asn Thr
            195                 200                 205

CAT TTA GGA AAA GAA CAA AGT AGA AGA GAC GAT TTA GAA GCT TTA GGT        732
His Leu Gly Lys Glu Gln Ser Arg Arg Asp Asp Leu Glu Ala Leu Gly
            210                 215                 220

CAT ATG TTC ATG TAT TTT CTG AGA GGC AGT CTT CCT TGG CAA GGC TTA        780
His Met Phe Met Tyr Phe Leu Arg Gly Ser Leu Pro Trp Gln Gly Leu
        225                 230                 235

AAG GCT GAC ACA TTA AAG GAG AGG TAT CAG AAA ATT GGA GAT ACA AAA        828
Lys Ala Asp Thr Leu Lys Glu Arg Tyr Gln Lys Ile Gly Asp Thr Lys
        240                 245                 250

CGG GCT ACA CCA ATA GAA GTG TTA TGT GAA AAT TTT CCA GAA GAA ATG        876
Arg Ala Thr Pro Ile Glu Val Leu Cys Glu Asn Phe Pro Glu Glu Met
255                 260                 265                 270

GCA ACA TAT CTT CGT TAT GTA AGA AGG CTA GAT TTT TTT GAA AAA CCA        924
Ala Thr Tyr Leu Arg Tyr Val Arg Arg Leu Asp Phe Phe Glu Lys Pro
                275                 280                 285

GAC TAT GAC TAC TTA AGA AAG CTT TTT ACT GAC TTG TTT GAT CGA AAA        972
Asp Tyr Asp Tyr Leu Arg Lys Leu Phe Thr Asp Leu Phe Asp Arg Lys
                    290                 295                 300

GGA TAT ATG TTT GAT TAT GAA TAT GAC TGG ATT GGT AAA CAG TTG CCT       1020
Gly Tyr Met Phe Asp Tyr Glu Tyr Asp Trp Ile Gly Lys Gln Leu Pro
        305                 310                 315

ACT CCA GTG GGT GCA GTT CAG CAA GAT CCT GCT CTG TCA TCA AAC AGA       1068
Thr Pro Val Gly Ala Val Gln Gln Asp Pro Ala Leu Ser Ser Asn Arg
        320                 325                 330

GAA GCA CAT CAA CAC AGA GAT AAG ATG CAA CAA TCC AAA AAC CAG GTT       1116
Glu Ala His Gln His Arg Asp Lys Met Gln Gln Ser Lys Asn Gln Val
335                 340                 345                 350

GTA AGT TCT ACA AAT GGA GAG TTA AAC ACA GAT GAC CCC ACC GCA GAC       1164
Val Ser Ser Thr Asn Gly Glu Leu Asn Thr Asp Asp Pro Thr Ala Asp
                355                 360                 365

GTT CAA ATG CAC CCA TCA CAG CCC CTA CTG AAG TAGAAGTGAT GGATGAAACC     1217
Val Gln Met His Pro Ser Gln Pro Leu Leu Lys
                370                 375

AACTGCCAGA AAGTGTTGAA CATGTGGTGC TGCTGTTTTT TCAAACGAAG GAAAAGGAAA    1277

ACCATACAGC GCCACAAATG ACTCTGGACA CAGACAGATC CTGGGGAGTT ACTTACATGT    1337

TCATCTGCTG TCTTGTGATT AAAATCATCT CTGTAGTGAC CACGTATATT TTCAAGGACT    1397

CACTCTTAGA AACAAAAATG TCATACTTTC ATACTTCATT TTGTGGTTGT CTTACATTCT    1457

TTTTCTTTTT TTTTTCTCT AATTTAACCT TTATGGAAGC TTTAAAGTTT TGTCAAAAAC     1517

ATGAGTGCTT TTGCCCCATC AGTGAATGGA ATGGACCAAT GAGGTGGTAT CAATGAATAT    1577

AGTTCCATAG AACATTTCCA GAAGTTCTTC TGTTGTAGAA AGCAGTACAG TATCTTAAGT    1637

GTCAACCAGT TATATACCTA ATCTGGTTTT TTATAACTTC TGTAAGAGCA TAATCAAACA    1697

GGAATTTTCT TTTCTCAGTG GATAATACAA CAGAGAAAAC AGAGTTGCCC AAATATTTAA    1757

AAGAAGTTAT TCCTTGAGAA GTTCATATTT TGTGACATCT GCATTGATTT CAGTATTACT    1817
```

-continued

```
GATGGTACTG TTATTCATAA GTCATATTAA CATTCTCTCC GTGAAATCAT GGTACAGTCG    1877
CTGCCCAGAG GTACTGAGGA AAAAGCAATA TGGGTTCGGC AGATGGTGGT GGTAAAATGA    1937
ATCTTAAGGA GTGTGGTAAA TATGCGTCCG CTTTTGTTGC ATCACTATGT GAAGTACTGT    1997
GTTGCAGAAG TGGCAAAAGC GCTTATTTTT AAAAATGCAA AATATTTGTA CAATGTAACT    2057
TTATGCTTCC AAATAATAAT GTATGTTAGA CAGCAAGAAA TGAATACTTT AAAAAGTGAT    2117
GTATGTTGGA GTTATAAAGA ATACACTAA GGAGAGGTAG TAAATGTGAA CCTTGTTGCA     2177
GTGTATAAGG TGGAAGCCTA AAGAAATCTC ACCGAAACTT ACTGCTGAAT GATTACATTC    2237
TCCCTTAAGC AGAAAACTTT GGATGTGCCA TGCAATGGTG TCTGTGTAAT TATTTTGCTC    2297
TTTGATTAAA AAAAAGACCC CCAGCAATAA AAAGTGGGTC ACTCTAAAAA AAAAAAAAAA    2357
AAAAAAAAAA AAAAAAAAAA AAAAAAAAA ACGACAGCAA CGGAATTC                  2405
```

( 2 ) INFORMATION FOR SEQ ID NO:31:

( i ) SEQUENCE CHARACTERISTICS:
        ( A ) LENGTH: 377 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
Met Ala Arg Pro Ser Gly Arg Ser Gly His Asn Thr Arg Gly Thr Gly
  1               5                  10                  15
Ser Ser Ser Ser Gly Val Leu Met Val Gly Pro Asn Phe Arg Val Gly
             20                  25                  30
Lys Lys Ile Gly Cys Gly Asn Phe Gly Glu Leu Arg Leu Gly Lys Asn
         35                  40                  45
Leu Tyr Thr Asn Glu Tyr Val Ala Ile Lys Leu Glu Pro Met Lys Ser
 50                  55                  60
Arg Ala Pro Gln Leu His Leu Glu Tyr Arg Phe Tyr Lys Gln Leu Gly
 65                  70                  75                  80
Ser Gly Asp Gly Ile Pro Gln Val Tyr Tyr Phe Gly Pro Cys Gly Lys
                 85                  90                  95
Tyr Asn Ala Met Val Leu Glu Leu Leu Gly Pro Ser Leu Glu Asp Leu
            100                 105                 110
Phe Asp Leu Cys Asp Arg Thr Phe Ser Leu Lys Thr Val Leu Met Ile
        115                 120                 125
Ala Ile Gln Leu Ile Ser Arg Met Glu Tyr Val His Ser Lys Asn Leu
    130                 135                 140
Ile Tyr Arg Asp Val Lys Pro Glu Asn Phe Leu Ile Gly Arg Pro Gly
145                 150                 155                 160
Asn Lys Thr Gln Gln Val Ile His Ile Ile Asp Phe Gly Leu Ala Lys
                165                 170                 175
Glu Tyr Ile Asp Pro Glu Thr Lys Lys His Ile Pro Tyr Arg Glu His
            180                 185                 190
Lys Ser Leu Thr Gly Thr Ala Arg Tyr Met Ser Ile Asn Thr His Leu
        195                 200                 205
Gly Lys Glu Gln Ser Arg Arg Asp Asp Leu Glu Ala Leu Gly His Met
    210                 215                 220
Phe Met Tyr Phe Leu Arg Gly Ser Leu Pro Trp Gln Gly Leu Lys Ala
225                 230                 235                 240
Asp Thr Leu Lys Glu Arg Tyr Gln Lys Ile Gly Asp Thr Lys Arg Ala
                245                 250                 255
```

```
Thr Pro Ile Glu Val Leu Cys Glu Asn Phe Pro Glu Glu Met Ala Thr
            260                 265                 270

Tyr Leu Arg Tyr Val Arg Arg Leu Asp Phe Phe Glu Lys Pro Asp Tyr
            275                 280                 285

Asp Tyr Leu Arg Lys Leu Phe Thr Asp Leu Phe Asp Arg Lys Gly Tyr
        290                 295                 300

Met Phe Asp Tyr Glu Tyr Asp Trp Ile Gly Lys Gln Leu Pro Thr Pro
305                 310                 315                 320

Val Gly Ala Val Gln Gln Asp Pro Ala Leu Ser Ser Asn Arg Glu Ala
                325                 330                 335

His Gln His Arg Asp Lys Met Gln Gln Ser Lys Asn Gln Val Val Ser
            340                 345                 350

Ser Thr Asn Gly Glu Leu Asn Thr Asp Asp Pro Thr Ala Asp Val Gln
        355                 360                 365

Met His Pro Ser Gln Pro Leu Leu Lys
370                 375
```

( 2 ) INFORMATION FOR SEQ ID NO:32:

( i ) SEQUENCE CHARACTERISTICS:
        ( A ) LENGTH: 1233 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1041

( x i ) SEQUENCE DESCRIPTION: SEQ ID NO:32:

```
AGA GTT GGA AAA AAA ATT GGA TGT GGC AAT TTT GGA GAA TTA CGA TTA        48
Arg Val Gly Lys Lys Ile Gly Cys Gly Asn Phe Gly Glu Leu Arg Leu
  1               5                  10                  15

GGG AAA AAT TTA TAC ACA AAT GAA TAT GTG GCA ATT AAG TTG GAG CCC        96
Gly Lys Asn Leu Tyr Thr Asn Glu Tyr Val Ala Ile Lys Leu Glu Pro
            20                  25                  30

ATG AAA TCA AGA GCA CCA CAG CTA CAT TTG GAA TAC AGA TTC TAT AAG       144
Met Lys Ser Arg Ala Pro Gln Leu His Leu Glu Tyr Arg Phe Tyr Lys
        35                  40                  45

CAG TTA GGA TCT GGA GAT GGT ATA CCT CAA GTT TAC TAT TTC GGC CCT       192
Gln Leu Gly Ser Gly Asp Gly Ile Pro Gln Val Tyr Tyr Phe Gly Pro
    50                  55                  60

TGT GGT AAA TAC AAT GCT ATG GTG CTG GAA CTG CTG GGA CCT AGT TTG       240
Cys Gly Lys Tyr Asn Ala Met Val Leu Glu Leu Leu Gly Pro Ser Leu
 65                  70                  75                  80

GAA GAC TTG TTT GAC TTG TGT GAC AGA ACA TTT TCT CTT AAA ACA GTT       288
Glu Asp Leu Phe Asp Leu Cys Asp Arg Thr Phe Ser Leu Lys Thr Val
                 85                  90                  95

CTC ATG ATA GCT ATA CAA CTG ATT TCT CGC ATG GAA TAT GTC CAT TCA       336
Leu Met Ile Ala Ile Gln Leu Ile Ser Arg Met Glu Tyr Val His Ser
            100                 105                 110

AAG AAC TTG ATA TAC AGA GAT GTA AAA CCT GAG AAC TTC TTA ATA GGA       384
Lys Asn Leu Ile Tyr Arg Asp Val Lys Pro Glu Asn Phe Leu Ile Gly
        115                 120                 125

CGA CCA GGA AAC AAA ACC CAG CAA GTT ATT CAC ATT ATA GAT TTT GGT       432
Arg Pro Gly Asn Lys Thr Gln Gln Val Ile His Ile Ile Asp Phe Gly
    130                 135                 140

TTG GCA AAG GAA TAT ATT GAT CCG GAG ACA AAG AAA CAC ATA CCA TAC       480
Leu Ala Lys Glu Tyr Ile Asp Pro Glu Thr Lys Lys His Ile Pro Tyr
145                 150                 155                 160
```

-continued

| | | | | | | | | | | | | | | | | |
|---|---|---|---|---|---|---|---|---|---|---|---|---|---|---|---|---|
| AGA | GAA | CAC | AAG | AGC | CTT | ACA | GGA | ACA | GCT | AGA | TAT | ATG | AGC | ATA | AAC | 528 |
| Arg | Glu | His | Lys | Ser | Leu | Thr | Gly | Thr | Ala | Arg | Tyr | Met | Ser | Ile | Asn | |
| | | | | 165 | | | | 170 | | | | | | 175 | | |
| ACA | CAT | TTA | GGA | AAA | GAA | CAA | AGT | AGA | AGA | GAC | GAT | TTA | GAA | GCT | TTA | 576 |
| Thr | His | Leu | Gly | Lys | Glu | Gln | Ser | Arg | Arg | Asp | Asp | Leu | Glu | Ala | Leu | |
| | | | 180 | | | | | 185 | | | | | 190 | | | |
| GGT | CAT | ATG | TTC | ATG | TAT | TTT | CTG | AGA | GGC | AGT | CTT | CCT | TGG | CAA | GGC | 624 |
| Gly | His | Met | Phe | Met | Tyr | Phe | Leu | Arg | Gly | Ser | Leu | Pro | Trp | Gln | Gly | |
| | | 195 | | | | | 200 | | | | | 205 | | | | |
| TTA | AAG | GTT | GAC | ACA | TTA | AAG | GAG | AGG | TAT | CAG | AAA | ATT | GGA | GAT | ACA | 672 |
| Leu | Lys | Val | Asp | Thr | Leu | Lys | Glu | Arg | Tyr | Gln | Lys | Ile | Gly | Asp | Thr | |
| | 210 | | | | | 215 | | | | | 220 | | | | | |
| AAA | CGG | GCT | ACA | CCA | ATA | GAA | GTG | TTA | TGT | GAA | AAT | TTT | CCA | GAA | ATG | 720 |
| Lys | Arg | Ala | Thr | Pro | Ile | Glu | Val | Leu | Cys | Glu | Asn | Phe | Pro | Glu | Met | |
| 225 | | | | | 230 | | | | 235 | | | | | | 240 | |
| GCA | ACA | TAT | CTT | CGT | TAT | GTA | AGA | AGG | CTA | GAT | TTT | TTT | GAA | AAA | CCA | 768 |
| Ala | Thr | Tyr | Leu | Arg | Tyr | Val | Arg | Arg | Leu | Asp | Phe | Phe | Glu | Lys | Pro | |
| | | | | 245 | | | | | 250 | | | | | 255 | | |
| GAC | TAT | GAC | TAC | TTA | AGA | AAG | CTT | TTT | ACT | GAC | TTG | TTT | GAT | CGA | AAA | 816 |
| Asp | Tyr | Asp | Tyr | Leu | Arg | Lys | Leu | Phe | Thr | Asp | Leu | Phe | Asp | Arg | Lys | |
| | | | 260 | | | | | 265 | | | | | 270 | | | |
| GGA | TAT | ATG | TTT | GAT | TAT | GAA | TAT | GAC | TGG | ATT | GGT | AAA | CAG | TTG | CCT | 864 |
| Gly | Tyr | Met | Phe | Asp | Tyr | Glu | Tyr | Asp | Trp | Ile | Gly | Lys | Gln | Leu | Pro | |
| | | 275 | | | | | 280 | | | | | 285 | | | | |
| ACT | CCA | GTG | GGT | GCA | GTT | CAG | CAA | GAT | CCT | GCT | CTG | TCA | TCA | AAC | AGA | 912 |
| Thr | Pro | Val | Gly | Ala | Val | Gln | Gln | Asp | Pro | Ala | Leu | Ser | Ser | Asn | Arg | |
| | 290 | | | | | 295 | | | | | 300 | | | | | |
| GAA | GCA | CAT | CAA | CAC | AGA | GAT | AAG | ATG | CAA | CAA | TCC | AAA | AAC | CAG | GTT | 960 |
| Glu | Ala | His | Gln | His | Arg | Asp | Lys | Met | Gln | Gln | Ser | Lys | Asn | Gln | Val | |
| 305 | | | | | 310 | | | | 315 | | | | | | 320 | |
| GTA | AGT | TCT | ACA | AAT | GGA | GAG | TTA | AAC | ACA | GAT | GAC | CCC | ACC | GCA | GAC | 1008 |
| Val | Ser | Ser | Thr | Asn | Gly | Glu | Leu | Asn | Thr | Asp | Asp | Pro | Thr | Ala | Asp | |
| | | | | 325 | | | | | 330 | | | | | 335 | | |
| GTT | CAA | ATG | CAC | CCA | TCA | CAG | CCC | CTA | CTG | AAG | TAGAAGTGAT | | GGATGAAACC | | | 1061 |
| Val | Gln | Met | His | Pro | Ser | Gln | Pro | Leu | Leu | Lys | | | | | | |
| | | | 340 | | | | | 345 | | | | | | | | |

AACTGCCAGA AAGTGTTGAA CATGTGGTGC TGCTGTTTTT TCAAACGAAG GAAAAGGAAA 1121

ACCATACAGC GCCACAAATG ACTCTGGACA CAGACAGATC CTGGGGAGTT ACTTACATGT 1181

TCATCTGCTG TCTTGTGATT AAATCATCTC TGTAGTGACC ACGTATATTT TC 1233

( 2 ) INFORMATION FOR SEQ ID NO:33:

( i ) SEQUENCE CHARACTERISTICS:
        ( A ) LENGTH: 347 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| | | | | | | | | | | | | | | | |
|---|---|---|---|---|---|---|---|---|---|---|---|---|---|---|---|
| Arg | Val | Gly | Lys | Lys | Ile | Gly | Cys | Gly | Asn | Phe | Gly | Glu | Leu | Arg | Leu |
| 1 | | | | 5 | | | | | 10 | | | | | 15 | |
| Gly | Lys | Asn | Leu | Tyr | Thr | Asn | Glu | Tyr | Val | Ala | Ile | Lys | Leu | Glu | Pro |
| | | | 20 | | | | | 25 | | | | | 30 | | |
| Met | Lys | Ser | Arg | Ala | Pro | Gln | Leu | His | Leu | Glu | Tyr | Arg | Phe | Tyr | Lys |
| | | 35 | | | | | 40 | | | | | 45 | | | |
| Gln | Leu | Gly | Ser | Gly | Asp | Gly | Ile | Pro | Gln | Val | Tyr | Tyr | Phe | Gly | Pro |
| | 50 | | | | | 55 | | | | | 60 | | | | |
| Cys | Gly | Lys | Tyr | Asn | Ala | Met | Val | Leu | Glu | Leu | Leu | Gly | Pro | Ser | Leu |

```
        65                          70                          75                          80
Glu  Asp  Leu  Phe  Asp  Leu  Cys  Asp  Arg  Thr  Phe  Ser  Leu  Lys  Thr  Val
                    85                       90                      95

Leu  Met  Ile  Ala  Ile  Gln  Leu  Ile  Ser  Arg  Met  Glu  Tyr  Val  His  Ser
               100                      105                     110

Lys  Asn  Leu  Ile  Tyr  Arg  Asp  Val  Lys  Pro  Glu  Asn  Phe  Leu  Ile  Gly
          115                      120                     125

Arg  Pro  Gly  Asn  Lys  Thr  Gln  Gln  Val  Ile  His  Ile  Ile  Asp  Phe  Gly
     130                      135                     140

Leu  Ala  Lys  Glu  Tyr  Ile  Asp  Pro  Glu  Thr  Lys  Lys  His  Ile  Pro  Tyr
145                      150                     155                          160

Arg  Glu  His  Lys  Ser  Leu  Thr  Gly  Thr  Ala  Arg  Tyr  Met  Ser  Ile  Asn
                    165                     170                     175

Thr  His  Leu  Gly  Lys  Glu  Gln  Ser  Arg  Arg  Asp  Asp  Leu  Glu  Ala  Leu
               180                      185                     190

Gly  His  Met  Phe  Met  Tyr  Phe  Leu  Arg  Gly  Ser  Leu  Pro  Trp  Gln  Gly
          195                      200                     205

Leu  Lys  Val  Asp  Thr  Leu  Lys  Glu  Arg  Tyr  Gln  Lys  Ile  Gly  Asp  Thr
     210                      215                     220

Lys  Arg  Ala  Thr  Pro  Ile  Glu  Val  Leu  Cys  Glu  Asn  Phe  Pro  Glu  Met
225                      230                     235                          240

Ala  Thr  Tyr  Leu  Arg  Tyr  Val  Arg  Arg  Leu  Asp  Phe  Phe  Glu  Lys  Pro
                    245                     250                     255

Asp  Tyr  Asp  Tyr  Leu  Arg  Lys  Leu  Phe  Thr  Asp  Leu  Phe  Asp  Arg  Lys
               260                      265                     270

Gly  Tyr  Met  Phe  Asp  Tyr  Glu  Tyr  Asp  Trp  Ile  Gly  Lys  Gln  Leu  Pro
          275                      280                     285

Thr  Pro  Val  Gly  Ala  Val  Gln  Gln  Asp  Pro  Ala  Leu  Ser  Ser  Asn  Arg
     290                      295                     300

Glu  Ala  His  Gln  His  Arg  Asp  Lys  Met  Gln  Gln  Ser  Lys  Asn  Gln  Val
305                      310                     315                          320

Val  Ser  Ser  Thr  Asn  Gly  Glu  Leu  Asn  Thr  Asp  Asp  Pro  Thr  Ala  Asp
                    325                     330                     335

Val  Gln  Met  His  Pro  Ser  Gln  Pro  Leu  Leu  Lys
               340                      345
```

( 2 ) INFORMATION FOR SEQ ID NO:34:

( i ) SEQUENCE CHARACTERISTICS:
         ( A ) LENGTH: 3505 base pairs
         ( B ) TYPE: nucleic acid
         ( C ) STRANDEDNESS: single
         ( D ) TOPOLOGY: linear ( i i ) MOLECULE TYPE: cDNA ( i x ) FEATURE:
         ( A ) NAME/KEY: CDS
         ( B ) LOCATION: 154..1398

( x i ) SEQUENCE DESCRIPTION: SEQ ID NO:34:

```
GAATTCCGAC  AGGAAAGCGA  TGGTGAAAGC  GGGGCCGTGA  GGGGGGCGGA  GCCGGGAGCC         60

GGACCCGCAG  TAGCGGCAGC  AGCGGCGCCG  CCTCCCGGAG  TTCAGACCCA  GGAAGCGGCC        120

GGGAGGGCAG  GAGCGAATCG  GGCCGCCGCC  GCC ATG GAG CTG AGA GTC GGG AAC          174
                                       Met Glu Leu Arg Val Gly Asn
                                        1               5

AGG TAC CGG CTG GGC CGG AAG ATC GGC AGC GGC TCC TTC GGA GAC ATC              222
Arg Tyr Arg Leu Gly Arg Lys Ile Gly Ser Gly Ser Phe Gly Asp Ile
```

```
                 10                         15                           20
TAT  CTC  GGT  ACG  GAC  ATT  GCT  GCA  GGA  GAA  GAG  GTT  GCC  ATC  AAG  CTT        270
Tyr  Leu  Gly  Thr  Asp  Ile  Ala  Ala  Gly  Glu  Glu  Val  Ala  Ile  Lys  Leu
     25                       30                       35

GAA  TGT  GTC  AAA  ACC  AAA  CAC  CCT  CAG  CTC  CAC  ATT  GAG  AGC  AAA  ATC        318
Glu  Cys  Val  Lys  Thr  Lys  His  Pro  Gln  Leu  His  Ile  Glu  Ser  Lys  Ile
40                            45                       50                       55

TAC  AAG  ATG  ATG  CAG  GGA  GGA  GTG  GGC  ATC  CCC  ACC  ATC  AGA  TGG  TGC        366
Tyr  Lys  Met  Met  Gln  Gly  Gly  Val  Gly  Ile  Pro  Thr  Ile  Arg  Trp  Cys
                    60                       65                       70

GGG  GCA  GAG  GGG  GAC  TAC  AAC  GTC  ATG  GTG  ATG  GAG  CTG  CTG  GGG  CCA        414
Gly  Ala  Glu  Gly  Asp  Tyr  Asn  Val  Met  Val  Met  Glu  Leu  Leu  Gly  Pro
               75                       80                       85

AGC  CTG  GAG  GAC  CTC  TTC  AAC  TTC  TGC  TCC  AGG  AAA  TTC  AGC  CTC  AAA        462
Ser  Leu  Glu  Asp  Leu  Phe  Asn  Phe  Cys  Ser  Arg  Lys  Phe  Ser  Leu  Lys
          90                       95                      100

ACC  GTC  CTG  CTG  CTT  GCT  GAC  CAA  ATG  ATC  AGT  CGC  ATC  GAA  TAC  ATT        510
Thr  Val  Leu  Leu  Leu  Ala  Asp  Gln  Met  Ile  Ser  Arg  Ile  Glu  Tyr  Ile
     105                      110                      115

CAT  TCA  AAG  AAC  TTC  ATC  CAC  CGG  GAT  GTG  AAG  CCA  GAC  AAC  TTC  CTC        558
His  Ser  Lys  Asn  Phe  Ile  His  Arg  Asp  Val  Lys  Pro  Asp  Asn  Phe  Leu
120                           125                      130                      135

ATG  GGC  CTG  GGG  AAG  AAG  GGC  AAC  CTG  GTG  TAC  ATC  ATC  GAC  TTC  GGG        606
Met  Gly  Leu  Gly  Lys  Lys  Gly  Asn  Leu  Val  Tyr  Ile  Ile  Asp  Phe  Gly
                    140                      145                      150

CTG  GCC  AAG  AAG  TAC  CGG  GAT  GCA  CGC  ACC  CAC  CAG  CAC  ATC  CCC  TAT        654
Leu  Ala  Lys  Lys  Tyr  Arg  Asp  Ala  Arg  Thr  His  Gln  His  Ile  Pro  Tyr
               155                      160                      165

CGT  GAG  AAC  AAG  AAC  CTC  ACG  GGG  ACG  GCG  CGG  TAC  GCC  TCC  ATC  AAC        702
Arg  Glu  Asn  Lys  Asn  Leu  Thr  Gly  Thr  Ala  Arg  Tyr  Ala  Ser  Ile  Asn
          170                      175                      180

ACG  CAC  CTT  GGA  ATT  GAA  CAA  TCC  CGA  AGA  GAT  GAC  TTG  GAG  TCT  CTG        750
Thr  His  Leu  Gly  Ile  Glu  Gln  Ser  Arg  Arg  Asp  Asp  Leu  Glu  Ser  Leu
     185                      190                      195

GGC  TAC  GTG  CTA  ATG  TAC  TTC  AAC  CTG  GGC  TCT  CTC  CCC  TGG  CAG  GGG        798
Gly  Tyr  Val  Leu  Met  Tyr  Phe  Asn  Leu  Gly  Ser  Leu  Pro  Trp  Gln  Gly
200                           205                      210                      215

CTG  AAG  GCT  GCC  ACC  AAG  AGA  CAG  AAA  TAC  GAA  AGG  ATT  AGC  GAG  AAG        846
Leu  Lys  Ala  Ala  Thr  Lys  Arg  Gln  Lys  Tyr  Glu  Arg  Ile  Ser  Glu  Lys
                    220                      225                      230

AAA  ATG  TCC  ACC  CCC  ATC  GAA  GTG  TTG  TGT  AAA  GGC  TAC  CCT  TCC  GAA        894
Lys  Met  Ser  Thr  Pro  Ile  Glu  Val  Leu  Cys  Lys  Gly  Tyr  Pro  Ser  Glu
               235                      240                      245

TTT  GCC  ACA  TAC  CTG  AAT  TTC  TGC  CGT  TCC  TTG  CGT  TTT  GAC  GAC  AAG        942
Phe  Ala  Thr  Tyr  Leu  Asn  Phe  Cys  Arg  Ser  Leu  Arg  Phe  Asp  Asp  Lys
          250                      255                      260

CCT  GAC  TAC  TCG  TAC  CTG  CGG  CAG  CTT  TTC  CGG  AAT  CTG  TTC  CAT  CGC        990
Pro  Asp  Tyr  Ser  Tyr  Leu  Arg  Gln  Leu  Phe  Arg  Asn  Leu  Phe  His  Arg
     265                      270                      275

CAG  GGC  TTC  TCC  TAT  GAC  TAC  GTG  TTC  GAC  TGG  AAC  ATG  CTC  AAA  TTT       1038
Gln  Gly  Phe  Ser  Tyr  Asp  Tyr  Val  Phe  Asp  Trp  Asn  Met  Leu  Lys  Phe
280                           285                      290                      295

GGT  GCC  AGC  CGG  GCC  GCC  GAT  GAC  GCC  GAG  CGG  GAG  CGC  AGG  GAC  CGA       1086
Gly  Ala  Ser  Arg  Ala  Ala  Asp  Asp  Ala  Glu  Arg  Glu  Arg  Arg  Asp  Arg
                    300                      305                      310

GAG  GAG  CGG  CTG  AGA  CAC  TCG  CGG  AAC  CCG  GCT  ACC  CGC  GGC  CTC  CCT       1134
Glu  Glu  Arg  Leu  Arg  His  Ser  Arg  Asn  Pro  Ala  Thr  Arg  Gly  Leu  Pro
               315                      320                      325

TCC  ACA  GCC  TCC  GGC  CGC  CTG  CGG  GGG  ACG  CAG  GAA  GTG  GCT  CCC  CCC       1182
Ser  Thr  Ala  Ser  Gly  Arg  Leu  Arg  Gly  Thr  Gln  Glu  Val  Ala  Pro  Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     |     | 330 |     |     |     | 335 |     |     |     |     | 340 |     |      |
| ACA | CCC | CTC | ACC | CCT | ACC | TCA | CAC | ACG | GCT | AAC | ACC | TCC | CCC | CGG | CCC | 1230 |
| Thr | Pro | Leu | Thr | Pro | Thr | Ser | His | Thr | Ala | Asn | Thr | Ser | Pro | Arg | Pro |      |
|     | 345 |     |     |     |     | 350 |     |     |     |     | 355 |     |     |     |     |      |
| GTC | TCC | GGC | ATG | GAG | AGA | GAG | CGG | AAA | GTG | AGT | ATG | CGG | CTG | CAC | CGC | 1278 |
| Val | Ser | Gly | Met | Glu | Arg | Glu | Arg | Lys | Val | Ser | Met | Arg | Leu | His | Arg |      |
| 360 |     |     |     |     | 365 |     |     |     |     | 370 |     |     |     |     | 375 |      |
| GGG | GCC | CCC | GTC | AAC | ATC | TCC | TCG | TCC | GAC | CTC | ACA | GGC | CGA | CAA | GAT | 1326 |
| Gly | Ala | Pro | Val | Asn | Ile | Ser | Ser | Ser | Asp | Leu | Thr | Gly | Arg | Gln | Asp |      |
|     |     |     |     | 380 |     |     |     |     | 385 |     |     |     |     | 390 |     |      |
| ACC | TCT | CGC | ATG | TCC | ACC | TCA | CAG | ATT | CCT | GGT | CGG | GTG | GCT | TCC | AGT | 1374 |
| Thr | Ser | Arg | Met | Ser | Thr | Ser | Gln | Ile | Pro | Gly | Arg | Val | Ala | Ser | Ser |      |
|     |     | 395 |     |     |     |     | 400 |     |     |     |     | 405 |     |     |     |      |
| GGT | CTT | CAG | TCT | GTC | GTG | CAC | CGA | TGAGAACTCT | CCTTATTGCT | GTGAAGGGCA | | | | | | 1428 |
| Gly | Leu | Gln | Ser | Val | Val | His | Arg |  |  |  | | | | | |      |
|     | 410 |     |     |     |     |     | 415 |  |  |  | | | | | |      |

```
GACAATGCAT GGCTGATCTA CTCTGTTACC AATGGCTTTA CTAGTGACAC GTCCCCCGGT    1488
CTAGGATCGA AATGTTAACA CCGGGAGCTC TCCAGGCCAC TCACCCAGCG ACGCTCGTGG    1548
GGGAAACATA CTAAACGGAC AGACTCCAAG AGCTGCCACC GCTGGGGCTG CACTGCGGCC    1608
CCCCACGTGA ACTCGGTTGT AACGGGGCTG GAAGAAAAG CAGAGAGAGA ATTGCAGAGA    1668
ATCAGACTCC TTTTCCAGGG CCTCAGCTCC CTCCAGTGGT GGCCGCCCTG TACTCCCTGA    1728
CGATTCCACT GTAACTACCA ATCTTCTACT TGGTTAAGAC AGTTTTGTAT CATTTTGCTA    1788
AAAATTATTG GCTTAAATCT GTGTAAAGAA AATCTGTCTT TTTATTGTTT CTTGTCTGTT    1848
TTTGCGGTCT TACAAAAAAA ATGTTGACTA AGGAATTCTG AGACAGGCTG GCTTGGAGTT    1908
AGTGTATGAG GTGGAGTCGG GCAGGGAGAA GGTGCAGGTG GATCTCAAGG GTGTGTGCTG    1968
TGTTTGTTTT GCAGTGTTTT ATTGTCCGCT TTGGAGAGGA GATTTCTCAT CAAAAGTCCG    2028
TGGTGTGTGT GTGTGCCCGT GTGTGGTGGG ACCTCTTCAA CCTGATTTTG GCGTCTCACC    2088
CTCCCTCCTC CCGTAATTGA CATGCCTGCT GTCAGGAACT CTTGAGGCCC TCGGAGAGCA    2148
GTTAGGGACC GCAGGCTGCC GCGGGGCAGG GGTGCAGTGG GTGTTACCAG GCAAAGCACT    2208
GCGCGCTTCT TCCCCAGGAG GTGGGCAGGC AGCTGAGAGC TTGGAAGCAG AGGCTTTGAG    2268
ACCCTAGCAG GACAATTGGG AGTCCAGGA TTCAAGGTGG AAGATGCGTT TCTGGTCCCT    2328
TGGGAGAGGA CTGTGAACCG AGAGGTGGTT ACTGTAGTGT TTGTTGCCTT GCTGCCTTTG    2388
CACTCAGTCC ATTTCTCAG CACTCAATGC TCCTGTGCGG ATTGGCACTC CGTCTGTATG    2448
AATGCCTGTG GTTAAAACCA GGAGCGGGGC TGTCCTTGCC ACGTGCCAAG ACTAGCTCAG    2508
AAAAGCCGGC AGGCCAGAAG GACCCACCCT GAGGTGCCAA GGAGCAGGTG ACTCTCCCAA    2568
CCGGACCCAG AACCTTCACG GCCAGAAAGT AGAGTCTGCG CTGTGACCTT CTGTTGGGCG    2628
CGTGTCTGTT GGTCAGAAGT GAAGCAGCGT GCGTGGGGCC GAGTCCACC AGAAGGCAGG    2688
TGGCCTCCGT GAGCTGGTGC TGCCCCAGGC TCCATGCTGC TGTGCCCTGA GGTTCCCAGG    2748
ATGCCTTCTC GCCTCTCACT CCGCAGCACT TGGGCGGTAG CCAGTGGCCA TGTGCTCCCA    2808
ACCCCAATGC GCAGGGCAGT CTGTGTTCGT GGGCACTTCG GCTGGACCCC ATCACGATGG    2868
ACGATGTTCC CTTTGGACTC TAGGGCTTCG AAGGTGTGCA CCTTGGTTCT CCCTTCTCCT    2928
CCCCAGAGTT CCCCCGGATG CCATAACTGG CTGGCGTCCC AGAACACAGT TGTCAACCCC    2988
CCCACCAGCT GGCTGGCCGT CTGTCTGAGC CCATGGATGC TTTCTCAATC CTAGGCTGGT    3048
TACTGTGTAA GCGTGTTGGA GTACGGCGCC TTGAGCGGGT GGGAGCTGTG TGTTGAAGTA    3108
CAGAGGGAGG TTGGGGTGGG TCAGAGCCGA GTTAAGAGAT TTTCTTTGTT GCTGGACCCC    3168
```

```
TTCTTGAAGG TAGACGTCCC CCACCCGGAG AGACGTCGCG CTGTGGCCTG AAGTGGCGCA    3228

AGCTTGCTTT GTAAATATCT GTGGTCCCGA TGTAGTGCCC AGAACGTTTG TGCGAGGCAG    3288

CTCTGCGCCC GGGTTCCAGC CCGAGCCTCG CCGGGTCGCG TCTTCGGAGT GCTTGTGACA    3348

GTCCTTGCCC AGTATCTAGT CCCCGTCGCC CCGTGCAGGA GACGTAGGTA GGACGTCGTG    3408

TCAGCTGTGC ACTGACGGCC AGTCTCCGAG CTGTGCGTTT GTATCGCCAC TGTATTTGTG    3468

TACTTTAACA ATCGTGTAAA TAATAAATTC GGAATTC                              3505
```

(2) INFORMATION FOR SEQ ID NO:35:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO:35:

```
Met Glu Leu Arg Val Gly Asn Arg Tyr Arg Leu Gly Arg Lys Ile Gly
 1               5                  10                  15

Ser Gly Ser Phe Gly Asp Ile Tyr Leu Gly Thr Asp Ile Ala Ala Gly
            20                  25                  30

Glu Glu Val Ala Ile Lys Leu Glu Cys Val Lys Thr Lys His Pro Gln
        35                  40                  45

Leu His Ile Glu Ser Lys Ile Tyr Lys Met Met Gln Gly Gly Val Gly
    50                  55                  60

Ile Pro Thr Ile Arg Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
           100                 105                 110

Ile Ser Arg Ile Glu Tyr Ile His Ser Lys Asn Phe Ile His Arg Asp
       115                 120                 125

Val Lys Pro Asp Asn Phe Leu Met Gly Leu Gly Lys Lys Gly Asn Leu
   130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
           180                 185                 190

Arg Asp Asp Leu Glu Ser Leu Gly Tyr Val Leu Met Tyr Phe Asn Leu
       195                 200                 205

Gly Ser Leu Pro Trp Gln Gly Leu Lys Ala Ala Thr Lys Arg Gln Lys
   210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ala Thr Tyr Leu Asn Phe Cys Arg
                245                 250                 255

Ser Leu Arg Phe Asp Asp Lys Pro Asp Tyr Ser Tyr Leu Arg Gln Leu
           260                 265                 270

Phe Arg Asn Leu Phe His Arg Gln Gly Phe Ser Tyr Asp Tyr Val Phe
       275                 280                 285

Asp Trp Asn Met Leu Lys Phe Gly Ala Ser Arg Ala Ala Asp Asp Ala
   290                 295                 300
```

| Glu 305 | Arg | Glu | Arg | Arg | Asp | Arg 310 | Glu | Glu | Arg | Leu 315 | Arg | His | Ser | Arg | Asn 320 |

| Pro | Ala | Thr | Arg | Gly 325 | Leu | Pro | Ser | Thr | Ala 330 | Ser | Gly | Arg | Leu | Arg 335 | Gly |

| Thr | Gln | Glu | Val 340 | Ala | Pro | Pro | Thr | Pro 345 | Leu | Thr | Pro | Thr | Ser 350 | His | Thr |

| Ala | Asn | Thr 355 | Ser | Pro | Arg | Pro | Val 360 | Ser | Gly | Met | Glu | Arg 365 | Glu | Arg | Lys |

| Val | Ser 370 | Met | Arg | Leu | His | Arg 375 | Gly | Ala | Pro | Val | Asn 380 | Ile | Ser | Ser | Ser |

| Asp 385 | Leu | Thr | Gly | Arg | Gln 390 | Asp | Thr | Ser | Arg | Met 395 | Ser | Thr | Ser | Gln | Ile 400 |

| Pro | Gly | Arg | Val | Ala 405 | Ser | Ser | Gly | Leu | Gln 410 | Ser | Val | Val | His | Arg 415 | |

(2) INFORMATION FOR SEQ ID NO:36:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

CTAGATCTAG CTAGACCATG GTAGTTTTTT CTCCTTGACG    40

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

CATGCCATGG CACGACCTAG T    21

(2) INFORMATION FOR SEQ ID NO:38:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CTAGATCTAG CTAGACCATG GTAGTTTTTT CTCCTTGACG    40

(2) INFORMATION FOR SEQ ID NO:39:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

GAATCGGGCC GCCGAGATCT CATATGGAGC TGAGAGTC 38

( 2 ) INFORMATION FOR SEQ ID NO:40:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

CCCGGATCTA GCAGATCTCA T 21

( 2 ) INFORMATION FOR SEQ ID NO:41:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

Ala Ser Ser Ser Gly Ser Lys Ala Glu Phe Ile Val Gly Gly Tyr
1               5                   10                  15

( 2 ) INFORMATION FOR SEQ ID NO:42:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

Arg Ser Met Thr Val Ser Thr Ser Gln Asp Pro Ser Phe Ser Gly Tyr
1               5                   10                  15

( 2 ) INFORMATION FOR SEQ ID NO:43:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

TACATCTAGA ATTATGGCGA GTAGCAGCGG C 31

( 2 ) INFORMATION FOR SEQ ID NO:44:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

AATGGATCCT TAGAAACCTG TGGGGGT 27

( 2 ) INFORMATION FOR SEQ ID NO:45:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:45:

AATGGATCCT TAGAAACCTT TCATGTTACT CTTGGT   36

( 2 ) INFORMATION FOR SEQ ID NO:46:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:46:

TACATCTAGA ATTATGGAGC TGAGAGTCGG G   31

( 2 ) INFORMATION FOR SEQ ID NO:47:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:47:

GGATCCTCAT CGGTGCACGA CAGACTG   27

( 2 ) INFORMATION FOR SEQ ID NO:48:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:48:

TACATCTAGA ATTATGGCAC GACCTAGTGG TCGATCG   37

( 2 ) INFORMATION FOR SEQ ID NO:49:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:49:

GGGGATCCTA CTTCAGTAGG GGCTG   25

( 2 ) INFORMATION FOR SEQ ID NO:50:

( i ) SEQUENCE CHARACTERISTICS:
    ( A ) LENGTH: 12 amino acids
    ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:50:

Arg Ser Gly His Asn Thr Arg Gly Thr Gly Ser Ser
1               5                   10

(2) INFORMATION FOR SEQ ID NO:51:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:51:

Arg Leu Gly His Asn Thr Arg Gly Thr Gly Ser Ser
1               5                   10

(2) INFORMATION FOR SEQ ID NO:52:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:52:

Ser Ser Arg Pro Lys Thr Asp Val Leu Val Gly
1               5                   10

(2) INFORMATION FOR SEQ ID NO:53:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:53:

Lys Ser Asp Asn Thr Lys Ser Glu Met Lys His Ser
1               5                   10

(2) INFORMATION FOR SEQ ID NO:54:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:54:

Gly Thr Asp Ile Ala Ala Gly Glu
1               5

(2) INFORMATION FOR SEQ ID NO:55:

(i) SEQUENCE CHARACTERISTICS:
    (A) LENGTH: 10 amino acids
    (B) TYPE: amino acid (C) STRANDEDNESS: single
        (D) TOPOLOGY: linear (ii) MOLECULE TYPE: peptide (xi) SEQUENCE DESCRIPTION: SEQ ID NO:55:

Glu Arg Arg Asp Arg Glu Glu Arg Leu Arg
    1               5                   10

(2) INFORMATION FOR SEQ ID NO:56:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

Thr Gly Lys Gln Thr Asp Lys Thr Lys Ser Asn Met Lys Gly Tyr
    1               5                   10                  15

(2) INFORMATION FOR SEQ ID NO:57:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Asp Leu Leu Gly Pro Ser Leu Glu Asp Leu Phe Gly Tyr
    1               5                   10

PROTEIN KINASES

This is a divisional application of U.S. patent application Ser. No. 08/185,359, filed Jan. 21, 1994 still pending which is a Continuation-in-Part of U.S. application Ser. No. 08/008,001, filed Jan. 21, 1993, now abandoned which is a Continuation-in-Part of U.S. application Ser. No. 728,783, filed Jul. 3, 1991 now abandoned.

FIELD OF THE INVENTION

The present invention relates to novel polynucleotides encoding polypeptides which correspond to the class of protein kinase isolates heretofore referred to as casein kinase I and which possess protein kinase and/or DNA recombination/repair promoting functional capabilities.

BACKGROUND OF THE INVENTION

Protein Kinases

The protein kinases comprise an exceptionally large family of eukaryotic proteins which mediate the responses of cells to external stimuli and are related by amino acid sequence homology within the so-called "catalytic domain" of the enzymes. To date, in excess of 100 unique members of the protein kinase family from a wide variety of eukaryotic organisms have been described and characterized at the amino acid sequence level. See, e.g., Hanks, et al. (Science, 241:42–52, 1988) which presents a sequence alignment of 65 protein kinase catalytic domains which range in size from about 250 to 300 amino acids and Hanks, et al. (Methods in Enzymol., 200:38–62, 1991) presenting a catalytic domain sequence alignment for 117 distinct protein kinase family members including a variety of vertebrate, invertebrate, higher plant and yeast species enzymes. The location of the catalytic domain within a protein kinase is not fixed. In most single subunit enzymes, the domain is near the carboxy terminus of the polypeptide while in multimeric protein kinases the catalytic domain takes up almost the entirety of the subunit polypeptide.

Protein kinases are generally classified into a protein-serine/threonine subfamily or a protein-tyrosine subfamily on the basis of phosphorylation substrate specificity. Among the many classes of enzymes within the protein-serine/threonine kinase subfamily are two distinct classes which have been designated casein kinase I and casein kinase II based on the order of their elution from DEAE-cellulose. The casein kinases are distinguished from other protein kinases by their ability to phosphorylate serine or threonine residues within acidic recognition sequences such as found in casein. Tuazon, et al., (Adv. in Second Messenger and Phosphoprotein Res., 23:123–164, 1991) presents a review of over 200 publications related to casein kinase I and II, addressing the physicochemical characterization, recognition sequences, substrate specificity and effects on metabolic regulation for these two classes of enzymes. Casein kinase II is active as a heterotetramer and the complete amino acid sequences of human, rat, Drosophila and yeast species catalytic regions have been determined. Despite the fact that partially purified casein kinase I preparations have been obtained from cell nuclei, cytoplasm, and cell membranes of various plant and animal species, prior to the present invention, nothing was known concerning the primary structure of its enzymatically active monomeric subunit.

As of the time of the present invention, therefore, there existed a significant need in the art for information concerning the primary structure (amino acid sequence) of protein-serine/threonine kinase enzymes of the casein kinase I class. Such information, provided in the form of DNA sequences encoding one or more of these kinases (from which primary structures could be deduced), would allow for the large scale production of kinases by recombinant techniques as well as for determination of the distribution and function of these enzymes, the structural distinctions between membrane-bound and non-membranous forms, the potential ligand-receptor interactions in which these kinases interact, and the identification of agents capable of modulating ligand-receptor binding, kinase, and other activities.

DNA Recombination And Repair

Chromosomes experience single-stranded or double-stranded breaks as a result of energy-rich radiation, chemical agents, as well as spontaneous breaks occurring during replication among others. Although genes present in the chromosomes undergo continuous damage, repair, exchange, transposition, and splicing, certain enzymes protect or restore the specific base sequences of the chromosome.

The repair of DNA damage is a complex process that involves the coordination of a large number of gene products. This complexity is in part dependent upon both the form of DNA damage and cell cycle progression. For example, in response to ultraviolet (UV) irradiation, cells can employ photoreactivation or excision repair functions to correct genetic lesions. The repair of strand breaks, such as those created by X-rays, can proceed through recombinational mechanisms. For many forms of DNA damage, the cell is induced to arrest in the G2 phase of the cell cycle. During this G2 arrest, lesions are repaired to ensure chromosomal integrity prior to mitotic segregation.

Since the transfer of genetic information from generation to generation is dependent on the integrity of DNA, it is important to identify those gene products which affect or regulate genetic recombination and repair. Through the use of organisms with specific genetic mutations, the normal functional gene can be obtained, molecularly cloned, and the gene products studied.

In eukaryotes such as Saccharomyces cerevisiae, genetic studies have defined repair-deficient mutants which have allowed the identification of more than 30 radiation-sensitive (RAD) mutants (Haynes, et al., in Molecular Biology of the Yeast Saccharomyces, pp. 371, 1981; J. Game in Yeast Genetics: Fundamental and Applied Aspects, pp. 109, 1983). These mutants can be grouped into three classes depending upon their sensitivities. These classes broadly define excision-repair, error-prone repair, and recombinational-repair functions. The molecular characterization of yeast RAD genes has increased the understanding of the enzymatic machinery involved in excision repair, as well as the arrest of cell division by DNA damage.

The understanding of RAD genes and their expression products has become increasingly important as research continues to develop more effective therapeutic compositions. Often these new compositions appear quite effective against a particular disease condition, such as certain tumors, but prove to be too toxic for in vivo therapy in an animal having the disease. Indeed, these compositions can actually increase the likelihood of mutagenesis.

Most agents that are mutagenic or carcinogenic are in themselves unreactive, but are broken down to reactive intermediates in vivo. It is these reactive intermediates which interact with DNA to produce a mutation. This event is thought to be the initial step in chemical carcinogenesis. Mutations in a large number of genes affect the cellular response to agents that damage DNA. In all likelihood, many of these mutated genes encode enzymes that participate in DNA repair systems. Consequently, when the repair system is compromised, the cells become extremely sensitive to toxic agents. Although the DNA may revert to normal when DNA repair mechanisms operate successfully, the failure of such mechanisms can result in a transformed tumor cell which continues to proliferate.

Although there are currently available tests to determine the toxicity or mutagenicity of chemical agents and compositions, there are limitations in both laboratory screening procedures and animal toxicity tests. These limitations include extrapolating laboratory data from animals to humans. There is often a large measure of uncertainty when attempting to correlate the results obtained in laboratory animals with effects in human subjects. In most cases, doses of the test drug have been used in the animal which are too high to be safely administered to humans. In addition, some types of toxicity can be detected if the drug is administered in a particular species, yet may be missed if the experiment is not done in the correct animal species. Moreover, many currently available laboratory tests are incapable of detecting certain types of toxic manifestations which occur in man.

Phenotypic complementation, as a way of identifying homologous normal functional genes, is widely used. For example, the human homologue of the yeast cell cycle control gene, cdc 2, was cloned by expressing a human cDNA library in *Schizosaccharomyces pombe* and selecting those clones which could complement a mutation in the yeast cdc 2 gene (Lee, et al., Nature, 327:31, 1987). A mammalian gene capable of reverting the heat shock sensitivity of the RAS2$^{val19}$ gene of yeast, has also been cloned by using complementation (Colicelli, et al., Proc. Nat'l. Acad. Sci. USA, 86:3599, 1989). A rat brain cDNA library was used to clone a mammalian cDNA that can complement the loss of growth control associated with the activated RAS2 gene in yeast. The gene, DPD (dunce-like phosphodiesterase), encodes a high-affinity CAMP phosphodiesterase.

In summary, limitations and uncertainties of existing laboratory tests fail to provide an accurate method of examining the effects of a composition on DNA integrity. In view of this, a considerable need exists for screening methodologies which are inexpensive, rapid, and contain the relevant gene from the animal which is to be treated with the composition. Such methods provide a direct assay to determine if a composition interferes with the DNA repair system of a cell.

SUMMARY OF THE INVENTION

In one of its aspects, the present invention provides purified and isolated polynucleotides (e.g., DNA sequences and RNA transcripts thereof) encoding eukaryotic protein kinases of the casein kinase I class herein designated as "HRR25-like" proteins and characterized by greater than 35% amino acid sequence homology with the prototypical yeast enzyme HRR25 through the protein kinase catalytic domain thereof. Polynucleotides provided by the invention include RNAs, mRNAs and DNAs, including antisense forms thereof. Preferred DNA sequences of the invention include genomic and cDNA sequences as well as wholly or partially chemically synthesized DNA sequences and biological replicas thereof. Specifically illustrating the invention are *Saccharomyces cerevisiae* DNAs including those encoding HRR25 and NUF1, *Schizosaccharomyces pombe* DNAs including those encoding Hhp1+ and Hhp2+, and human DNAs including those encoding CKIα1Hu, CKIα2Hu, CKIα3Hu, CKIγ1Hu, CKIγ2Hu, and CKIδHu. Also provided are autonomously replicating recombinant constructions such as plasmid and viral DNA vectors incorporating such sequences and especially vectors wherein DNA encoding an HRR25-like casein kinase I protein is linked to an endogenous or exogenous expression control DNA sequence.

According to another aspect of the invention, host cells, especially unicellular host cells such as procaryotic and eukaryotic cells, are stably transformed with DNA sequences of the invention in a manner allowing the desired polypeptides to be expressed therein. Host cells expressing such HRR25-like products can serve a variety of useful purposes. To the extent that the expressed products are "displayed" on host cell surfaces, the cells may constitute a valuable immunogen for the development of antibody substances specifically immunoreactive therewith.

Host cells of the invention are conspicuously useful in methods for the large scale production of HRR25-like proteins wherein the cells are grown in a suitable culture medium and the desired polypeptide products are isolated from the cells or from the medium in which the cells are grown.

Also comprehended by the present invention are antibody substances (e.g., monoclonal and polyclonal antibodies, single chain antibodies, chimeric antibodies, CDR-grafted antibodies and the like) and other binding proteins which are specific for HRR25-like proteins (i.e., non-reactive with protein kinase molecules which are not related by at least 35% homology with HRR25 through the protein kinase catalytic domain). Antibody substances can be developed using isolated natural or recombinant HRR25-like proteins or cells expressing such products on their surfaces. The antibody substances are useful, in turn, for purifying recombinant and naturally occurring HRR25-like polypeptides and identifying cells producing such polypeptides on their surfaces. The antibody substances and other binding proteins are also manifestly useful in modulating (i.e., blocking, inhibiting, or stimulating) ligand-receptor binding reactions involving HRR25-like proteins. Anti idiotypic antibodies specific for anti-HRR25-like antibody substances are also contemplated. Assays for the detection and quantification of HRR25-like proteins on cell surfaces and in fluids such as serum and cytoplasmic fractions may involve a single antibody substance or multiple antibody substances in a "sandwich" assay format.

Recombinant HRR25-like protein products obtained according to the invention have been observed to display a number of properties which are unique among the eukaryotic protein kinases. As one example, the HRR25 protein possesses both protein-tyrosine kinase and protein-serine/threonine kinase activities. Moreover, HRR25 operates to promote repair of DNA strand breaks at a specific nucleotide sequence and is the only protein kinase known to have such recombination/repair promoting activity.

The DNA sequence information for yeast and mammalian (including human) species HRR25-like proteins which is provided by the present invention makes possible the identification and isolation of DNAs encoding other HRR25-like proteins by such well-known techniques as DNA/DNA hybridization and polymerase chain reaction (PCR) cloning.

Recombinant HRR25-like proteins and host cells expressing the same are useful in screening methods designed to examine the effects of various compositions on DNA break repair and protein kinase activities of the proteins. Protein kinase inhibitory effects may be assessed by well-known screening procedures such as described in Hidaka, et al. (*Methods in Enzymology*, 201:328–339, 1991).

BRIEF DESCRIPTION OF THE DRAWING

Further aspects and advantages of the present invention will be apparent upon consideration of the following detailed description of presently preferred embodiments thereof, reference being made to the drawing wherein:

FIGS. 2(A and B) presents an alignment of the predicted amino acid sequences of HRR25 with the sequences of three other *Saccharomyces cerevisiae* HRR25-like proteins (YCK1/CKI2, YCK2/CKI1, and NUF1), two HRR25-like proteins (Hhp1+ and Hhp2+) from *Schizosaccharomyces pombe* and three putative isoforms (CKIα1Hu, CKIα2Hu, and CKIα3Hu) of a human HRR25-like protein.

DETAILED DESCRIPTION OF THE INVENTION

Figures 1A, 1B:
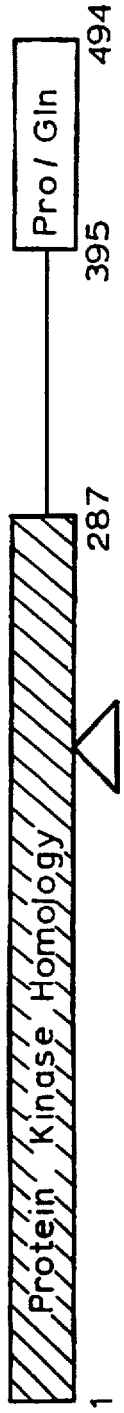
FIG. 1(A) presents an alignment of the predicted amino acid sequence of HRR25 with the catalytic domains of the yeast CDC28, yeast KSS1 and human RAF1 protein kinases.
FIG. 1(B) shows a schematic representation of the structure of HRR25.

In one of its aspects, the present invention relates to a DNA encoding a recombination/repair promoting polypeptide which can be used in an assay system to examine the effects of various compositions on DNA integrity. These functional sequences, which can be characterized by their ability to promote restoration of DNA strand breaks, permit the screening of compositions to determine whether a particular composition has an effect on the restoration of such repair activity. The invention also provides a DNA sequence encoding a polypeptide which promotes normal mitotic recombination, but is defective in protein kinase activity and essentially unable to repair DNA strand breaks. This defective DNA sequence is highly useful for identifying other DNA sequences which encode proteins with functional protein kinase activity. In addition, the present invention relates to the polypeptide encoded by the defective DNA sequence, as well as the polypeptide encoded by the functional wild-type DNA.

In order to identify a DNA sequence encoding a polypeptide with protein kinase activity, a method is provided whereby a DNA library is screened for nucleotide sequences capable of restoring DNA strand break repair in a mutant lacking such activity. A method is further provided for identifying a composition which affects the activity of a mammalian polypeptide having protein kinase activity, wherein the polypeptide is capable of restoring DNA double-strand break repair activity in a mutant lacking such activity.

In general, the defective protein kinase can be characterized by its ability to promote normal mitotic recombination, while being essentially unable to repair DNA double-strand break including that which occurs at the cleavage site:

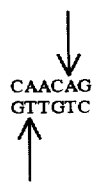

The DNA double-strand breaks which the defective protein kinase is essentially unable to repair can be induced by various means, including endonucleases, x-rays, or radiomimetic agents including alkylating agents. Preferred endonucleases are those which recognize the same nucleotide cleavage site as endonuclease HO. Radiomimetic alkylating agents having methylmethane sulfonate activity are preferred. Those of skill in the art will be able to identify other agents which induce the appropriate DNA strand breaks without undue experimentation.

The present invention specifically discloses mutants sensitive to continuous expression of the DNA double-strand endonuclease HO, which codes for a 65 kDa site-specific endonuclease that initiates mating type interconversion (Kostriken, et al., *Cold Spring Harbor Symp. Quant. Biol.*, 49:89, 1984). These mutants are important to understanding the functions involved in recognizing and repairing damaged chromosomes. This invention also discloses a yeast wild-type DNA recombination and repair gene called HRR25 (HO and/or radiation repair). Homozygous mutant strains, hrr25-1, are sensitive to methylmethane sulfonate and X-rays, but not UV irradiation. The wild-type gene encodes a novel protein kinase, homologous to other serine/threonine kinases, which appears critical in activation of DNA repair functions by phosphorylation.

The HRR25 kinase is important for normal cell growth, nuclear segregation, DNA repair and meiosis, and deletion of HRR25 results in cell cycle defects. These phenotypes, coupled with the sequence similarities between the HRR25 kinase and the Raf/c-mos protein kinase subgroup suggest that HRR25 might play a similar role in *S. cerevisiae* growth and development. The defects in DNA strand break repair and the aberrant growth properties revealed by mutations in HRR25 kinase, expands the role that protein kinases may play and places HRR25 in a functional category of proteins associated with DNA metabolism.

The development of specific DNA sequences encoding protein kinase polypeptides of the invention can be accomplished using a variety of techniques. For example, methods which can be employed include (1) isolation of a double-stranded DNA sequence from the genomic DNA of the eukaryote; (2) chemical synthesis of a DNA sequence to provide the necessary codons for the polypeptide of interest; and (3) in vitro synthesis of a double stranded DNA sequence by reverse transcription of mRNA isolated from a eukaryotic donor cell. In the latter case, a double stranded DNA complement of MRNA is eventually formed which is generally referred to as CDNA.

The novel DNA sequences of the invention include all sequences useful in providing for expression in prokaryotic or eukaryotic host cells of polypeptides which exhibit the functional characteristics of the novel protein kinase of the invention. These DNA sequences comprise: (a) the DNA sequences as set forth in SEQ. I.D. No. 1 or their complementary strands; (b) DNA sequences which encode an amino acid sequence with at least about 35% homology in the protein kinase domain with the amino acid sequences encoded by the DNA sequences defined in (a) or fragments thereof; and (c) DNA sequences defined in (a) and (b) above. Specifically embraced in (b) are genomic DNA sequences which encode allelic variant forms. Part (c) specifically embraces the manufacture of DNA sequences which encode fragments of the protein kinase and analogs of the protein kinase wherein the DNA sequences thereof may incorporate codons which facilitate translation of mRNA. Also included in part (c) are DNA sequences which are degenerate as a result of the genetic code.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

With the DNA sequences of the invention in hand, it is a routine matter to prepare, subclone, and express smaller DNA fragments from this or a corresponding DNA sequences. The term "polypeptide" denotes any sequence of amino acids having the characteristic activity of the mutant or wild-type protein kinase of the invention, wherein the sequence of amino acids is encoded by all or part of the DNA sequences of the invention.

The polypeptide resulting from expression of the DNA sequence of the invention can be further characterized as being free from association with other eukaryotic polypeptides or other contaminants which might otherwise be associated with the protein kinase in its natural cellular environment.

Isolation and purification of microbially expressed polypeptides provided by the invention may be by conventional means including, preparative chromatographic separations and immunological separations involving monoclonal and/or polyclonal antibody preparation.

In general, recombinant expression vectors useful in the present invention contain a promotor sequence which facilitates the efficient transcription of the inserted eukaryotic genetic sequence. The expression vector typically contains an origin of replication, a promoter, and a terminator, as well as specific genes which are capable of providing phenotypic selection of the transformed cells. The transformed hosts can be grown in fermentors and cultured according to techniques known in the art to achieve optimal cell growth. The polypeptides of the invention can then be isolated from the growth medium, cellular lysates, or cellular membrane fractions.

The DNA sequences of the present invention can be expressed in vivo in either prokaryotes or eukaryotes. Methods of expressing DNA sequences containing eukaryotic coding sequences in prokaryotes are well known in the art. Biologically functional viral and plasmid DNA vectors used to incorporate DNA sequences of the invention, for expression and replication in the host cell are well known in the art. For example, DNA can be inserted in yeast using appropriate vectors and introducing the product into the host cells. Various shuttle vectors for the expression of foreign genes in yeast have been reported (Heinemann, et al., *Nature*, 340:205, 1989; Rose, et al., *Gene*, 60:237, 1987). Those of skill in the art will know of appropriate techniques for obtaining gene expression in both prokaryotes and eukaryotes, or can readily ascertain such techniques, without undue experimentation.

Hosts include microbial, yeast, insect and mammalian host organisms. Thus, the term "host" is meant to include not only prokaryotes, but also such eukaryotes such as yeast, filamentous fungi, as well as plant and animal cells which can replicate and express an intron-free DNA sequence of the invention. The term also includes any progeny of the subject cell. It is understood that not all progeny are identical to the parental cell since there may be mutations that occur at replication. However, such progeny are included when the terms above are used.

Transformation with recombinant DNA may be carried out by conventional techniques well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl could be used in the reaction. Transformation can also be performed after forming a protoplast of the host cell.

Where the host is a eukaryote, various methods of DNA transfer can be used. These include transfection of DNA by calcium phosphate-precipitates, conventional mechanical procedures such as microinjection, insertion of a plasmid encased in liposomes, spheroplast electroporation, salt mediated transformation of unicellular organisms or the use of virus vectors.

Analysis of eukaryotic DNA has been greatly simplified since eukaryotic DNA can be cloned in prokaryotes using vectors well known in the art. Such cloned sequences can be obtained easily in large amounts and can be altered in vivo by bacterial genetic techniques and in vitro by specific enzyme modifications. To determine the effects of these experimentally induced changes on the function and expression of eukaryotic genes, the rearranged sequences must be taken out of the bacteria in which they were cloned and reintroduced into a eukaryotic organism. Since there are still many functions in eukaryotic cells which are absent in prokaryotes, (e.g., localization of ATP-generating systems to mitochondria, association of DNA with histones, mitosis and meiosis, and differentiation of cells), the genetic control of such functions must be assessed in a eukaryotic environment. Cloning genes from other eukaryotes in yeast has been useful for analyzing the cloned eukaryotic genes as well as other yeast genes. A number of different yeast vectors have been constructed for this purpose. All vectors replicate in *E. coli*, which is important for amplification of the vector DNA. All vectors contain markers, e.g., LEU 2, HIS 3, URA 3, that can be selected easily in yeast. In addition, these vectors also carry antibiotic resistance markers for use in *E. coli*.

Many strategies for cloning human homologues of known yeast genes are known in the art. These include, but are not limited to: 1) low stringency hybridization to detect shared nucleotide sequences; 2) antibody screening of expression libraries to detect shared structural features; and 3) complementation of mutants to detect genes with similar functions.

For purposes of the present invention, protein kinases which are homologous can be identified by structural as well as functional similarity. Structural similarity can be determined, for example, by assessing amino acid homology or by screening with antibody, especially a monoclonal antibody, which recognizes a unique epitope present on the protein kinases of the invention. When amino acid homology is used as criteria to establish structural similarity, those amino acid sequences which have homology of at least about 35% in the protein kinase domain with the prototypical HRR25 protein are considered to uniquely characterize polypeptides.

Conserved regions of amino acid residues in HRR25 can be used to identify HRR25-like genes from other species. Conserved regions which can be used as probes for identification and isolation of HRR25-like genes (homologues) include the nucleotides encoding amino acid sequences GPSLED (amino acids 86 to 91 in SEQ ID NO: 2), RDIK-PDNFL (amino acids 127 to 135 in SEQ ID NO: 2), HIPYRE (amino acids 164 to 169 in SEQ ID NO: 2), and SVN (amino acids 181 to 183 in SEQ ID NO: 2), for example. These conserved motifs can be used, for example, to develop nucleotide primers to detect other HRR25-like genes by methods well known to those skilled in the art, such as polymerase chain reaction (PCR).

When homologous amino acid sequences are evaluated based on functional characteristics, then a homologous amino acid sequence is considered equivalent to an amino acid sequence of the invention when the homologous sequence is essentially unable to repair (in the case of the repair defective mutant gene) or able to repair (in the case of the natural gene), DNA double-strand breaks, including that which occurs at a nucleotide cleavage site

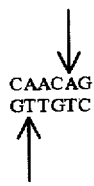

and when the homologous amino acid sequence allows normal mitotic recombination.

This invention provides screening methods whereby genes are cloned from plasmid libraries by complementation of a recessive marker. A recipient strain such as *Saccharomyces cerevisiae* is constructed that carries a recessive mutation in the gene of interest. This strain is then transformed with a plasmid, for example, pYES2 (Invitrogen, San Diego, Calif.) containing the wild-type genomic DNA or cDNA. The clone carrying the gene of interest can then be selected by replica plating to a medium that distinguishes mutant from wild-type phenotypes for the gene of interest. The plasmid can then be extracted from the clone and the DNA studied. Several yeast vectors allow the application of complementation systems to go beyond isolation of yeast genes. Genes from a wide variety of species can be isolated using these vectors. In such systems, DNA sequences from any source are cloned into a vector and can be screened directly in yeast for activities that will complement specific yeast mutations.

In a preferred embodiment, the present invention uses a mutation in yeast, the hrr25 mutation, which was identified by sensitivity to DNA double-strand breaks induced by the HO endonuclease. The genomic DNA which complements this mutation was isolated by transforming the hrr25 strain with a DNA library and subsequently screening for methylmethane sulfonate (MMS) resistance. Alternately, functional genes from a variety of mammalian species can now be cloned using the system described.

Yeast genes can be cloned by a variety of techniques, including use of purified RNA as hybridization probes, differential hybridization of regulated RNA transcripts, antibody screening, transposon mutagenesis, cross suppression of mutant phenotypes, cross hybridization with heterologous CDNA or oligonucleotide probes, as well as by complementation in *E. coli*.

Minor modifications of the primary amino acid sequence may result in proteins which have substantially equivalent or enhanced activity as compared to the sequence set forth in SEQ. I.D. NO. 2. The modifications may be deliberate, as by site-directed mutagenesis, or may be spontaneous by HRR25 producing organisms. All of these modifications are included in the invention as long as HRR25 activity is retained. Substitution of an aspartic acid residue for a glycine acid residue at position 151 in the sequence shown in SEQ. I.D. NO. 2 identifies the mutant hrr25.

Antibodies provided by the present invention are immunoreactive with the mutant polypeptides and/or the naturally occurring protein kinase. Antibody which consist essentially of numerous monoclonal antibodies with different epitopic specificities, as well as distinct monoclonal antibody preparations are provided. Monoclonal antibody is made from antigen containing fragments of the polypeptide by methods well known in the art (Kohler, G. et al., *Nature* 256:495, 1975; *Current Protocols in Molecular Biology*, Ausubel, F. et al., ed.,1989).

The invention also discloses a method for identifying a composition which affects the activity of a polypeptide having tyrosine kinase activity. The polypeptide is capable of promoting restoration of DNA double-strand break repair activity in host cells containing the hrr25 gene. The composition and the polypeptide are incubated in combination with host cells for a period of time and under conditions sufficient to allow the components to interact, then subsequently monitoring the change in protein kinase activity, for example, by decreased repair of DNA double-strand breaks. The DNA strand breaks are induced, for example, by a radiomimetic agent, such as methylmethane sulfonate, x-rays, or by endonuclease like HO. Other means of inducing double-strand breaks that are well known in the art may be employed as well.

One embodiment of the invention provides a method of treating a cell proliferative disorder associated with or HRR25 or an HRR25-like protein comprising administering to a subject with the disorder, a therapeutically effective amount of reagent which modulates an HRR25-like protein activity. The term "cell proliferative disorder" denotes malignant as well as non-malignant cell populations which differ from the surrounding tissue both morphologically and/or genotypically. Such disorders may be associated, for example, with abnormal expression of HRR25-like protein genes. "Abnormal expression" encompasses both increased or decreased levels of expression as well as expression of mutant forms such that the normal function of HRR25-like genes is altered. Abnormal expression also includes inappropriate temporal expression during the cell cycle or expression in an incorrect cell type. Antisense polynucleotides of the invention are useful in treating malignancies of the various organ systems. Essentially, any disorder which is etiologically linked to altered expression of HRR25-like genes is a candidate for treatment with a reagent of the invention. "Treatment" of cell proliferative disorder refers to increasing or decreasing populations of malignant or non-malignant cells.

As used herein, the term "modulate" envisions the suppression of HRR25-like protein expression or the augmentation of expression. When a cell proliferative disorder is associated with HRR25-like gene overexpression, appropriate reagents such as antisense or binding antibody can be introduced to a cell. This approach utilizes, for example, antisense nucleic acid and ribozymes to block translation of a specific HRR25-like protein mRNA, either by masking that mRNA with an antisense nucleic acid or by cleaving it with a ribozyme. Alternatively, when a cell proliferative disorder is associated with insufficient HRR25-like protein, a sense polynucleotide sequence (the DNA coding strand) or HRR25-like polypeptide can be introduced into the cell by methods known in the art.

As used herein, the term "therapeutically effective" refers to that amount of polynucleotide, antibody or polypeptide that is sufficient to ameliorate the HRR25-associated disorder. "Ameliorate" denotes a lessening of the detrimental effect of the HRR25-associated disorder in the subject receiving therapy.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. This interferes with the translation of the mRNA since the cell will not translate a mRNA that is double-stranded. Antisense oligomers of about 15 nucleotides are preferred, since they are easily synthesized and are less likely to cause non-specific interference with translation than larger molecules when introduced into the target HRR25 producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because ribosomes are sequence-specific, only mRNAS with particular sequences are inactivated.

There are two basic types of ribozymes namely, tetrahymena-type and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that sequence will occur exclusively in the target mRNA species. Consequently, hammerhead-type ribozymes are preferable to tetrahymena-type ribozymes for inactivating a specific mRNA species and longer recognition sequences are preferable to shorter recognition sequences.

The present invention also provides gene therapy for the treatment of cell proliferative disorders which are mediated by HRR25-like polypeptides. Such therapy comprises introducing into cells of subjects having the proliferative disorder, the HRR25-like antisense polynucleotide. Delivery of antisense polynucleotide can be achieved using a recombinant expression vector such as a chimeric virus or a colloidal dispersion system. Disorders associated with under-expression of HRR25 can similarly be treated using gene therapy with nucleotide coding sequences.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting an HRR25-like sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the HRR25-like antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to $\psi 2$, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for HRR25-like antisense polynucleotides comprises a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

The present invention will be better understood upon consideration of the following illustrative examples wherein: Example 1 addresses isolation of hrr25 mutant strains of *Saccharomyces cerevisiae*; Example 2 describes the isolation of HRR25 DNA by complementation screening; Example 3 is drawn to characterization of the DNA and putative amino acid sequence of HRR25; Example 4 addresses microscopic analysis of HRR25 wild type and hrr25 mutant yeast morphology; Example 5 addresses the relationship of the amino acid sequence of HRR25 and three exemplary protein kinases which are not HRR25-like; Example 6 describes the isolation of DNAs encoding two *Schizosaccharomyces pombe* HRR25-like protein kinases; Example 7 is directed to isolation of DNA encoding another *Saccharomyces cerevisiae* protein, NUF1; Example 8 is drawn to isolation of DNAs encoding various eukaryotic species HRR25-like proteins including three human isoforms, CKIα1Hu, CKIα2Hu, and CKIα3Hu; Examples 9 and 10 are respectively directed to determination of casein kinase and both serine-threonine kinase and tyrosine kinase activities for HRR25; Example 11 is drawn to the recombinant expression of HRR25 products and the generation of antibodies thereto; Example 12 relates to the isolation of human CKI isoforms, CKIγ1Hu and CKIγ2Hu; Example 13 addresses isolation of another human isoform CKIδHu; Example 14 describes complementation of yeast CKI mutants with human CKI isoforms; and Example 15 is directed to generation of monoclonal antibodies against peptide fragments of human CKIαHu isoforms.

The following examples are intended to illustrate but not limit the invention. While they are typical of those that might be used, other procedures known to those skilled in the art may alternatively be used.

EXAMPLE 1

Isolation of hrr25

*S. cerevisiae* strain K264-5B (MATα ho ura3 can1$^R$ tyr1 his7 lys2 ade5 met13 trp5 leu1 ade5) was employed for the mutant isolation. The yeast were transformed according to standard procedures with a URA3-based integrating plasmid that contained a GAL1,10regulated HO endonuclease and a transformant was mutagenized to approximately 50% survival with ethyl methanesulfonate (EMS), as described (*Current Protocols in Molecular Biology*, supra). The culture was spread onto glycerol-containing rich medium (Ypg, to avoid petites), colonies were allowed to form at 30° C., and plates were replicated to glucose (HO repressing) and galactose (HO inducing) media. Mutants were identified by their inability to grow on galactose. Approximately 200 mutants were chosen for initial characterization and 62 maintained the gal- phenotype through repeated single colony purification. Among these, many were not complemented by various gal mutants. The remainder (25 mutants) were surveyed for overlapping DNA repair defects by determining sensitivity to ultraviolet (UV) irradiation and to methyl methane sulfonate (MMS). This screening method identified five alleles of known rad mutations and one new mutation. This new mutation hrr25-1 (HO and/or radiation repair), presented severe defects and was studied further.

A recessive DNA repair defect is conferred by hrr25-1 that includes sensitivity to MMS. Hrr25-1 strains also show sensitivity at 5–20 Krad X-irradiation similar to that observed with mutations in the radiation repair genes RAD50 and RAD52 (Cole, et al., *Mol. Cell. Biol.*, 9:3101, 1989). The hrr25-1 strains are no more sensitive to UV irradiation than wild type and are not temperature sensitive for growth at 37° C. Unlike hypo- and hyper-rec rad mutants which have several of the hrr25-1 phenotypes, hrr25-1 strains undergo normal mitotic recombination (Cole, et al., *Mol. Cell. Biol.*, 9:3101, 1989). Spontaneous gene conversion and crossing-over were the same for homozygous hrr25-1 and wild type strains. However, HRR25 is required for the correct completion of meiosis. The hrr25-1 homozygotes showed less than 1% spores (tetranucleate cells) under conditions that produced 75–80% spores in an isogenic wild type strain. The hrr25-1 mutation could be complemented by a number of radiation sensitive mutations (rad6, 50, 52, 54, and 57) that present some of the hrr25 phenotypes, suggesting that hrr25-1 is a newly uncovered rad-like mutation and not one of these previously described genes. These results also indicate that HRR25 plays a role in DNA repair and meiosis, but is not specifically required for the repair of spontaneous mitotic lesions by recombination.

EXAMPLE 2

Isolation of HRR25

The HRR25 gene was obtained by complementing for MMS sensitivity using a yeast genomic library constructed in the plasmid YCp50 (Rose, et al., *Gene*, 60:237, 1987). An hrr25-1 strain, MHML 3–36d (ura3 hrr25), was transformed by standard methods (Nickoloff, et al., *J. Mol. Biol.*, 207:527, 1989) to uracil prototrophy, transformants were amplified on media without uracil and replicated to media containing 0.01% MMS. Among 1200 transformants, a single MMS resistant isolate was identified. Complementation for MMS sensitivity was found to segregate with the plasmid as determined by methods known in the art.

A 12 kb genomic fragment was identified and complementing activity was localized to a 3.1 kb BamHI-SalI fragment by transposon mutagenesis and subcloning. This region complemented DNA repair defects as well as meiotic deficiencies. Gene targeting experiments linked this cloned region to hrr25-1. Transposon insertion mutations within the BamHI-SalI fragment replaced into the cognate HRR25 genomic locus did not complement hrr25-1 for MMS sensitivity, whereas adjacent chromosomal insertions outside the complementing region segregated in repulsion when crossed against hrr25-1.

Mini-Tn10LUK transposons (Huisman, et al., *Genetics*, 116:191, 1987) were used to delineate the approximate location of HRR25 on the 12 kb BamHI-SalI fragment. Insertions located to the left hand 9 kb (of the 12 kb genomic fragment) did not inactivate complementation of hrr25-1 MMS resistance compared with the un-mutagenized plasmid. Two insertions, located near an EcoRV site in the right hand 2 kb inactivated complementation. HRR25 complementation activity was localized to a 3.4 kb SalI fragment. Approximately 300 bp of this fragment (right hand side of the 12 kb) were part of the pBR322 tetracycline resistance gene (between the BamHI site of PBR322-based YCp50). The HRR25 open reading frame spans an internal region across an EcoRV site and two BglII sites within the right terminal 3 kb.

The DNA sequence of the 3.1 kb fragment revealed a centrally located open reading frame of 1482 nucleotide. A transposon insertion mutation in this open reading frame inactivated HRR25 complementation whereas insertions elsewhere in the 12 kb clone did not affect HRR25 complementation. Transposon-mediated disruption of HRR25 also revealed several phenotypes not seen with hrr25-1. As expected, a Tn10-based LUK transposon insertion (Huisman, et al., *Genetics*, 116:191, 1987) into the middle of plasmid-borne HRR25 coding region inactivated complementation for MMS sensitivity. Transplacement of this insertion into the genomic HRR25 gene revealed a severe growth defect in addition to MMS sensitivity and meiotic inviability. This severe growth defect was not observed with hrr25-1 strains. Wild type HRR25 strains doubled in rich media at 30° C. every 80–90 minutes whereas isogenic hrr25::LUK strains and hrr25Δ doubled every 9–12 hours. hrr25-1 had a doubling time of 2–4 hours.

To determine whether the mutant phenotypes revealed by the hrr::LUK disruption allele represent a null phenotype, the entire HRR25 coding sequence was deleted. Briefly, deletion of the HRR25 coding sequence employed a hisG::URA3::hisG cassette (Alani, et al., *Genetics*, 116:541, 1988). The 3.1 kb HRR25 SalI fragment was cloned into pBluescript (Stratagene, La Jolla, Calif.). This plasmid was digested with BglII and the two BglII fragments that span the entire HRR25 gene and its flanking sequences were deleted. Into this deletion was introduced the 3.8 kb BamHI-BglII hisG::URA3::hisG fragment from pNKY51 to create the hrr25Δ allele. SalI digestion yielded a linearized fragment that deleted the entire HRR25 locus. Yeast carrying the deletion-disruption allele (hrr25Δ) showed phenotypes identical to those with the hrr25::LUK allele for all properties examined, including MMS sensitivity, slow growth, and the sporulation defect, indicating that wild-type HRR25 protein is associated with these processes and that the hrr25::LUK allele does not indirectly interfere with DNA repair, growth or sporulation. In direct parallel comparisons, the hrr25::LUK and hrr25Δ alleles behaved identically.

Yeast strain MFH14 (MATα/MATα ura3/ura3) was transformed with BglII-linearized YCp50-HRR25::LUK to uracil prototrophy, heterozygous disruption of HRR25 was verified by Southern blot analysis, the diploid was sporulated by starvation for nitrogen and fermentable carbon sources, tetrads dissected and cells allowed to germinate at 30° C. for 7 days. After a normal germination period of 2 days, the severe growth defect of hrr25: :LUK suggested that the deletion of HRR25 was lethal. However, microscopic examination of segregants revealed that hrr25::LUK germinating cells grew slowly and in every case examined (20/20 tetrads), slow growth, MMS sensitivity, and uracil prototrophy co-segregated. A color variation was seen with diploid MFH14 segregants, due to mutations in adenine biosynthesis. MFH14 is ade5/ADE5 ade2/ade2. An ade5/ade2 strain was white, while an ADE5/ade2 strain was red.

EXAMPLE 3

Sequence and Structure of the HRR25 GENE

DNA sequencing of both strands of the HRR25 gene was done by uni-directional deletions employing Sequenase (USB, Cleveland, Ohio) and Exo-Meth (Stratagene, La Jolla, Calif.) procedures as described by the manufacturers. DNA and deduced amino acid sequences are set out respectively in SEQ. I.D. NOs. 1 and 2. FIG. 1A, shows the alignment of the amino acid sequences for HRR25, CDC28, KSS1, and RAF1. FIG. 1B shows a schematic representation of the structure of HRR25. The protein kinase homology is represented by a shaded region while the P/Q rich region is indicated by cross-hatchings. The mutant, hrr25, can be distinguished from HRR25 by one amino acid substitution. At position 151, an aspartic acid is substituted for glycine.

The predicted translation product of HRR25 revealed an unexpected feature for a rad-like DNA repair function. HRR25 contains the hallmark signatures of sequence homology with the catalytic domain of serine/threonine protein kinase superfamily members (Hanks, et al., *Science*, 241:42, 1988). For comparison, the HRR25 translation product was aligned with the catalytic domains for two subgroups of yeast protein kinases, the CDC28/cdc2 group and the KSS1/FUS3 group. Located between amino acids 15 and 30 is a region that contains the conserved GXGXXG region. Just C-terminal to this region is a conserved lysine and glutamic acid present in most known kinases. These regions are thought to function in the nucleotide binding and phosphotransfer steps of the kinase reaction (Hanks, et al., *Science*, 241:42,1988). Between amino acid residues 120 to 150 are regions containing the HRD and DFG motifs, also found in most protein kinase family members. In addition, sequence examination of all known serine/threonine kinases indicates that HRR25 shares some additional similarities with the Raf/PKS/mos subgroup (Hanks, et al., *Science*, 241:42, 1988). The strongest homologies can be found in areas around the GXGXXG, DFG, and DXXSXG conserved regions in protein kinase catalytic domains.

The functional relevance of the observed sequence similarity between HRR25 and protein kinases was studied by altering specific residues within the HRR25 kinase domain and examining the phenotypic consequences of these changes. A lysine at position 38 (Lys $^{38}$) was mutated to an arginine residue by site directed mutagenesis, by methods known in the art. The mutagenic oligonucleotide SEQ. I.D. NO. 22 was:

5'-CCTGATCGATTCCAGCCTGATCGCTACTTCTTCACCACT-3'.

Lys$^{38}$ in HRR25 corresponds to the lysine found in all known protein kinases, and this subdomain is involved in ATP binding. Mutations at the conserved lysine in protein kinases such as v-src, v-mos, and DBF2 inactivate these proteins. The mutant hrr25-Lys$^{38}$ allele was incapable of complementing hrr25-1, hrr25::LUK, and hrr25Δ alleles for all properties examined, an indication that the HRR25 kinase domain is required for in vivo function of HRR25.

The predicted HRR25 translation product (SEQ. I.D. NO. 2) has a number of notable features outside the region of homology to protein kinase catalytic domains. For example, the last 100 amino acids is proline and glutamine rich, containing 50 of these residues. Other proteins with regions rich in these two amino acids include the transcription factors Sp1, jun, and M4P2, steroid hormone receptors, the *S. pombe* ran1 kinase, and mak-male germ cell-associated kinase (Courey, et al., *Cell*, 55:887, 1988; Bohmann, et al., *Science*, 238:1386, 1987; Roussou, et al., *Mol. Cell. Biol.*, 8:2132, 1988; Arriza, et al., *Science*, 237:268, 1987; Matsushime, et al., *Mol. Cell. Biol*, 10:2261, 1990). In the case of Sp1 and jun, the proline-glutamine regions are involved in transactivation, whereas the P/Q region in the human mineralocorticoid receptor is thought to serve as an intramolecular bridge. This proline-glutamine region in HRR25 might function as a structural feature for substrate interaction, or for subcellular localization. Also, the glutamine richness of this region is similar to the opa or M-repeat seen in the Drosophila and Xenopus Notch/Xotch proteins (Wharton, et al., *Cell*, 40:55, 1985; Coffman, et al., *Science*, 249:1438, 1990). The function of the opa repeat is not certain, but it is found in several Drosophila genes. Lastly, the sequence TKKQKY at the C-terminal end of the region homologous to protein kinases is similar to the nuclear localizing signal of SV40 large T antigen and yeast histone H2B (Silver, et al., *J. Cell. Biol.*, 109:983, 1989; Moreland, et al., *Mol. Cell. Biol*, 7:4048, 1987).

EXAMPLE 4

Microscopic Analysis of Germinating and Proliferating hrr25 Cells

Photomicrographs of HRR25 and hrr25::LUK colonies were taken after germination on rich medium. An MFH14 hrr25::LUK heterozygous transformant was dissected onto a thin film of YPD rich medium on a sterilized microscope slide and segregants were allowed to germinate under a coverslip by incubating the slide in a moist 30° C. chamber. Photographs of colonies were taken after 2 days of growth. Phase contrast and DAPI staining of proliferating HRR25Δ and hrr25::LUK cells were compared. Cells were inoculated into YPD rich medium and grown at 30° C. to a mid-log density of $1–3 \times 10^7$ cells/ml, briefly sonicated to disrupt clumps, fixed with formaldehyde, and stained with DAPI (Williamson, et al., *Meth. Cell. Biol.*, 12:335, 1975). Many cells with hrr25::LUK lacked DAPI stainable nuclei.

Microscopic examination of germinating and actively growing mid-log phase hrr25::LUK cells revealed aberrant cellular morphologies. Transposon disruption of HRR25 resulted in large cells, and 25–40% of cells were filamentous or extended. DAPI nuclear staining (Williamson, et al., *Meth. Cell. Biol.*, 12:335, 1975) of mid-log populations showed that orderly cell cycle progression in hrr25 mutants was lost. There were a large number of cells lacking DAPI-stainable nuclei which, by single cell manipulations proved to be inviable. Consistent with this nuclear segregation defect, the plating efficiency of hrr25::LUK haploids was also reduced to 75–80% of wild type. However, this reduction in plating efficiency is insufficient to account for the severe growth rate reduction. Plating efficiency was measured from mid-log phase cells by comparing the efficiency of colony formation on rich medium relative to the total number of cells determined by hemocytometer count. Cell populations were analyzed for DNA content distribution by flow cytometric analysis following staining with propidium iodide as described (Hutter, et al. *J. Gen. Microbiol.*, 113:369, 1979). Cell sorting analysis showed that a large number of the cells in a haploid hrr25::LUK population were delayed in the cell cycle and exhibited G2 DNA content, but the population was not arrested uniformly in the cell cycle.

EXAMPLE 5

Sequence Comparison of HRR25 with CDC28, KSS1, and RAF1

The predicted translation product of HRR25 (SEQ. I.D. NO. 2) was compared with the catalytic domains of several members of the serine/threonine protein kinase superfamily. Initial sequence comparisons employed the UWGCG programs (Devereux, et al., *Nuc. Acids. Res.*, 12:387, 1984), whereas subgroup comparisons used the methods of Hanks, et al., supra. HRR25 contains all eleven subdomains described by Hanks, et al., supra. Structurally similar groupings were compared in the sequence comparisons. These included nonpolar chain R groups, aromatic or ring-containing R groups, small R groups with near neutral polarity, acidic R groups, uncharged polar R groups, and basic polar R groups.

CDC28 and KSS1 represent members of two subgroups of serine/threonine protein kinases in yeast. CDC28 is involved in cell cycle regulation while KSS1 acts in the regulation of the yeast mating pathway. HRR25 shows 21% identity and 41% similarity to CDC28 and 19% identity and 43% similarity to KSS1 (FIG. 1A). HRR25 shows highest similarity to members of the Raf1/PKS/Mos family of protein kinases. Through the catalytic domain, HRR25 shows 30% identity and 49% similarity to Raf1.

EXAMPLE 6

Identification, Isolation, and Analysis of *Sc. pombe* Hhp1+ and Hhp2+ Genes A. Isolation of the Hhp1+ and Hhp2+ Genes The clones were isolated by a two-pronged approach: i) DNA-based screening methods; and ii) direct complementation in *S. cerevisiae* hrr25 mutant strains. Two genes were identified (Hhp1+ and Hhp2+—so named for HRR25 Homologue from *Schizosaccharomyces pombe*). Expression of Hhp1+ in *S. cerevisiae* hrr25 mutants fully rescued all mutant defects. Expression of Hhp2+ in *S. cerevisiae* also rescued, to varying degrees, the defects associated with hrr25 mutations.

DNA-based amplification of HRR25-like DNAs from *Sc. pombe* genomic and CDNA sequences prepared according to Fikes, et al. (*Nature*, 346:291–293, 1990) was conducted using polymerase chain reaction with the following partially degenerate oligonucleotide primers:

(1) Primer No. 4583, (SEQ. ID. NO. 13) representing top strand DNA encoding residues 16 through 23 of HRR25; [1 nmol/5 µl], $T_m=52°$ C.;

(2) Primer No. 4582 (SEQ. ID. NO. 14) representing top strand DNA encoding residues 126 through 133 of HRR25; [1.5 nmol/5 µl], $T_m=54°$ C.;

(3) Primer No. 4589 (SEQ. ID. NO. 15) representing bottom strand DNA encoding residues 126 through 133 of HRR25; [0.5 nmol/5 µl], $T_m=54°$ C.;

(4) Primer No. 4590 (SEQ. ID. NO. 16) representing bottom strand DNA encoding residues 194 through 199 of HRR25; [2 nmol/5 µl], $T_m=38°$ C.

Two series of amplifications were conducted using Perkin Elmer Automated apparatus; a first series using HRR25-based primer Nos. 4583 and 4589 and a second series employing all four of the primers. In the first series, 30 cycles of denaturation (94° C., 1 min), annealing (48° C., 1 min), and extension (66° C., 3 min) were performed and in a final cycle, the extension time was extended to 5 min. Reaction products were sized on an agarose gel revealing a prominent band of the expected size of about 306 bp. In the second series of amplifications, 30 cycles were carried out as above except that annealing and extension were carried out at 35° C. and 60° C., respectively. Three major products of the expected sizes (513 bp, 180 bp, and 306 bp) were developed in both genomic and CDNA libraries and were purified by preparative agarose gel electrophoresis.

Products were cloned into M13mp19 and sequenced by the dideoxy method (Maniatis, et al., *Molecular Cloning: A Laboratory Manual*, 1982). Two classes of sequences were identified. A representative clone from each class was radiolabelled with $^{32}$p by random primed cut labeling to a specific activity of $10^6$ cpm/µg (Maniatis, et al., supra) and used as a hybridization probe to isolate full length CDNA clones and to prove yeast genomic DNA in Southern blots and total RNA on Northern blots. Hybridization was carried out for 16 hours in a buffer containing 6 x SSPE, 0. 1% SDS, 5% dextran sulfate. Two genes were identified and designated Hhp1+ and Hhp2+ for HRR25 Homologues from *Sc. pombe*.

For Hhp1+, 7 clones were identified (6 partial and 1 full length clone). For Hhp2+, 2 full length clones were identified. Both Southern and Northern analysis confirmed that these clones were from separate genes. These genes were sequenced using standard dideoxy method (Maniatis, et al., supra). The nucleotide and deduced amino acid sequences for Hhp1+ are set out in SEQ. ID. NOS. 3 and 4; the nucleotide and deduced amino acid sequences for Hhp2+ are set out in SEQ. ID. NOS. 5 and 6.

B. Functional analysis of Hhp1+ and Hhp2+ in S. cerevisiae hrr25 mutants.

Sc. pombe Hhp1+ and Hhp2+ cDNAs were cloned in a location which placed them under the control of the S. cerevisiae alcohol dehydrogenase-1 (ADH1) promoter in a URA3-based vector pDB20 to allow for expression in S. cerevisiae (Fikes, et al., supra). These resulting clones were analyzed for their ability to alter/modify the suppress phenotypes associated with the hrr25-1 mutation and the hrr25Δ mutation following transformation into appropriate yeast strains by standard methods (Ito, et al., J. Bacteriol. 153:163, 1983). Transformants were analyzed for their ability to overcome defects associated with the hrr25 mutations (Hoekstra, et al., Science, 253:1031, 1991). Hhp1+ expression fully complemented hrr25-associated defects and was indistinguishable from wild type HRR25 in all analyses. Complementation was analyzed for the effect on DNA repair, cell cycle progression, cellular morphology, and sporulation. Hhp2+ complemented to a lesser degree than Hhp1+ (its complementation level was 50%–75% that of bona fide HRR25). The alteration of hrr25-associated phenotypes was dependent upon the transformed yeast strains containing both a complementing Sc. pombe Hhp plasmid and having hrr25 mutations.

The degree of amino acid homology between HRR25 protein and Hhp1+ protein is 73% through the kinase domain. The degree of similarity, which considers the presence of similar as well as identical amino acids, is greater than 85%. The amino acid identity of HRR25 protein and Hhp2+ protein is 63% with a percent similarity score of 80%. The intraspecies comparison of Hhp1+ protein to Hhp2+ protein is 72% identity. This structural and complementation analysis clearly indicates that these Sc. pombe clones are functional homologues of the S. cerevisiae HRR25. Such a high degree of relatedness is not seen with any other group of protein kinases. As a measure of comparison here, bona fide functional homologues (i.e., cdc2 protein kinases from S. cerevisiae, Sc. pombe, and humans) show 40%–45% identity. Any two randomly compared protein kinases, regardless of whether the comparison is inter-or intra-species show a degree of identity of about 20%–25%.

C. Disruption and mutation of Hhp1+ and Hhp2+ in Sc. pombe

Mutations that inactivate or reduce the protein kinase activity of HRR25 in S. cerevisiae result in a wide variety of phenotypes including: sensitivity to various forms of DNA damage, severe cell cycle delay, sensitivity to drugs that affect cell cycle progression (e.g., caffeine), sensitivity to agents that affect microtubule integrity (e.g., benomyl), and sensitivity to agents that affect the integrity of replicating DNA (e.g., hydroxyurea).

Similarity, in Sc. pombe, inactivation of the Hhp1+ and the Hhp2+ genes to reduce or abolish the encoded protein kinase activity resulted in cellular phenotypes that mimicked hrr25 mutations. For example, deletion of the Hhp1+ gene resulted in a cell cycle delay and aberrant cellular morphology, in sensitivity to DNA damaging agents like MMS, and in sensitivity to benomyl and hydroxyurea. Deletion of the Hhp2+ gene resulted in caffeine sensitivity, benomyl sensitivity, and hydroxyurea sensitivity, amongst other defects.

The Hhp1+ gene was disrupted as follows: CDNA was subcloned into the Sc. pombe vector pHSS19 (Hoekstra et al., Meth. Enzymol., 194:329, 1991), which was digested with NheI-EcoRI. The Sc. pombe URA4 gene was inserted resulting in deletion of the Hhp1+ kinase domain. Sc. pombe was transformed by standard methods (Moreno, et al., Meth. Enzymol, 194:795, 1991) with the linearized DNA from the resulting plasmid construction. Stable transformants were identified and haploid hhp1Δ strains were verified by standard methods (Moreno, et al., Maniatis, et al.).

The Hhp2+ gene was disrupted as follows: the Hhp2+ CDNA was cloned into the Sc. pombe based vector, plasmid pHSS19, and was disrupted by transposon shuttle mutagenesis using the. mini-Tn3 transposon mTn3Leu2 (Hoekstra, et al., Meth. Enzymol supra.). Sc. pombe was transformed by standard methods with the linearized DNA from the resulting plasmid construction. Stable transformants were identified and haploid hhp2Δ strains were verified by standard methods (see above).

Standard physiological methods as described for S. cerevisiae HRR25 (Hoekstra, et al., Science 253:1031, 1991) were employed to characterize hhp mutant strains. Phenotypic analysis revealed that both hhp1and hhp2 mutants showed defects previously seen in hrr25 mutants, including sensitivity to various DNA damaging treatments that include MMS treatment and X-ray treatment.

The foregoing substantiates that Hhp1+ and Hhp2+ are isoforms of S. cerevisiae HRR25 protein kinase. These three protein kinases show high levels of sequence identity. In addition, mutations that inactivate these kinases result in very similar defects in widely divergent organisms.

D. Complementation of Sc. pombe mutant strains with the S. cerevisiae HRR25 gene.

To show that Sc. pombe hhp mutants prepared as described above, were identical to S. cerevisiae hrr25 mutants and to show that HRR25-like protein kinases with greater than 35% amino acid identity are functional homologues, the S. cerevisiae HRR25 gene was introduced into a Sc. pombe expression vector and transformed into Sc. pombe hhp mutants. The DNA sequence at the HRR25 initiating methionine was changed into an NdeI site, (a silent coding alteration that maintains the reading frame but allows the HRR25 gene to be introduced into appropriate Sc. pombe plasmids). This was done by a site-directed DNA change was made in the S. cerevisiae HRR25 gene by standard methods using a commercially available system (Bio-Rad, Cambridge, Mass.). The altered HRR25 gene was ligated into the Sc. pombe expression plasmid, pREP 1 (Maundrell, K. J., Biol. Chem. 265:10857, 1990), at an NdeI site and the resulting construction was transformed by standard methods into Sc. pombe hhp mutants. Expression of HRR25 in Sc. pombe mutant strains resulted in complementation of the mutant defects as evaluated by physiological methods described by Hoekstra, et al. (Science, supra).

EXAMPLE 7

Isolation and Characterization of Yeast HRR25-like Genes

Isolation of additional HRR25-like genes from S. cerevisiae was accomplished by performing DNA-based amplification of genomic DNA from an S. cerevisiae strain lacking HRR25 coding sequences [Strain 7D of DeMaggio, et al.

(Proc. Natl. Acad. Sci., USA, 89:7008–7012, 1992, incorporated herein by reference) thereby eliminating the chance of obtaining HRR25 sequences from the amplification. The primers and amplification conditions were as in Example 6.

The resulting amplification products were cloned in M13mp19 and sequenced by dideoxy chain termination methods. Three unique classes of amplified products were identified. Two of these products respectively corresponded to the YCK1/CKI2 and YCK2/CKI1 genes of Robinson, et al. (Proc. Natl. Acad. Sci. USA, 89:28–32, 1992) and Wang, et al. (Molecular Biology of the Cell, 3:275–286, 1992). The third gene product was designated "NUF1" (for Number Four). The amplified products corresponding to NUF1 were radiolabelled as described in Example 6 and used to screen a yeast YCp50-based genomic library (ATCC, Rockville, Md.). Eight clones were identified and one of these clones included approximately 4 Kb HindIII fragment containing the NUF1 hybridizing gene. Southern analysis revealed that NUF1 is a separate gene from HRR25, YCK1/CKI2, and YCK2/CKI1. The HindIII fragment was sequenced and revealed a protein kinase with about 65% identity to HRR25 through its protein kinase domain. The DNA and deduced amino acid sequences for NUF1 are set out in SEQ. ID. NOS. 23 and 24.

To further characterize the NUF1 gene, the HindIII fragment was subcloned into the yeast plasmid YEplac112 [Gietz and Sugino, Gene 74:527–541 (1988)]. The resulting construct was transformed into the hrr25Δ deletion strain 7d and NUF1 was found to complement for hrr25Δ mitotic defects (e.g., NUF1 complemented for slow growth defect, aberrant morphology defect, DNA damaging agent sensitivities). Furthermore, a null mutant allele of NUF1 was constructed by transposon shuttle mutagenesis and strains lacking the NUF1 gene product were found to have hrr25Δ mutant-like defects. In particular, like hrr25Δ mutants, NUF1 mutants showed slower mitotic growth rates and increased sensitivity to DNA damaging agents like MMS, UV, and X-irradiation.

EXAMPLE 8

Identification and Isolation of Human HRR25-like Genes

Oligonucleotides derived from amino acid sequences described above in Example 6A were used to amplify cDNAS from the following sources: Arabidopsis thaliana, Drosophila melanogaster, Xenopus, chicken, mouse, rat, and human HeLa cells. These cDNAS were obtained from reverse transcribed mRNA (Maniatis, et al., supra) or from commercially-available cDNA libraries (Stratagene, La Jolla, Calif., and Clonetech, Palo Alto, Calif.) Amplification products of similar migration size to those obtained from S. cerevisiae HRR25 and Sc. pombe, Hhp1+ and Hhp2+ genes were observed in 1.0% Agarose gels (Maniatis, et al., supra). This result indicated that HRR25-like genes exist in all species examined.

Isolation of full length DNAs encoding human HRR25-like protein kinases was accomplished by PCR amplification of human genomic DNA using unique sequence oligonucleotide primers based on portions of a bovine brain casein kinase I cDNA which had been reported in Rowles, et al. (Proc. Natl. Acad. Sci. USA, 88:9548–9552, 1991) to encode a mammalian protein that was 60% homologous to HRR25 over its catalytic domain.

A variety of primers were prepared and used in pairwise fashion including:

(1) Primer JH21 (SEQ. ID. NO. 17) representing bovine top strand DNA bases 47–67;

(2) Primer JH22 (SEQ. ID. NO. 18) representing bovine top strand DNA bases 223–240;

(3) Primer JH29 (SEQ. ID. NO. 19) representing bovine top strand DNA bases 604–623;

(4) Primer JH30 (SEQ. ID. NO. 20) representing bovine top strand DNA bases 623–604; and (5) Primer JH31 (SEQ. ID. NO. 21) representing bovine top strand DNA bases 835–817.

DNA amplification with combination of oligonucleotides JH21/JH30, JH22/JH30, and JH29/JH31 were carried out for 30 cycles with denaturation performed at 94° C. for 4 min for the first cycle and for 1 min for the remaining cycle annealing at 50° C. for 2 min and extension at 72° C. for 4 min. Products of the expected size from the three amplifications were purified on preparative acrylamide gels and labeled with $^{32}$P using random nick translation (to a specific activity between $7\times10^6$ cpm/µg and $1.4\times10^7$ cpm/µg. The labelled probes were employed as a group to screen a commercial human fetal brain cDNA library (Stratagene). Hybridization was carried out for 16 hours at 65° C. in a hybridization buffer containing 3 x SSC, 0.1% Sarkosyl, 10 x Denhart's solution and 20 mM sodium phosphate (Ph 6.8). Three washes at 65C in 2 x SSC, 0.1% SDS were performed. Approximately $1.5\times10^6$ plaques were screened on 30 plates using duplicate filters. Six strong positive clones were isolated, purified and converted to plasmid form according to procedures recommended by the supplier of the library. Restriction digestion revealed the following insert sizes for the six clones: clone 35A1, 1 kb; clone 35B1, 1.4 kb; clone 41A1, 3.7 kb; clone 42A1, >4 kb; clone 47A1, 3.35 kb; and clone 51A1, 2.75 kb. All six inserts contained sequences which could be aligned with both the DNAs and deduced protein sequence of the bovine CKIα gene. The abbreviated, partial cDNA clones 35A1 and 35B1 were not further analyzed. Clones 41A1 and 42A1 were identical except for size. Clones 42A1, 51A1, and 47A1 were redesignated as CKIα1Hu, CKIα2Hu, and CKIα3Hu. The DNA and deduced amino acid sequences of the inserts are set out in SEQ. ID. NOS. 7 and 8; 9 and 10; and 11 and 12, respectively. The deduced amino acid sequence for CKIα1Hu was identical to the reported bovine CKIα sequence. Table 1, below sets out differences in nucleotides between the bovine and human DNAs, numbered from the first base in the initiation codon, ATG.

TABLE 1

| COMPARISON OF HUMAN AND BOVINE CKIα DNA | | |
|---|---|---|
| Position | Bovine | Human |
| +9 | C | T |
| +27 | A | T |
| +93 | T | C |
| +126 | G | A |
| +147 | C | T |
| +186 | A | G |
| +255 | T | C |
| +258 | C | T |
| +261 | G | A |
| +267 | T | C |
| +279 | T | G |
| +285 | C | T |
| +291 | T | C |
| +372 | C | T |
| +540 | T | C |
| +555 | T | C |

TABLE 1-continued

COMPARISON OF HUMAN AND BOVINE CKIα DNA

| Position | Bovine | Human |
| --- | --- | --- |
| +558 | G | A |
| +591 | A | G |
| +594 | A | G |
| +669 | A | G |
| +687 | A | G |
| +690 | G | A |
| +705 | A | G |
| +729 | A | G |
| +731 | C | T |
| +753 | A | G |
| +771 | C | G |
| +798 | G | A |
| +816 | G | A |
| +828 | C | T |
| +867 | T | C |
| +870 | C | T |
| +936 | A | C |

The CKIα3Hu DNA also includes an insertion of 84 bases at position +454 in the coding sequence providing an intermediate extension of the CKIα2Hu expression product by 28 amino acids. This DNA insert is not present in the bovine gene, but it encodes an amino acid sequence insert which Rowles, et al. designated as CKI-alpha-L. The CKIα2Hu and CKIα3Hu DNAs insertion at position +971 of the CKIα1Hu DNA. This insertion is not found in any of the bovine sequences and encodes an extension of the 13 amino acids adjacent the carboxy terminal. The last two codons of the CKIα3Hu sequences differ from any of the bovine sequences or the sequences of CKIα1Hu and CKIα2Hu, causing the CKIα3Hu expression product to terminate with a lysine, rather than a phenylalanine as found in all the other bovine and human casein kinase I sequences. The 3' flanking sequence of CKIα3Hu DNA differs significantly from that of CKIα1Hu and CKIα2Hu.

FIG. 2 provides an alignment of the catalytic domain amino acid sequences of HRR25-like proteins whose DNAs were isolated in the above illustrative examples, including HRR25, Hhp1+, Hhp2+, CKIα1Hu, CKIα2Hu, and CKIα3Hu as well as YCK1/CKI2, and YCK2/CKI1. Note that with the exception of the CKIα3Hu intermediate insert and the carboxy terminal region inserts of CKIα2Hu and CKIα3Hu, the sequences of the three human products are identical. "Common" residues are indicated in the Figure where at least 3 of the seven residues are identical at the corresponding position (the human sequences being taken as a single sequence).

Like Hhp1+ and Hhp2+, the three human HRR25-like protein kinases showed very high degrees of amino acid identity to the HRR25 gene product (68%), establishing that these human clones were enzymatic isoforms of the yeast HRR25 gene. The alignment of HRR25, Hhp1+, Hhp2+, and the human complementing-like kinase isoforms show that these enzymes share a number of primary structural features that indicate that these enzymes provide comparable activities in different species. This conclusion is reached based on several lines of evidence. First, all enzymes share the common primary sequence identifiers characteristic of protein kinases. Second, the enzymes share high degrees of amino acid identity in regions of the protein kinase domain that are not conserved in unrelated protein kinases. Finally, these enzymes share regions of identity in the kinase domain which regions differ in primary sequence from other protein kinases, but are identical among the members of this isoform grouping. For example, greater than 95% of all known protein kinases have a so-called A-P-E sequence (Alanine-Proline-Glutamate) approximately two-thirds of the way through the kinase domain. HRR25-like protein kinases lack the A-P-E sequence and have instead a S-I/V-N sequence (Serine-Isoleucine or Valine-Asparagine). Based on this primary sequence comparison, between known protein kinases and the protein kinases of the invention from evolutionarily divergent organisms, these enzymes of the invention are isoforms of HRR25 protein kinase.

EXAMPLE 9

Comparison of HRR25 with a Casein Kinase

In all eukaryotes examined, two of the major protein kinases are casein kinase I and II (CKI and CKII, respectively). These enzymes have been found in all cell types and species examined. Both enzymes recognize Ser/Thr residues in an acidic environment in the substrate. These two protein kinases are found throughout the cell and their activities have been purified from or found to be associated with cytoplasmic fractions, membranes, nuclei, mitochondria, and cytoskeleton. CKII is predominantly a nuclear enzyme, but similar studies have yet to be described for CKI.

To determine whether HRR25 gene product might function as a casein kinase, the ability of HRR25-containing immunoprecipitates to phosphorylate casein was studied. HRR25-containing immunoprecipitates from yeast were incubated with casein and phosphorylated proteins were examined.

Yeast extracts were prepared by physical disruption. Equal volumes of a cells were suspended in lysis buffer and acid-washed 0.5 mm beads were mixed, 30 second bursts were interspersed with 1 min on ice, and the extent of disruption was followed microscopically. Lysis buffer contained 10 Mm sodium phosphate (Ph 7.2), 150 Mm NaCl, 1% Nonidet P-40, 1% Trasylol, 1 Mm DTF, 1 Mm benzamidine, 1 Mm phenylmethyl sulfonyl fluoride, 5 Mm EDTA, pepstatin (1 ug/ml), Pepstatin A (2 ug/ml), leupeptin (1 ug/ml), 100 mM sodium vanadate, and 50 Mm NaF. Extracts were clarified by a 100,000 x g centrifugation for 30 min., made to 50% (vol/vol) with glycerol, frozen in liquid nitrogen, and stored at −70 degrees C. Little loss in protein kinase activity was seen in frozen extracts over several months.

Immune complex protein kinase assays were performed on the extracts according to the methods described in Lindberg, et al. (Mol. Cell. Biol. 10:6316, 1991). Frozen extracts were diluted to 25% glycerol with lysis buffer or fresh extracts were used directly. Extracts were precleared with preimmune serum and protein A-Sepharose, and then treated with immune serum (obtained as described in Example 11, infra, from immunization of rabbits with E. coli-derived type-HRR25 fusion products). HRR25 kinase-containing immune complexes were precipitated with protein A-Sepharose. Immune complexes were washed four times with lysis buffer and twice with kinase buffer containing 15 Mm Hepes (Ph 7.4), 100 Mm NaCl, and 10 Mm MgCl$_2$.

Reaction mixtures of HRR25 immunoprecipitates and heat-treated casein (300 ng/20 ul reaction volume) were incubated at 30 degrees C for 5–10 min and contained 10 µCi of gamma-$^{32}$P-ATP per 20 ul reaction volume. Reactions were stopped by the addition of SDS and EDTA, boiled in SDS/PAGE sample buffer and resolved in 10% gels.

Phosphoamino acid analysis was as described (Hunter et al., *Proc. Natl. Acad. Sci. USA* 77:1311, 1980).

Immunoprecipitates from HRR + strains were able to phosphorylate casein. To verify that the appropriate amino acids were phosphorylated, the phosphoamino acid composition of the HRR25-phosphorylated casein was examined by phosphoamino acid analysis. Samples were resolved by two-dimensional electrophoresis at Ph 1.9 and Ph 3.5. Consistent with mammalian CKI specificity, serine and threonine residues were phosphorylated. HRR25 phosphorylated serine residues on casein 3-fold greater than threonine residues. Similarly, the autophosphorylation of HRR25 in immune complexes in vitro occurred on serine and threonine residues. Coupled with the high degree of sequence identity, these results suggest that HRR25 might be a CKI isoform.

To extend and confirm that HRR25 immunoprecipitates from yeast could phosphorylate casein, several experiments were performed. HRR25 immunoprecipitated from *E. coli* strains expressing HRR25 (See Example 11) also showed casein kinase activity, whereas *E. coli* extracts lacking HRR25 protein did not phosphorylate casein. HRR25-containing baculovirus constructs produced casein kinase activity in immunoprecipitates. Wild-type baculovirus-infected cells showed (0.5% casein kinase activity under comparable conditions. The protein kinase activity from S19 cells expressing HRR25 protein was sensitive to the same conditions that reduced or inactivated the HRR25 protein activity from yeast extracts. The observations that HRR25-dependent casein kinase activity was present in immunoprecipitates from *E. coli* cells expressing wild-type HRR25, in insect cells infected with HRR25-containing baculovirus, and in wild-type but not hrr25Δ mutants indicated that the HRR25 gene product could function as a casein kinase and that the casein kinase activity in HRR25 protein-containing immunoprecipitates was due to HRR25 gene product.

EXAMPLE 10

Analysis of Protein Kinase Activity of HRR25-like Proteins

Because the predominant protein kinase activity in *E. coli* is histidine kinase, rather than serine/threonine or tyrosine kinase, those procaryotic cells provide a system for examination of HRR25-like protein kinase activities which is not compromised by presence of endogenous kinases. Both HRR25 and Hhp1+ DNAs were, therefore, expressed in the IPTG-inducible T7 gene 10-based commercial expression system (Invitrogen, San Diego, Calif.) using *E. coli* strain BL21 (DE3) which contains an IPTG-inducible T7 RNA polymerase and T7 lysozyme gene. See, DeMaggio, et al., *Proc. Natl. Acad. Sci. USA*, 89:7008–7012, (1991). In a first series of experiments, *E. coli* lysates were prepared by inducing mid-log phase cells with IPTG for 2 hours, pelleting the cells, and preparing extracts by a freeze-thaw method using buffers described in DeMaggio, et al., supra. Extracts were electrophoresed in polyacrylamide gels, transferred to nylon-based support membranes, and probed by Western analysis with antibodies directed against phosphotyrosine (UBI, Lake Placid, N.Y.). These procedures revealed that HRR25 and Hhp1+ expressing cells contained novel tyrosine phosphorylated proteins not observed in control cells (transformed with the vector alone or with kinase inactive mutants). In a second experiment, the HRR25 and Hhp1+-containing *E. coli* strains were examined for tyrosine-phosphorylated protein by a sensitive and accurate radiolabelling and phosphoamino acid procedure. To do this experiment, cells were induced with IPTG and grown in the presence of $^{32}$P-orthophosphate. Radiolabelled extracts were prepared by the freeze-thaw method, electrophoresed in polyacrylamide gels, and the gels were examined by autoradiographic methods. Novel phosphoproteins were observed in the strains expressing HRR25 and Hhp1+, but not in the above controls. Phosphoproteins were examined by extracting and hydrolyzing the proteins from the gels using standard methods (Boyle, et al., *Meth. Enzymol*, 201:110, 1991). These experiments verified that HRR25 and Hhp1+ could phosphorylate tyrosine, serine, and threonine residues on protein substrates.

EXAMPLE 11

Recombinant Expression of HRR25 Products and Generation of Antibodies Thereto Two different plasmid constructions were developed for expression of HRR25 DNA in *E. coli* to generate immunogens useful in preparation of anti-HRR25 antibodies.

The first plasmid construction involved plasmid pATH according to Koerner et al., *Meth. Enzmol.*, 194:477–491 (1991). An approximately [606] base pair DNA fragment was isolated from the HRR25 open reading frame by Bgl II digestion and this fragment (which encodes amino acid residues 275–476) was ligated into pATH which had been digested with BamHI. The resulting plasmid encoded a fusion protein comprising the *E. coli* TrpE gene product at its amino terminus and a carboxy terminal fragment of HRR25 at its carboxyl terminus.

Inclusion bodies were isolated from *E. coli* DH5α (Bethesda Research Laboratories, Bethesda, Md.) host cells transformed the plasmid using lysis buffers as described in Koerner et al., supra, and were purified by polyacrylamide gel electrophoresis. The gel purified materials were then employed in the immunization of rabbits by subcutaneous injection as recommended by Harlow, et al., *Antibodies: A Laboratory Manual*, Cold Spring Harbor Laboratory, Cold Spring Harbor, N.Y. (1988), using gel purified products with complete Freund's adjuvant for primary injections and incomplete Freund's adjuvant for subsequent injections. Serum reactivity was followed by Western blotting against the gel purified antigen. Affinity purification of serum antibodies was effected using the *E. coli*-produced antigen immobilized on a nitrocellulose membrane support.

EXAMPLE 12

Isolation of CKIγ1Hu and CKIγ2Hu

Additional human HRR25-like protein kinase encoding DNAs were isolated by combined DNA amplification and library screening methods. Oligonucleotides based on conserved regions in HRR25-like protein kinases were used to amplify DNA segments for use as probes in screening human a cDNA library. Redundant oligonucleotides of the sequence

5'-GAR YTI MGI YTI GGI AAY YTI TA-3'  (SEQ ID NO. 28)

and

5'-GTY TTR TTI CCI GGI CKI CCI AT-3'  (SEQ ID NO. 29)

(where G, A, T, and C=standard nucleotides and R=A and G; Y=C and T; I=Inosine; M=A and C; and K=G and T) were used to amplify an approximately 540 nucleotide from a human fetal brain cDNA library (Clonetech). Amplification conditions used 200 Mm Tris.Hcl (Ph 8.2), 100 Mm KCl, 60 Mm (NH4)2SO4, 15 Mm MgCl2, 1% Triton X-100, 0.5 μM of each primer, 100 ng library DNA template, 200 μM dNTPs and 2.5 U polymerase. The reactions were performed for 30 cycles. Reactions were started with a 4 minute treatment at 94° C. and all cycles were 1 minute at 94° C., 2 minutes at 5° C. for annealing, and 4 minutes at 72° C. for extension.

The amplification reaction was electrophoresed through a 1% agarose gel and the region corresponding to approximately 540 base pairs was excised and DNA was eluted using a NaI extraction and glass powder binding (GeneClean, Bio101, La Jolla, Calif.). The gel-purified fragment was ligated into SmaI-digested Bluescript II SK(+) and the resulting plasmid contained a partial protein kinase domain that was used as a source of cDNA for library screening. Ten micrograms of this plasmid was digested with EcoRI and BamHI to liberate the subcloned fragment and the reaction was electrophoresed through a 1% agarose gel. The approximately 540 nucleotide fragment was eluted from the gel and was radiolabelled by random primed oligonucleotide directed labelling (Amersham, Arlington Heights, Ill.) using $^{32}$P-dCTP as the radioactive nucleotide. The radioactive probe was used to screen a human Manca B cell lymphoma library [Wiman, et al., *Proc. Natl. Acad. Sci. (USA)* 81:6798–6802 (1984)] prepared in phage cloning vector γgt10 prepared as follows. Poly d(A)⁺RNA was prepared from 2.8×10⁸ cells of the B-cell lymphoma Manca using the "Fast Track" kit (Invitrogen). 5 μg of RNA was used for oligo d(T) primed CDNA synthesis with the cDNA Synthesis System (Gibco BRL, Burlington, Ontario, Canada); the resulting cDNA was size selected by agarose gel electrophoresis and ligated to EcoRI adapters with the Ribo Clone kit (Promega, Madison, Wis.). Varying amounts of the adapted cDNA were ligated to EcoRI-digested γgt10 with 1 unit of T4 DNA ligase (Boehringer Mannheim, Indianapolis, Ind.) in a commercially prepared buffer supplied by the manufacturer with the enzyme. The ligations were packaged with Gigapack packaging extracts (Stratagene) and the resulting phage pool (1.5×10⁶ phage) was amplified in the C600 Hfl strain. A total of 1×10⁶ phage plaques were screened by standard hybridization methods (Maniatis, et al., supra). Hybridizations were at 65° C. for 18 hours in 6X SSPE (20X SSPE is 175.3 g/l NaCl, 27.6 g/l NaH$_2$PO$_4$.H$_2$O), 7.4 g/l EDTA, pH 7.4), 100 μg/ml salmon sperm carrier DNA, 5X Denhardt Reagent (50X Denhardts is 5% ficoll, 5% polyvinyl pyrolidone, 5% bovine serum albumin), 0.1% SDS and 5% sodium dextran sulfate. Filters were washed four times in 0.1X SSPE, 1% SDS. Each wash was at 65° C. for 30 minutes. Five clones were chosen for further analysis.

DNA from these phage clones was prepared using a Qiagen lambda DNA preparation kit (Qiagen, Chatsworth, Calif.) and human CDNA inserts were excised by EcoRI digestion. These inserts were subcloned into EcoRI-digested plasmid Bluescript II SK(+) (Stratagene) and the inserts were sequenced using an ABI 373A automated DNA sequencer. Two of the five cDNA contained near full-length cDNAS with a polyA tail and a protein kinase open reading frame. These protein kinases were most closely related to isoforms of casein kinase I were designated CKIγ1Hu and CKIγ2Hu. The DNA sequences of CKIγ1Hu and CKIγ2Hu are set out in SEQ ID NOS: 30 and 32, respectively; the deduced amino acid sequences of CKIγ1Hu and CKIγ2Hu are set out in SEQ ID NOS: 31 and 33, respectively.

EXAMPLE 13

Isolation of CKIδHu

Human CKIδ was subcloned by first isolating the human gene from a human fetal brain library constructed in λZAPII (Stratagene). A 2.2 kb EcoRI fragment containing rat CKIδ was gel purified through 1% agarose, isolated from the gel by NaI extraction with glass powder (Bio101, La Jolla, Calif.), and radiolabelled by random primer methods (Boehringer Mannheim) using $^{32}$P-dCTP. This probe was used to screen 1×10⁶ plaques containing human fetal brain cDNA library. Plaque hybridization conditions were 3X SSC, 0.1% Sarkosyl, 10X Denhardts reagent, 50 μg/ml salmon sperm DNA carrier. Hybridization was allowed to proceed for 18 hours at 65° C. after which time the filters were washed 4 times for 30 minutes each at 65° C. in 2X SSC, 1.0% SDS. Positive clones were identified by autoradiography at −70° C. with an enhancing screen and sequenced using an automated ABI373A DNA sequencer (Applied Biosystems, Foster City, California).

One clone was determined to encode a full length CKIδ isoform and was designated CKIδHu. The nucleotide sequence for CKIδHu is set out in SEQ ID NO: 34, and the deduced amino acid sequence is set out in SEQ ID NO: 35.

Expression of the CKIδHu isoform was then determined in eight different human tissues using an approximately 1.2 kb EcoRI fragment as a probe. CKIδHu mRNA levels were highest in kidney, liver and placenta cells, in contrast to the testes-specific expression of rat CKIδ demonstrated by Graves, et al., [supra].

TABLE 2

Sequence Homology Between CKI Isoforms

|  | HRR25 | Human CKIα1 | Human CKIγ1 | Human CKIγ2 | Human CKIδ |
|---|---|---|---|---|---|
| HRR25 | 100 | 68 | 50 | 50 | 65 |
| Human CKIα1 |  | 100 | 52 | 52 | 76 |
| Human CKIγ1 |  |  | 100 | 99 | 55 |
| Human CKIγ2 |  |  |  | 100 | 55 |
| Human CKIδ |  |  |  |  | 100 |

EXAMPLE 14

Complementation of Yeast CKI Mutants by Human CKI Genes

In order to determine if CKIγ1Hu was an isoform of yeast HRR25-like protein the gene was expressed in yeast protein kinase mutants. The cDNA was expressed under control of the yeast GAL1 promoter. The expression plasmid was a derivative of plasmid pRS305 (Stratagene) that contains the yeast GAL1 promoter. The parental plasmid with the GAL1 promoter was previously described [Davis et al., *Cell* 61:965–978 (1990)] and contained a BglII site adjacent to the GAL1 promoter as well as BamHI and SacI sites adjacent to the BglII site. This plasmid was modified by site-directed mutagenesis to contain a unique NcoI site between the GAL1 promoter and the BglII site. The NcoI site was adjacent to the GAL1 promoter such that the order of genetic elements was GAL1 promoter-NcoI-BglII-BamHI-SacI. Site-directed mutagenesis (MutaGene kit, BioRad) employed the oligonucleotide

5'-CTA GAT CTA GCT AGA CCA TGG TAG TTT TTT CTC
CTT GAC G-3' (SEQ ID NO. 36)

and generated a unique NcoI site (underlined in SEQ ID NO: 36). The resulting plasmid was called pRS305(N) 2μ GAL1.

To clone CKIγ1Hu into pRS305(N) 2μ GAL1, the CKIγ1Hu cDNA was amplified from cDNA with oligonucleotides that would introduce an NcoI site at the initiating ATG and a BamHI site in the 3' untranslated region. The sequence of the mutagenic oligonucleotide (with the NcoI site underlined) for the amino terminus was

5'-CAT GCC ATG GCA CGA CCT AGT-3'  (SEQ ID NO: 37).

The oligonucleotide M13rev, purchased from Stratagene (Stratagene, La Jolla, Calif.) was used to introduce the BamHI site in the 3' untranslated region. Amplification conditions used 200 Mm Tris-HCl (Ph 8.2), 100 Mm KCl, 60 mM (NH4)$_2$SO$_4$, 15 mM MgCl$_2$, 1% Triton X-100, 0.5 µM of each primer, 100 ng template, 200 µM of each dNTP and 2.5 units polymerase. The reactions were performed for 30 cycles. Reactions were started with a 4 minute treatment at 94° C. and all cycles were 1 minute at 94° C. for denaturing, 2 minutes at 50° C. for annealing, and 4 minutes at 72° C. for extension. The amplified product was digested with NcoI and BamHI and was cloned into NcoI/BamHI-digested pRS305(N) 2µ GAL1.

Complementation of yeast CKI mutants employed yeast strains 7D (hrr 25 Δ, ura3-1, trp1-1, leu2-3, 112, his3-11,15, can1-100, ade2-1) [DeMaggio, et al., (1992) supra] and YI227 (cki1D, cki2D, FOA$^R$, ade2-1, can1-100, his3-11,15, leu2-3,12, trp1-1, ura3-1, pRS415::Ckilts) Strain 7D lacked the HRR25 isoform of yeast CKI and strain YI227 contained a temperature sensitive allele of yeast CKI1. Yeast strains were transformed by lithium acetate-mediated transformation methods and transformants were selected on SD-leucine medium (Bio101). Controls for transformation were plasmids pRS305(N) 2 µg GAL1 alone, plasmid pRS315 (Stratagene), and plasmid pRS315::HRR25, which contains a SalI-EcoRI genomic fragment that spans the genomic HRR25 fragment [Hoekstra et al., Science, supra]. Plasmid pRS315::HRR25 was constructed by ligating a SalI/EcoRI genomic fragment of HRR25 into SalI/EcoRI-digested pRS315. Both HRR25 and CKIγ1Hu, when expressed in yeast mutants, are capable of fully complementing for the temperature-sensitive growth defect of CKI. In addition, CKIγ1Hu partially suppressed a severe growth rate defect associated with HRR25 mutants. The partial suppression of HRR25 growth defects by CKIγ1Hu was detected by a 10–20 fold greater plating efficiency relative to pRS305(N) 2µ GAL1.

To extend the complementation analysis to additional CKI family members, the ability of other human CKIαHu and CKIδHu genes to complement for the HRR25 mutant defects was examined. Human CKIα1Hu was subcloned into plasmid pRS305(N) 2µ GAL1 by first introducing an NcoI site at the initiating methionine by site-directed mutagenesis. The mutagenic oligonucleotide (with the NcoI site underlined) was

5'-CTA GAT CTA GCT AGA CCA TGG TAG TTT TTT CTC CTT GAC G-3'  (SEQ ID NO: 38)

and mutagenesis was performed using the Mutagene kit (BioRad). The mutagenized cDNA was digested with NcoI and BglII and the CKIα1Hu fragment was ligated into pRS305(n) 2µ GAL1.

Two constructs containing the CKIδHu cDNA were examined for complementation. Plasmid pEC7B (containing CKIδHu cDNA) was used as a template for site-directed mutagenesis (MutaGene, BioRad). The mutagenic oligonucleotide

5'-GAA TCG GGC CGC CGA GAT CTC ATA TGG AGC TGA GAG TC-3'  (SEQ ID NO: 39)

was used to introduce BglII (underlined in SEQ ID NO: 39) and NdeI (in italics in SEQ ID NO: 39) sites at the initiating ATG of CKIδHu. One plasmid construction employed BglII/SacI-digested CKI DNA from the mutagenized cDNA that was ligated into BglII/SacI-digested pRS305(N) 2µ GAL1 to produce pRS305(CKIδ). The second plasmid construct employed NcoI/SacI-digested CKIδHu cDNA from unmutagenized pEC7B cDNA that was ligated into NcoI/SacI-digested pRS305(N) 2µ GAL1 to produce pRS305(N)(CKIδ). Plasmid pRS305(CKIδ) contained the nucleotides

5'-CCC GGA TCT AGC AGA TCT CAT-3'  (SEQ ID NO: 40)

between the GAL1 promoter and the initiating methionine of CKIδ. Plasmid pRS305(N)(CKIδ) had a near-perfect fusion between the initiating methionine of CKIδHu and the 3' end of GAL1. Near perfect fusion indicates that the promoter and initiating methionine codon have few or no intervening nucleic acid sequences, and therefore are approximately abutting.

The CKIα1Hu and CKIδHu-containing plasmids were transformed into yeast strains 7D and YI227 and were examined for their ability to complement for their mutant defects. Like CKIγHu, CKIα1Hu partially complemented the growth defect associated with HRR25 mutations. CKIδHu was able to complement for the growth defect of temperature-conditional CKI strains, for the growth defect of HRR25 mutants, and for the DNA repair defect of HRR25. The ability of CKIδHu to complement for mutant defects in these yeast strains was indistinguishable from yeast HRR25 or CKI genes only when the appropriate plasmid construct was employed. Plasmid pRS305(CKIδ), which contained the additional 21 bases was unable to complement for any mutant phenotypes, while the near-perfect fusion in pRS305(N)(CKIδ) was fully functional. This difference was attributed to the inability of yeast to translate extended and/or CG rich leader sequences.

EXAMPLE 15

Generation of Monoclonal Antibodies

A. CKIαHu Peptides

Monoclonal antibodies were raised against the following peptides. SEQ ID NO: 41 was derived from the common amino terminus of CKIα1Hu, CKIα2Hu, and CKIα3Hu, and SEQ ID NO: 42 was derived from an internal alternative splice region in CKIα3Hu.

NH$_2$-ASSSGSKAEFIVGGY-COOH  (SEQ ID NO: 41)

NH$_2$-RSMTVSTSQDPSFSGY-COOH  (SEQ ID NO: 42)

These peptides were initially each coupled to bovine gamma globulin (Sigma, St. Louis, Mo.). Five mg of gamma globulin and 5 mg of peptide were resuspended in 0.4 ml 100 mM K$_2$HPO$_4$ (pH 7.2) and to this mixture, 35 mg 1-ethyl-3(3-dimethylamino propyl)-carbodiimide-HCl (EDC, Pierce) previously dissolved in 50 µl K$_2$HPO$_4$ (pH 7.2) was added. The reaction was allowed to proceed for 16 hr at 4° C. and was quenched by addition of 0.25 ml 2M ethanolamine and 0.25 ml acetic acid. The reaction mixture was then diluted to a final volume of 2.5 ml with PBS and desalted using Sephadex G-25M (Pharmacia) chromatography. Protein containing fractions were concentrated by centrifugal microconcentration (Amicon). Mice were then injected with 50 µg of the coupled peptide nine times over a period of 8 months. Antibody production was measured against the respective peptides by ELISA.

Fusions were performed by standard methods. Briefly, a single-cell suspension was formed by grinding the spleen between the frosted ends of two glass microscope slides submerged in serum free RPMI 1640 media, supplemented with 2 mM L-glutamine, 1 mM sodium pyruvate, 100 units/ml penicillin, and 100 µg/ml streptomycin (RPMI) (Gibco). The cell suspension was filtered through a sterile 70-mesh Nitex cell strainer (Becton Dickinson, Parsippany, N.J.), and washed twice by centrifuging at 200 g for 5 minutes and the pellet resuspended in 20 ml serum free RPMI. Thymocytes taken from 3 naive Balb/c mice were prepared in a similar manner.

NS-1 myeloma cells, kept in log phase in RPMI with 11% fetal bovine serum (FBS) (Hyclone, Laboratories, Inc., Logan, Utah) for three days prior to fusion, were centrifuged at 200 g for 5 minutes, and the pellet was washed twice as described in the foregoing paragraph. After washing, each cell suspension was brought to a final volume of 10 ml in serum free RPMI, and 10 µl was diluted 1:100. From each dilution, 20 µl was removed, mixed with 20 µl 0.4% trypan blue stain in 0.85% saline (Gibco), loaded onto a hemacytometer (Baxter Healthcare Corp., Deerfield, Ill.) and cells counted.

Approximately $2\times10^8$ spleen cells were combined with $4\times10^7$ NS-1 cells, centrifuged, and the supernatant was aspirated. The cell pellet was dislodged by tapping the tube and 2 ml of 37° C. PEG 1500 (50% in 75 mM Hepes, Ph 8.0) (Boehringer Mannheim) was added with stirring over the course of 1 minute, followed by adding 14 ml of serum free RPMI over 7 minutes. An additional 16 ml RPMI was added and the cells were centrifuged at 200 g for 10 minutes. After discarding the supernatant, the pellet was resuspended in 200 ml RPMI containing 15% FBS, 100 µM sodium hypoxanthine, 0.4 µM aminopterin, 16 µM thymidine (HAT) (Gibco), 25 units/ml IL-6 (Mallinckrodt, St. Louis, Mo.) and $1.5\times10^6$ thymocytes/ml. The suspension was dispensed into ten 96-well flat bottom tissue culture plates (Corning, Essex, United Kingdom) at 200 µl/well. Cells in the plates were fed 2–3 times between fusing and screening by aspirating approximately half of the medium from each well with an 18 gauge needle (Becton Dickinson), and replenishing plating medium described above except containing 10 units/ml IL-6 and lacking thymocytes.

Fusions were screened when cell growth reached 60–80% confluency (usually 7–9 days). Fusion 75 was screened by ELISA on either the common amino terminal peptide (SEQ ID NO: 41) or the internal peptide (SEQ ID NO: 42), and fusion 80 was screened on the amino terminal peptide (SEQ ID NO: 41) only. Immulon 4 plates (Dynatech, Cambridge, Mass.) were coated at 4° C. overnight with 100 ng/well peptide in 50 mM carbonate buffer, Ph 9.6. Plates were washed three times with PBS containing 0.05% Tween 20 (PBST) and 50 µl culture supernatant was added. After incubation at 37° C. for 30 minutes, and washing as above, 50 µl horseradish peroxidase conjugated goat anti-mouse IgG(fc) (Jackson ImmunoResearch, West Grove, Pa.) diluted 1:3500 in PBST was added. Plates were incubated as above, washed four times with PBST and 100 µl substrate, consisting of 1 mg/ml o-phenylene diamine (Sigma) and 0.1 µl/ml 30% $H_2O_2$ in 100 mM citrate, pH 4.5, was added. The color reaction was stopped in 5 minutes with the addition of 50 µl of 15% $H_2SO_4$. Absorbance at 490 nm was read on a plate reader (Dynatech).

Three wells from each fusion (designated 75D3G, 75C1OH, 75C2g, 80G1OH, 80H4F, and 80J9E) were cloned two to three times, successively, by doubling dilution in RPMI, 15% FBS, 100 µM sodium hypoxanthine, 16 µM thymidine and 10 units/ml IL-6. Wells of clone plates were scored visually after 4 days and the number of colonies in the least dense wells were recorded. Selected wells of each cloning were tested by ELISA as above. In the final cloning, positive wells containing single colonies were expanded in RPMI with 11% FBS.

Three antibodies were determined to be reactive for the peptide raised against the amino terminus of CKIαHu (80 G10H11D, 80 H12F12B, and 80 J9E10C), and three antibodies were reactive with the peptide raised against the internal fragment of CKIα3Hu (75 D3G10A, 75 C10H1D, and 75 C2G11F). Clones 75D3G, 75C10H, 75C2G, and 80G10H were isotyped to be IgG1, clone 80H4F IgG3, and 80J9E IgG2a.

B. CKIHu/Thioredoxin Fusion Proteins

Expression plasmids were constructed in order to express the CKIHu isoforms as fusion proteins with thioredoxin. Specifically, the coding sequence for each isoform was amplified by PCR with primers which created a 5'XbaI restriction site and a 3'BamHI site. The primer used to create the XbaI site for the CKIαHu isoforms is set out in SEQ ID NO: 43 with the XbaI site underlined.

5'-T ACA <u>TCT AGA</u> ATT ATG GCG AGT AGC AGC GGC-3'   (SEQ ID NO: 43)

The primer used to create the 3'BamHI site in the CKIα1Hu coding sequence is set out in SEQ ID NO: 44, with BamHI site underlined.

5'-AAT <u>GGA TCC</u> TTA GAA ACC TGT GGG GGT-3'   (SEQ ID NO: 44)

The primer used to create the BamHI site in the CKIα2Hu and CKIα3Hu coding sequences is set out in SEQ ID NO: 45, with the BamHI site underlined.

5'-AAT <u>GGA TCC</u> TTA GAA ACC TTT CAT GTT ACT CTT GGT-3'   (SEQ ID NO: 45)

The XbaI and BamHI sites were created in the CKIδHu coding sequences with primers set out in SEQ ID NOS: 46 and 47, respectively.

5'-T ACA TCT AGA ATT ATG GAG CTG AGA GTC GGG-5'   (SEQ ID NO: 46)

5'-<u>GGA TCC</u> TCA TCG GTG CAC GAC AGA CTG-3'   (SEQ ID NO:47)

The primers used to create the XbaI and BamHI sites in the coding regions of the CKIγHu isoforms are set out in SEQ ID NO: 48 and 49.

5'T ACA <u>TCT AGA</u> ATT ATG GCA CGA CCT AGT GGT CGA TCG-3'   (SEQ ID NO: 48)

5'-G <u>GGG ATC CTA</u> CTT CAG TAG GGG CTG-3'   (SEQ ID NO: 49)

Digestion of the resulting PCR products with XbaI and BamHI allowed the fragments to be directionly cloned in frame at the carboxy terminus of sequences encoding thioredoxin in plasmid pTRXFUS [LeVallie, et al., Nature/Biotechnology 11:187-193 (1993)]. The resulting expression constructions contained the laq Iq gene, followed by the tacII promoter (from plasmid pMal-c2, New England Biolabs, Beverly, Mass.) which drives expression of the E. coli thioredoxin gene fused at the amino termini of the CKI catalytic domains.

E. coli XL-1 Blue cells (Stratagene) were transformed with the individual expression plasmids by standard methods and grown at 37° C. to mid-log phase. Samples were collected to serve as controls for uninduced cells and the remaining cells were induced for four hours with 0.25 mM IPTG at 37° C. Cells were then lysed and inclusion bodies in the insoluble extract from cleared lysate were used to inject mice.

C. Other CKI Peptides

Monoclonal antibodies were also raised against other CKI peptides coupled to bovine gamma globulin as in section A of this example. Peptides derived from the amino termini of the CKIγHu isoforms are set out in SEQ ID NOS: 50 and 51; peptides derived from the amino termini of bovine CKIβ [Rowles, et al., supra] are set out in SEQ ID NOS: 52 and 53; peptides derived from the amino terminus and carboxy terminus of CKIδHu are set out in SEQ ID NOS: 54 and 55, respectively; a peptide derived from the carboxy termini of CKIα2Hu and CKIα3Hu is set out in SEQ ID NO: 56; and a peptide common to all CKIHu isoforms is set out in SEQ ID NO: 57. The common CKI sequence set out in SEQ ID NO: 57 was also injected into rabbits to produce polyclonal antisera.

| | |
|---|---|
| NH$_2$-RSGHNTRGTGSS-COOH | (SEQ ID NO: 50) |
| NH$_2$-RLGHNTRGTGSS-COOH | (SEQ ID NO: 51) |
| NH$_2$-SSRPKTDVLVG-COOH | (SEQ ID NO: 52) |
| NH$_2$-KSDNTKSEMKHS-COOH | (SEQ ID NO: 53) |
| NH$_2$-GTDIAAGE-COOH | (SEQ ID NO: 54) |
| NH$_2$-ERRDREERLR-COOH | (SEQ ID NO: 55) |
| NH$_2$-TGKQTDKTKSNMKGY-COOH | (SEQ ID NO: 56) |
| NH$_2$-DLLGPSLEDLFGY-COOH | (SEQ ID NO: 57) |

Mice were injected with 50 μg of the peptide/gamma globulin complex on a varying schedule over a period of eight months.

Subsequent to the filing of U.S. patent application Ser. No. 07/728,783 on Jul. 3, 1991, there have been numerous reports in the scientific literature of the isolation of DNAs encoding HRR25-like proteins. For example, Rowles, et al. (Proc. Natl. Acad. Sci. USA, 88:9548-9592, 1991) reported the purification of a bovine thymus casein kinase I (CKI) enzyme. The sequencing of tryptic fragments reveled nearly 25% of the primary sequence of the enzyme. PCR cloning resulted in development of partial clones coding for the CKI enzyme isolate and a homologue enzyme referred to as CKI-δ. Screening of bovine brain libraries with the partial clones yielded full length cDNAs for the CKI isolate (designated CKIα) and two additional homologues (CKIβ and CKIγ). The deduced sequence for bovine CKIα was noted by Rowles, et al., [supra] to be 60% homologous to HRR25 over its catalytic domain. As noted earlier, a comparison of the bovine CKIα sequence of Rowles, et al. to human CKIα1 sequence set out in SEQ. ID. NO: 7 and 8 reveals 100% homology in the catalytic domain.

As another example, Robinson, et al. (Proc. Natl. Acad. Sci. USA, 89:28-32, 1992) describes the isolation of two Saccharomyces cerevisiae genes, YCK1 and YCK2 which encode yeast casein kinase 1 homologues and also describes purification and partial sequencing of a rabbit casein kinase I from a rabbit reticulocyte lysate preparation. HRR25 was noted to be 50% homologous to YCK1 and YCK2 and 60% homologous to the partial rabbit CKI sequence. As a further example, Wang, et al. (Molecular Biology of the Cell, 3:275-286, 1992) describes the isolation of a 54 kDa CKI from S. cerevisiae and the use of amino acid sequence information therefrom for cloning two yeast cDNAs encoding homologous casein kinase I proteins, CKI1 and CKI2. Comparison of the catalytic domains of the protein encoded by the CKI1 gene produced few alignments revealing greater than 20-25% homology. The closest matches were with HRR25 (50-56%) and with the three bovine isozymes of Rowles, et al. (51-56%). The YCK1 sequence of Robinson, et al. corresponds to the CKI2 sequence of Wang, et al.; the YCK2 sequence corresponds to CKI1. Brockman, et al. (Proc. Natl. Acad. Sci, USA, 89:9454-9458, 1992) reported the immunopurification and sequencing of a human erythroid casein kinase I and noted that it was 62% homologous to HRR25. As a final example, Graves, et al. (J. Biol. Chem. 265:6394-6401, 1993) reported the cloning and characterization of a casein kinase I from rat testes. This CKI, designated CKIδ, shared 76% homology at the amino acid level with CKIα isolated from bovine brain and 65% homology with HRR25.

While the foregoing illustrative examples are specifically directed to isolation of "full length" polynucleotides encoding the HRR25-like proteins HRR25, Hhp1+, Hhp2+, CKIα1Hu, CKIα2Hu, CKIα3Hu, CKIδHu, CKIγ1Hu and CKIγ2Hu, it will be readily understood that the present invention is not limited to those polynucleotides. Rather it embraces all polynucleotides which are comprehended within the class of genes encoding HRR25-like proteins characterized protein kinase activity and by homology of 35% or more with the HRR25 protein through the protein kinase catalytic domain. By way of example, employing information concerning the DNA sequence of HRR25, the procedures of Example 7 allowed the isolation partial cDNA clones of expected length from cDNA libraries derived from Arabidopsis thaliana, Drosophila melanogaster, Xenopus, chicken, mouse, rat, and human species. These partial cDNAs may, in turn, be employed in the manner of Examples 6 and 7 to isolate full length DNA clones encoding HRR25-like proteins from these species. Each of these may be employed in the large scale production of the corresponding proteins by recombinant methods or for the generation of other useful polynucleotides such as antisense RNAs. Recombinant expression products of such HRR25-like DNAs may be employed for generation of antibodies and in screens for compounds which modulate the protein kinase and/or recombination/repair functions of these enzymes. Moreover, as suggested in the publication of Rowles, et al., Robinson, et al., and Wang, et al., multiple HRR25-like isozymes are expected to exist in a variety of eukaryotic species as both membrane bound and cytoplasmic proteins. It appears reasonable to expect that a number of genes and gene products exist in human species, all of which are functionally related as well as structurally related to each other and to HRR25.

The invention now being fully described, it will be apparent to one of ordinary skill in the art that various changes and modifications can be made without departing from the spirit or scope of the invention.

SUMMARY OF SEQUENCES

SEQ ID NO: 1 is the nucleic acid sequence and the deduced amino acid of a genomic fragment encoding a yeast-derived protein kinase, HRR25 of the present invention.

SEQ ID NO: 2 is the deduced amino acid sequence of a yeast-derived protein kinase HRR25 of the present invention.

SEQ ID NO: 3 is the nucleic acid sequence (and the deduced amino acid sequence) of a genomic fragment encoding Hhp1+ of the present invention.

SEQ ID NO: 4 is the deduced amino acid sequence of Hhp1+ of the present invention.

SEQ ID NO: 5 is the nucleic acid sequence (and the deduced amino acid sequence) of a genomic fragment encoding Hhp2+ of the present invention.

SEQ ID NO: 6 is the deduced amino acid sequence of Hhp2+ of the present invention.

SEQ ID NO: 7 is the nucleic acid sequence (and the deduced amino acid sequence) of a genomic fragment encoding CKIα1Hu of the present invention.

SEQ ID NO: 8 is the deduced amino acid sequence of CKIα1Hu of the present invention.

SEQ ID NO: 9 is the nucleic acid sequence (and the deduced amino acid sequence) of a genomic fragment encoding CKIα2Hu of the present invention.

SEQ ID NO: 10 is the deduced amino acid sequence of CKIα2Hu of the present invention.

SEQ ID NO: 11 is the nucleic acid sequence (and the deduced amino acid sequence) of a genomic fragment encoding CKIα3Hu of the present invention.

SEQ ID NO: 12 is the deduced amino acid sequence of CKIα3Hu of the present invention.

SEQ ID NO: 13 is the primer, 4583, representing top strand DNA encoding residues 16–23 of HRR25.

SEQ ID NO: 14 is the primer, 4582, representing top strand DNA encoding residues 126–133 of HRR25.

SEQ ID NO: 15 is the primer, 4589, representing bottom strand DNA encoding residues 126–133 of HRR25.

SEQ ID NO: 16 is the primer, 4590, representing bottom strand DNA encoding residues 194–199 of HRR25.

SEQ ID NO: 17 is the primer JH21, representing bovine top strand DNA bases 47–67.

SEQ ID NO: 18 is the primer JH22, representing bovine top strand DNA bases 223–240.

SEQ ID NO: 19 is the primer JH29, representing bovine top strand DNA bases 604–623.

SEQ ID NO: 20 is the primer JH30, representing bovine bottom strand DNA bases 623–604.

SEQ ID NO: 21 is the primer JH31, representing bovine bottom strand DNA bases 835–817.

SEQ ID NO: 22 is the mutated HRR25 kinase domain primer found on p. 33, Example 3.

SEQ ID NO: 23 is the nucleic acid sequence (and the deduced amino acid sequence) of a genomic fragment encoding NUF1 of the present invention.

SEQ ID NO: 24 is the deduced amino acid sequence of NUF1 of the present invention.

SEQ ID NOS: 25, 26 and 27 are the conserved motifs found on page 18.

SEQ ID NOS: 28 and 29 are redundant oligonucleotides, based on conserved regions of HRR25-like proteins, used to amplify a probe from a human cDNA library.

SEQ ID NO: 30 is the nucleotide sequence of the CKIγ1Hu gene.

SEQ ID NO: 31 is the deduced amino acid sequence of the CKIγ1Hu protein.

SEQ ID NO: 32 is the nucleotide sequence of the CKIγ2Hu gene.

SEQ ID NO: 33 is the deduced amino acid sequence of the CKIγ2Hu protein.

SEQ ID NO: 34 is the nucleic acid sequence for CKIδHu.

SEQ ID NO: 35 is the deduced amino acid sequence for CKIδHu.

SEQ ID NO: 36 is the mutagenic oligonucleotide used to generate an NcoI restriction site in expression plasmid pRS305.

SEQ ID NO: 37 is the mutagenic oligonucleotide used to generate an NcoI restriction site in CKIγ1.

SEQ ID NO: 38 is the mutagenic oligonucleotide used to create an NcoI restriction site in human CKIα.

SEQ ID NO: 39 is the mutagenic oligonucleotide used to introduce a BglII restriction site in CKIδ.

SEQ ID NO: 40 is the intervening nucleic acids sequence between the GAL1 promoter and initiating methionine codon in the CKIδ expression plasmid.

SEQ ID NOS: 41 and 42 are amino terminal and internal peptide fragments of CKIα isoforms to generate monoclonal antibodies.

SEQ ID NO: 43 is the primer used to create a XbaI restriction site in CKIαHu coding sequences.

SEQ ID NO: 44 is the primer used to create a BamHI restriction site in the CKIα1Hu coding sequence.

SEQ ID NO: 45 is the primer used to create a BamHI restriction site in the CKIα2Hu and CKIα3Hu coding sequences.

SEQ ID NO: 46 is the primer used to create a XbaI restriction site in the CKIδHu coding sequence.

SEQ ID NO: 47 is the primer used to create a BamHI restriction site in the CKIδHu coding sequence.

SEQ ID NO: 48 is the primer used to create a XbaI restriction site in the CKIγ1Hu and CKI γ2Hu coding sequences.

SEQ ID NO: 49 is the primer used to create a BamHI restriction site in the CKIγ1Hu and CKIγ2Hu coding sequences.

SEQ ID NO: 50 is an amino terminal peptide fragment of CKIγHu coupled to bovine gamma globulin and used to generate monoclonal antibodies in mice.

SEQ ID NO: 51 is an amino terminal peptide fragment of CKIγHu coupled to bovine gamma globulin and used to generate monoclonal antibodies in mice.

SEQ ID NO: 52 is an amino terminal peptide fragment of bovine CKIβ coupled to bovine gamma globulin and used to generate monoclonal antibodies in mice.

SEQ ID NO: 53 is an amino terminal peptide fragment of bovine CKIβ coupled to bovine gamma globulin and used to generate monoclonal antibodies in mice.

SEQ ID NO: 54 is an amino terminal peptide fragment of CKIδHu coupled to bovine gamma globulin and used to generate monoclonal antibodies in mice.

SEQ ID NO: 55 is a carboxy terminal peptide fragment of CKIδHu coupled to bovine gamma globulin and used to generate monoclonal antibodies in mice.

SEQ ID NO: 56 is an carboxy terminal peptide fragment of CKIα2Hu and CKIα3Hu coupled to bovine gamma globulin and used to generate monoclonal antibodies in mice.

SEQ ID NO: 57 is an internal terminal peptide fragment common to all human CKI isoforms coupled to bovine gamma globulin and used to generate monoclonal antibodies in mice.

We claim:

1. A method of identifying a composition which modulates the DNA double strand break repair promoting activity of a human HRR25-like protein possessing greater than 35% amino acid sequence homology to the S. cerevisiae HRR25 protein kinase of SEQ ID NO: 2 in the protein kinase catalytic domain comprising amino acid residues 1 through 287 thereof, said method comprising the steps of:

(a) incubating a system of components comprising the composition and the protein in the presence of a substrate for said protein wherein incubation is carried out under conditions sufficient to allow the components to interact; and (b) measuring the change in activity of said protein on said substrate.

2. The method of claim 1 wherein the DNA double strand break consists of:

↓
CAACAG
GTTGTC
↑

* * * * *